United States Patent
Betancourt et al.

(10) Patent No.: US 11,452,692 B2
(45) Date of Patent: *Sep. 27, 2022

(54) COMPOSITIONS AND METHODS FOR TREATING DISORDERS AMELIORATED BY MUSCARINIC RECEPTOR ACTIVATION

(71) Applicant: Karuna Therapeutics, Inc., Boston, MA (US)

(72) Inventors: Aimesther Betancourt, Montreal (CA); Bruce Rehlaender, Lake Oswego, OR (US); Roch Thibert, Mont-Royal (CA)

(73) Assignee: Karuna Therapeutics, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/649,826

(22) Filed: Feb. 3, 2022

(65) Prior Publication Data
US 2022/0151933 A1 May 19, 2022

Related U.S. Application Data

(63) Continuation of application No. 17/143,904, filed on Jan. 7, 2021, which is a continuation of application (Continued)

(51) Int. Cl.
| A61K 9/16 | (2006.01) |
| A61K 31/439 | (2006.01) |
| A61K 31/454 | (2006.01) |
| A61K 9/48 | (2006.01) |
| A61K 9/00 | (2006.01) |

(52) U.S. Cl.
CPC .......... *A61K 9/1652* (2013.01); *A61K 9/0053* (2013.01); *A61K 9/1611* (2013.01); *A61K 9/485* (2013.01); *A61K 9/4858* (2013.01); *A61K 9/4866* (2013.01); *A61K 31/439* (2013.01); *A61K 31/454* (2013.01)

(58) Field of Classification Search
CPC .................................................. A61K 9/1652
See application file for complete search history.

(56) References Cited

U.S. PATENT DOCUMENTS

| 4,647,580 A | 3/1987 | Roszkowski |
| 5,043,345 A | 8/1991 | Sauerberg |

(Continued)

FOREIGN PATENT DOCUMENTS

| AU | 2003299453 | 5/2004 |
| CA | 2804215 | 1/2011 |

(Continued)

OTHER PUBLICATIONS

Arehart-Treichel, J., "GABA Targeted for Study in Schizophrenia", Psych News, 40(9):29 & 52, (2005).

(Continued)

*Primary Examiner* — Benjamin J Packard
(74) *Attorney, Agent, or Firm* — Global Patent Group, LLC; Lauren Stevens; Clifford Schlecht

(57) ABSTRACT

Provided herein is an oral pharmaceutical composition, comprising a plurality of xanomeline beads having a core comprising xanomeline or a salt thereof; and a plurality of trospium beads having a core comprising a salt of trospium.

18 Claims, 42 Drawing Sheets

Related U.S. Application Data

No. 16/585,532, filed on Sep. 27, 2019, now Pat. No. 10,933,020.

(60) Provisional application No. 62/738,333, filed on Sep. 28, 2018.

(56) References Cited

U.S. PATENT DOCUMENTS

| | | |
|---|---|---|
| 5,480,651 A | 1/1996 | Callaway |
| 5,744,476 A | 4/1998 | Locke |
| 5,852,029 A | 12/1998 | Fisher |
| 6,423,842 B1 | 7/2002 | Grewal |
| 6,862,890 B2 | 3/2005 | Williams, III |
| 7,049,321 B2 | 5/2006 | Fisher |
| 7,410,978 B2 | 8/2008 | Kidane |
| 7,491,715 B2 | 2/2009 | Ek |
| 7,517,871 B2 | 4/2009 | Ek |
| 7,524,965 B2 | 4/2009 | Colson |
| 7,550,454 B2 | 6/2009 | Ek |
| 7,622,461 B2 | 11/2009 | Ek |
| 7,666,894 B2 | 2/2010 | Paborji |
| 7,678,821 B2 | 3/2010 | Paborji |
| 7,781,472 B2 | 8/2010 | Paborji |
| 7,786,166 B2 | 8/2010 | Frey, II |
| 7,790,905 B2 | 9/2010 | Tawa |
| 8,404,701 B2 | 3/2013 | Chase |
| 9,561,218 B2 | 2/2017 | Clarence-Smith |
| 9,671,678 B2 | 6/2017 | Tokura |
| 10,238,643 B2 | 3/2019 | Elenko |
| 10,265,311 B2 | 4/2019 | Elenko |
| 10,369,143 B2 | 8/2019 | Elenko |
| 10,369,144 B2 | 8/2019 | Elenko |
| 10,695,339 B2 | 6/2020 | Elenko |
| 10,925,832 B2 | 2/2021 | Betancourt |
| 10,933,020 B2 | 3/2021 | Betancourt |
| 2002/0010216 A1 | 1/2002 | Rogosky |
| 2003/0068365 A1 | 4/2003 | Suvanprakorn |
| 2004/0023951 A1 | 2/2004 | Bymaster |
| 2004/0058914 A1 | 3/2004 | Doi |
| 2004/0224012 A1 | 11/2004 | Suvanprakorn |
| 2005/0085463 A1 | 4/2005 | Weiner |
| 2005/0250767 A1 | 11/2005 | Weiner |
| 2005/0267078 A1 | 12/2005 | Gras Escardo |
| 2006/0018933 A1 | 1/2006 | Vaya |
| 2006/0189651 A1 | 8/2006 | Gras Escardo |
| 2006/0197831 A1 | 9/2006 | Takeuchi |
| 2006/0287294 A1 | 12/2006 | Zhu |
| 2006/0293356 A1 | 12/2006 | Aberg |
| 2007/0027160 A1 | 2/2007 | Asselin |
| 2007/0049576 A1 | 3/2007 | Barlow |
| 2007/0053995 A1 | 3/2007 | Paborji |
| 2007/0116729 A1 | 5/2007 | Palepu |
| 2008/0045565 A1 | 2/2008 | Gras Escardo |
| 2008/0114014 A1 | 5/2008 | Rich |
| 2009/0005722 A1 | 1/2009 | Jennlngs-Spring |
| 2009/0017111 A1 | 1/2009 | Van Den Heuvel |
| 2009/0082388 A1 | 3/2009 | Hacksell |
| 2009/0275629 A1 | 11/2009 | Paborji |
| 2009/0318522 A1 | 12/2009 | Paborji |
| 2010/0137392 A1 | 6/2010 | Paborji |
| 2010/0152263 A1 | 6/2010 | Paborji |
| 2010/0226943 A1 | 9/2010 | Brennan |
| 2011/0020423 A1 | 1/2011 | Elenko |
| 2011/0263613 A1 | 10/2011 | Hendrickson |
| 2016/0375001 A1* | 12/2016 | Chase ............... A61K 31/4178 514/257 |
| 2017/0056347 A1 | 3/2017 | Glick |
| 2017/0112820 A1 | 4/2017 | Elenko |
| 2017/0313687 A1 | 11/2017 | Hendrickson |
| 2018/0193311 A1 | 7/2018 | Benjamin |
| 2019/0167658 A1 | 6/2019 | Elenko |
| 2019/0192500 A1 | 6/2019 | Elenko |
| 2019/0307739 A1 | 10/2019 | Elenko |
| 2020/0101018 A1 | 4/2020 | Betancourt |
| 2020/0289419 A1 | 9/2020 | Betancourt |
| 2020/0323839 A1 | 10/2020 | Elenko |
| 2021/0145804 A1 | 5/2021 | Brannan |
| 2021/0154146 A1 | 5/2021 | Betancourt |
| 2021/0177762 A1 | 6/2021 | Betancourt |

FOREIGN PATENT DOCUMENTS

| | | |
|---|---|---|
| CL | 199600120 | 1/1996 |
| CL | 199600157 | 2/1996 |
| CL | 201800559 | 3/2018 |
| CL | 202100622 | 3/2021 |
| DE | 19612504 | 8/1997 |
| EP | 0734259 | 10/1996 |
| EP | 0813870 | 12/1997 |
| EP | 0813870 A1 | 12/1997 |
| EP | 2002843 | 12/2008 |
| EP | 2002844 | 12/2008 |
| JP | H10059848 | 3/1998 |
| JP | 2000516213 | 12/2000 |
| JP | 2004502655 | 1/2004 |
| JP | 2005530742 | 10/2005 |
| JP | 20050530742 | 10/2005 |
| JP | 2007510656 | 4/2007 |
| JP | 2009507021 | 2/2009 |
| WO | 1995005174 | 2/1995 |
| WO | 1998005207 | 2/1998 |
| WO | 1998005208 | 2/1998 |
| WO | 1998005291 | 2/1998 |
| WO | 1998005324 | 2/1998 |
| WO | 1998005325 | 2/1998 |
| WO | 1998005326 | 2/1998 |
| WO | 1998030243 | 7/1998 |
| WO | 2003030818 | 4/2003 |
| WO | 2003092580 | 11/2003 |
| WO | 2003092580 A2 | 11/2003 |
| WO | 2004060347 | 7/2004 |
| WO | 2004087161 | 10/2004 |
| WO | 2005044262 | 5/2005 |
| WO | 2005046684 | 5/2005 |
| WO | 2006067494 | 6/2006 |
| WO | 2006067496 | 6/2006 |
| WO | 2006086698 | 8/2006 |
| WO | 2007027675 | 3/2007 |
| WO | 2007049098 | 5/2007 |
| WO | 2008076287 | 7/2007 |
| WO | 2007125287 | 11/2007 |
| WO | 2007125290 | 11/2007 |
| WO | 2007125293 | 11/2007 |
| WO | 2007127196 | 11/2007 |
| WO | 2007128674 | 11/2007 |
| WO | 2008096111 | 8/2008 |
| WO | 2008096121 | 8/2008 |
| WO | 2008096126 | 8/2008 |
| WO | 2008096136 | 8/2008 |
| WO | 2008103351 | 8/2008 |
| WO | 2008104776 | 9/2008 |
| WO | 2008121268 | 10/2008 |
| WO | 2009036243 | 3/2009 |
| WO | 2009037503 | 3/2009 |
| WO | 2009039460 | 3/2009 |
| WO | 2009092601 | 7/2009 |
| WO | 2009132239 | 10/2009 |
| WO | 2010024870 | 3/2010 |
| WO | 2010064047 | 6/2010 |
| WO | 2010102218 | 9/2010 |
| WO | 2011011060 | 1/2011 |
| WO | 2011085406 | 7/2011 |
| WO | 2011123836 | 10/2011 |
| WO | 2012033956 | 3/2012 |
| WO | 2012170676 | 12/2012 |
| WO | 2014176460 | 10/2014 |
| WO | 2016144727 | 9/2016 |
| WO | 2016144749 | 9/2016 |
| WO | 2017040864 | 3/2017 |
| WO | 2017044714 | 3/2017 |
| WO | 2017127073 | 7/2017 |

(56) References Cited

FOREIGN PATENT DOCUMENTS

| WO | 2017147104 | 8/2017 |
|---|---|---|
| WO | 2020069301 | 4/2020 |
| WO | 2021101875 | 5/2021 |

OTHER PUBLICATIONS

Bai, Y. et al., "Therapeutic Effect of of Pirenzepine for Clozapine-Induced Hypersalivation: A Randomized, Double-Blind, Placebo Controlled, Cross-Over Study", J Clin Psychopharmacol., 21(6):608-11, (2001).
Barak, S. et al., "The M1/M4 Preferring Agonist Xanomeline Reverses Amphetamine-, MK801- and Scopolamine-Induced Abnormalities of Latent Inhibition: Putative Efficacy Against Positive, Negative and Cognitive Symptoms in Schizophrenia", Int J Neuropsychopharmacol., 14(9):1233-46, (2011).
Bender, A. et al., "Classics in Chemical Neuroscience: Xanomeline", ACS Chem Neurosci., 8(3):435-43, (2017).
Bewley, B. et al., "Discovery of a Novel, CNS Penetrant M4 PAM Chemotype Based on a 6+– Fluoro-4-(piperidin-1-yl)quinolone-3-Carbonite Core", Bioorg Med Chem Lett., 27(18):4274-9, (2017).
Bodick, N. et al., "Effects of Xanomeline, a Selective Muscarinic Receptor Agonist, on Cognitive Function and Behavioral Symptoms in Alzheimer Disease", Arch Neurol., 54(4):465-73, (1997).
Bolbecker, A. et al., "Muscarinic agonists and antagonists in schizophrenia: recent therapeutic advances and future directions", Handb Exp Pharmacol., 208:167-90, (2012).
Bonifazi, A. et al., "Synthesis and Biological Evaluation of a Novel Series of Heterobivalent Muscarinic Ligands Based on Xanomeline and 1-[3-(4-Butylpiperin-1-yl)propyl]-1,2,3,4-Tetrahydroquinolin-2-one (77-LH-28-1)", J Med Chem., 57(21):9065-77, (2014).
Bradley, S. et al., "AC-260584, an Orally Bioavailable M1 Muscarinic Receptor Allosteric Agonist Improves Cognitive Performance in an Animal Model", Neuropharmacology, 58(2):365-73, (2010).
Brannan et al. Muscarinic Cholinergic Receptor Agonist and Peripheral Antagonist for Schizophrenia, N Engl J Med, Feb. 25, 2021, vol. 384, pp. 717-726, [retrieved on May 4, 2022]. Retrieved from the Internet: <URL: https://www.nejm.org/doi/pdf/10.1056/NEJMoa2d17015? articleTools=true>.
Brannan, Stephen. (Oct. 5, 2018-Oct. 26, 2020) A Study to Assess Safety and Efficacy of KarXT in Adult Patients With Schizophrenia (EMERGENT-1). Identifier NCT03697252.
Brown, S. et al., "Causes of the Excess Mortality of Schizophrenia", Br J Psychiatry, 177:212-7, (2000).
Bymaster, F. et al., "Neurochemical Effects of the M1 Muscarinic Agonist Xanomeline (LY246708/NNC11-0232)", J Pharmacol Exp Ther., 269(1):282-9, (1994).
Bymaster, F. et al., "Role of the Cholinergic Muscarinic System in Bipolar Disorder and Related Mechanism of Action of Antipsychotic Agents", Mol Psychiatry, 7(Suppl 1):S57-63, (2000).
Bymaster, F. et al., "Xanomeline compared to other muscarinic agents on stimulation of phosphoinositide hydrolysis in vivo and other cholinomimetic effects", Brain Res., 795(1-2):179-90, (1998).
Carey, G. et al., "SCH 57790, A Selective Muscarinic M2 Receptor Antagonist, Releases Acetylcholine and Produces Cognitive Enhancement in Laboratory Animals", Eur J Pharmacol., 431(2):189-200, (2001).
Carnicella, S. et al., "Cholinergic Effects on Fear Conditioning II: Nicotinic and Muscarinic Modulations of Atropine-Induced Disruption of the Degraded Contingency Effect", Psychopharmacology (Berl), 178(4):533-41, (2005).
Caulfield, M. et al., "International Union of Pharmacology. XVII. Classification of Muscarinic Acetylcholine Receptors", Pharmacol Rev., 50(2):279-90, (1998).
Clinicaltrials.gov, "Pilot Study Comparing the Effects of Xanomeline Alone to Xanomeline Plus Tropsium", U.S. Nat'l Lib of Med., accessed online at <https://clinicaltraials.gov/ct2/show/NCT02831231> on Nov. 24, 2021, (2017).

Coward, D., "General Pharmacology of Clozapine", Br J Psychiatry Suppl., (17):5-11, (1992).
Croissant, B. et al., "Reduction of Side Effects by Combining Clozapine with Amisulpride: Case Report and Short Review of Clozapine-Induced Hypersalivation", Pharmacopsychiatry, 38(1):38-9, (2005).
Cutler, N. et al., "Scientific and Ethical Concerns in Clinical Trials in Alzheimers Patients: The Bridging Study", Eur J Clin Pharmacol., 48(6):421-8, (1995).
Davydov, L. et al., "Clozapine-Induced Hypersalivation", Ann Pharmacother., 34(5):662-5, (2000).
Dawe, G. et al., "Pathophysiology and Animal Models of Schizophrenia", Ann Acad Med Singapore, 38(5):425-30, (2009).
Dean, B. et al., "The Density of Muscarinic M1 Receptors is Decreased in the Caudate-Putamen of Subjects with Schizophrenia", Mol Psychiatry, 1(1):54-8, (1996).
Desbonnet, L. et al., "Mutant Models for Genes Associated with Schizophenia", Biochem Soc Trans., 37(pt 1):308-12, (2009).
DETROL® tolterodine tartrate tablets (Product Label) Prescribing Information, LAB-0329-4.0, Pharmacia & Upjohn, a division of Pfizer Inc., issued Apr. 2009; 17 pages.
Dixit, R. et al., "Oral Strip Technology: Overview and Future Potential", J Control Release, 139(2):94-107, (2009).
Eglen, R., "Muscarinic Receptor Subtypes in Neuronal and Non-Neuronal Cholinergic Function", Auton Autacoid Pharmacol., 26(3):219-33, (2006).
Ellis, J. et al., "Muscarinic and Nicotinic Receptors Synergistically Modulate Working Memory and Attention in Humans", Int J Neuropsychopharmacol., 9(2):175-89, (2006).
ENABLEX® darifenacin (Product Label) Prescribing Information, reference ID: 3102220, Warner Chilcott (US), LLC, Mar. 2012, 18 pages.
EP Patent Application No. 10802549; Supplementary European Search Report, dated Sep. 30, 2013; 3 pages.
Fogueri, L. et al., "Smart Polymers for Controlled Delivery of Proteins and Peptides: A Review of Patents", Recent Pat Drug Deliv Formul., 3(1):40-8, (2009).
Geyer, M., "Developing Translational Animal Models for Symptoms of Schizophrenia or Bipolar Manina", Neurotox Res., 14(1):71-8, (2008).
Gralewicz, S. et al., "Interaction of Chlorphenvinphos with Cholinergic Receptors in the Rabbit Hypothalamus", Neurotoxicol Teratol., 17(3):289-95, (1995).
Iconomopoulou, S. et al., "Incorporation of Small Molecular Weight Active Agents into Polymeric Components", Recent Pat Drug Deliv Formul., 2(2):94-107, (2008).
International Application No. PCT/US2010/002044; International Preliminary Report on Patentability, dated Jan. 24, 2012; 5 pages.
International Application No. PCT/US2010/002044; International Search Report and Written Opinion of the International Searching Authority, dated Sep. 2, 2010; 6 pages.
International Application No. PCT/US2019/053429; International Search Report and Written Opinion of the International Searching Authority, dated Dec. 4, 2019; 14 pages.
International Application No. PCT/US2020/060859; International Preliminary Report on Patentability, dated Jun. 2, 2022; 6 pages.
International Application No. PCT/US2020/060859; International Search Report and Written Opinion of the International Searching Authority, dated Feb. 26, 2021; 8 pages.
International Application No. PCT/US2022/017485; International Search Report and Written Opinion of the International Searching Authority, dated May 3, 2022; 10 pages.
Iwanaga, K. et al., "Carbachol Induces Ca2+-Dependent Contraction via Muscarinic M2 and M3 Receptors in Rat Intestinal Subepithelial Myofibroblasts", J Pharmacol Sci., 110(3):306-14, (2009).
Jones, C. et al., "Novel Selective Allosteric Activator of the M1 Muscarinic Acetylcholine Receptor Regulates Amyloid Processing and Produces Antipsychotic-Like Activity in Rats", J Neurosci., 28(41):10422-33, (2008).
Kahl, K. et al., "Therapie der Clozapin-Induzierten Hypersalivations Mit Botulinum-Toxin B", Nervenarzt, 76(2):205-8, (2005).
Kalantzi, L. et al., "Recent Advances in Oral Pulsatile Drug Delivery", Recent Pat Drug Deliv Formul., 3(1):49-63, (2009).

(56) References Cited

OTHER PUBLICATIONS

Karuna Therapeutics, Inc., Corporate Presentation, Aug. 2020; 40 pages.
Kreinin, A. et al., "Sulpiride Addition for the Treatment of Clozapine-Induced Hypersalivation: Preliminary Study", Isr J Pysch Relat Sci., 42(1):61-3, (2005).
Kurimoto, E. et al., "An Approach to Discovering Novel Muscarinic M1 Receptor Positive Allosteric Modulators with Potent Cognitive Improvement and Minimized Gastrointestinal Dysfunction", J Pharmacol Exp Ther., doi: 10.1124/jpet.117.243774. [Epub ahead of print] (2017).
Langmead, C. et al., "Muscarinic Acetylcholine Receptors as CNS Drug Targets", Pharmacol Ther., 117(2):232-43, (2008).
Li, Z. et al., "Effect of Muscarinic Receptor Agonists Xanomeline and Sabcomeline on Acetylcholine and Dopamine Efflux in the Rat Brain; Comparison with Effects of 4-[3-(4-butylpiperidin-1-yl)-propyl]-7 fluoro-4H-benzo[1,4]oxazin-3-one (AC260584) and N-desmethylclozapine", Eur J Pharmacol., 596(1-3):89-97, (2008).
Li, Z. et al., "Xanomeline Derivative EUK1001 Attenuates Alzheimer's Disease Pathology in Triple Transgenic Mouse Model", Mol Med Rep., 16(5):7835-40, (2017).
Liu, B. et al., "Design and Synthesis of N-[6-(Substituted Aminoethylideneamino)-2-Hydroxyindan-1-yl]arylamides As Selective and Potent Muscarinic M1 Agaonists", Bioorg Med Chem Lett., 25(19):4153-63, (2015).
Long, M. et al., "Discovery of a Novel 2,4-Dimethylquinoline-6-Carboxmide M4 Positive Allosteric Modulator (PAM) Chemotype via Scaffold Hopping", Bioorg Med Chem Lett., 27(22):4999-5001, (2017).
Luo, X. et al., "CHRM2 Gene Predisposes to Alcohol Dependence, Drug Dependence and Affective Disorders: Results From an Extended Case-Control Structured Association Study", Hum Mol Genet., 14(16):2421-34, (2005).
Material Safety Data Sheet—Lethal Nerve Agent Sarin, Appendix to the Riegle Report: US Chemical and Biological Warfare-Related Dual Use Exports to Iraq and Their Possible Impact on the Health Consequences of the Gulf War, U.S. Senate, 103d Congress, 2d Session, May 25, 1994, available at www.gulfweb.org/bigdoc/report/appbg/html (last visited Jun. 4, 2015).
Medina, A. et al., "Effects of Central Muscarinic-1 Receptor Stimulation on Blood Pressure Regulation", Hypertension, 29(3):828-34, (1997).
Messer Jr., W. et al., "Design and Development of Selective Muscarinic Agonists for the Treatment of Alzheimer's Disease: Characterization of Tetrahydropyrimidine Derivatives and Development of New Approaches for Improved Affinity and Selectivity for M1 Receptors", Pharm Acta Helv., 74(2-3):135-40, (2000).
Miller, A. et al., "Xanomeline Plus Tropsium: A Novel Strategy to Enhance Pro-Muscarinic Efficacy and Mitigate Peripheral Side Effects", Neuropsychopharmacology, 41:S230, (2016).
Mizrahi, B. et al., "Mucoadhesive Polymers for Delivery of Drugs to the Oral Cavity", Recent Pat Drug Deliv Formul., 2(2):108-19, (2008).
Mobascher, A. et al., "Association of a Variant in the Muscarinic Acetylcholine Receptor 2 Gene (CHRM2) with Nicotine Addiction", Am J Med Genet B Neuropsychiatr Genet., 153B(2):684-90, (2010).
Mortimer, A. et al., "Syptoms Rating Scales and Outcome in Schizophrenia", Br J Pysch., 191 (Suppl 50):s7-14, (2007).
Mouradian, M. et al., "No Response to High-Dose Muscarinic Agonist Therapy in Alzheimer's Disease", Neurology, 34(8):606-8, (1988).
National Library of Medicine (U.S.). (Dec. 2020) A Study to Assess Efficacy and Safety of KarXT in Acutely Psychotic Hospitalized Adult Patients With Schizophrenia (EMERGENT-2). Identifier NCT04659161. https://clinicaltrials.gov/ct2/show/NCT04659161.
National Library of Medicine (U.S.). (Dec. 2020) An Extension Study to Assess Long-term Safety, Tolerability, and Efficacy of KarXT in Adult Patients With Schizophrenia (EMERGENT-4). Identifier NCT04659174. https://clinicaltrials.gov/ct2/show/NCT04659174.
National Library of Medicine (U.S.). (Dec. 2021) A Study to Assess Efficacy and Safety of Adjunctive KarXT in Subjects With Inadequately Controlled Symptoms of Schizophrenia (ARISE). Identifier NCT05145413. https://clinicaltrials.gov/ct2/show/NCT05145413.
National Library of Medicine (U.S.). (Feb. 2021) A Study to Assess Efficacy and Safety of KarXT in Acutely Psychotic Hospitalized Adult Patients With Schizophrenia (EMERGENT-3). Identifier NCT04738123. https://clinicaltrials.gov/ct2/show/NCT04738123.
National Library of Medicine (U.S.). (Mar. 2021) An Open-label Study to Assess the Long-term Safety, Tolerability, and Efficacy of KarXT in Adult Patients With Schizophrenia (EMERGENT-5). Identifier NCT04820309. https://clinicaltrials.gov/ct2/show/NCT04820309.
National Library of Medicine (U.S.). (Mar. 2022) An Extension Study to Assess Long-Term Safety and Tolerability of Adjunctive KarXT in Subjects With Inadequately Controlled Symptoms of Schizophrenia. Identifier NCT05304767. https://clinicaltrials.gov/ct2/show/NCT05304767.
Nikam, S. et al., "Evolution of Schizophrenia Drugs: A Focus on Dopaminergic Systems", Curr Opin Investig Drugs, 9(1):37-46, (2008).
Paños, I. et al., "New Drug Delivery Systems Based on Chitosan", Curr Drug Discov Technol., 5(4):333-41, (2008).
Patel et al. Prediction of Relapse After Discontinuation of Antipsychotic Treatment in Alzheimer's Disease: The Role or Hallucinations. Am J Psychiatry. Nov. 18, 2016, vol. 174 (4). pp. 362-369, [retrieved on Apr. 15 2022J. Retrieved from the Internet: <URL: https://ajp.psychiatryonline.org/doi/pdf/10.1176/appi.ajp.2016.16020226>.
Praharaj, S. et al., "Is Clonidine Useful for Treatment of Clozpine-Induced Sialorrhea?", J Psychopharmacol., 19(5):426-8, (2005).
Raedler, T. et al., "In Vivo Determination of Muscarinic Acetylcholine Receptor Availability in Schizophrenia", Am J Psychiatry, 160(1):118-27, (2003).
Rogers, D. et al., "Therapeutic Options in the Treatment of Clozapine-Induced Sialorrhea", Pharmacother., 20(9):1092-5, (2000).
SANCTURA® trospium chloride (Product Label) Prescribing Information, reference ID: 3163014, Allergan, Inc., Jul. 2012, 17 pages.
Schneider, B. et al., "Reduction of Clozapine-Induced Hypersalivation by Pirenzepine is Safe", Pharmacopsychiatry, 37(2):43-5, (2004).
Schultz, S. et al., "Schizophrenia: A Review", Am Fam Physician, 75(12):1821-9, (2007).
Shannon, H. et al., "Xanomeline, an M1/M4 Preferring Muscarinic Cholinergic Receptor Agonist, Produces Antipsychotic-Like Activity in Rats and Mice", Schizophrenia Res., 42(3):249-59, (2000).
Shekhar, A. et al., "Selective Muscarinic Receptor Agonist Xanomeline as a Novel Treatment Approach for Schizophrenia", Am J Psychiatry, 165(8):1033-9, (2008).
Shirey, J. et al., "An Allosteric Potentiator of M4 mAChR Modulates Hippocampal Synaptic Transmission", Nature Chem Biol., 4(1):42-50, (2008).
Si, W. et al., "A Novel Derivative of Xanomeline Improves Fear Cognition in Aged Mice", Neurosci Lett., 473(2):115-9, (2010).
Soukup, O. et al., "Acetylcholinesterase Inhibitors and Drugs Acting on Muscarinic Receptors-Potential Crosstalk of Cholinergic Mechanisms During Pharmacological Treatment", Curr Neuropharmacol., 15(4):637-53, (2017).
Sramek, J. et al., "The Safety and Tolerance of Xenomeline Tartrate in Patients with Alzheimer's Disease", J Clin Pharmacol., 35(8):800-6, (1995).
Syed, R. et al., "Pharmacological Inventions for Clozapine-Induced Hypersalivation", Cochrane Database Sys Rev., 3:1-62, (2008).
Tao, G. et al., "Pharmaceutics", Yanbian University Press, 1st edition, 1st print, pp. 108-110, (2017).
Tarr, J. et al., "Challenges in the Development of an M4 PAM Preclinical Candidate: The Discovery, SAR, and In Vivo Characterization of a Series of 3-Aminoazetidine-Derived Amides", Bioorg Med Chem Lett., 27(13):2990-5, (2017).
U.S. Appl. No. 14/534,698; Non-Final Office Action, dated Nov. 24, 2015; 11 pages.

(56) References Cited

OTHER PUBLICATIONS

U.S. Appl. No. 15/378,796; Applicant-Initiated Interview Summary, dated Jul. 30, 2018, 3 pages.
U.S. Appl. No. 15/378,796; Applicant-Initiated Interview Summary, dated Jun. 12, 2018; 4 pages.
U.S. Appl. No. 15/378,796; Final Office Action, dated Jan. 4, 2018; 14 pages.
U.S. Appl. No. 15/378,796; Non-Final Office Action, dated May 24, 2017; 11 pages.
U.S. Appl. No. 15/400,108; Applicant-Initiated Interview Summary, dated Jun. 12, 2018; 3 pages.
U.S. Appl. No. 15/400,108; Applicant-Initiated Interview Summary, dated Oct. 12, 2018; 3 pages.
U.S. Appl. No. 15/400,108; Final Office Action, dated Jul. 18, 2017; 14 pages.
U.S. Appl. No. 15/400,108; Non-Final Office Action, dated Feb. 24, 2017; 11 pages.
U.S. Appl. No. 15/400,108; Non-Final Office Action, dated Sep. 7, 2018; 43 pages.
U.S. Appl. No. 15/400,108; Notice of Allowance, dated Nov. 8, 2018; 23 pages.
U.S. Appl. No. 15/400,108; Notice of Appeal, dated Jan. 17, 2018; 1 page.
U.S. Appl. No. 15/738,796; Applicant-Initiated Interview Summary, dated Apr. 2, 2019; 3 pages.
U.S. Appl. No. 15/738,796; Applicant-Initiated Interview Summary, dated Mar. 4, 2019; 3 pages.
U.S. Appl. No. 15/738,796; Notice of Allowance, dated Sep. 6, 2018; 15 pages.
U.S. Appl. No. 16/270,206; Applicant-Initiated Interview Summary, dated May 9, 2019; 7 pages.
U.S. Appl. No. 16/270,206; Applicant-Initiated Interview Summary, dated May 24, 2019; 3 pages.
U.S. Appl. No. 16/270,206; Non-Final Office Action, dated Apr. 16, 2019; 28 pages.
U.S. Appl. No. 16/270,206; Notice of Allowance, dated Jun. 12, 2019; 28 pages.
U.S. Appl. No. 16/289,165; Applicant-Initiated Interview Summary, dated Apr. 2, 2019; 3 pages.
U.S. Appl. No. 16/289,165; Applicant-Initiated Interview Summary, dated May 9, 2019; 6 pages.
U.S. Appl. No. 16/289,165; Applicant-Initiated Interview Summary, dated May 24, 2019; 4 pages.
U.S. Appl. No. 16/289,165; Non-Final Office Action, dated Apr. 11, 2019; 29 pages.
U.S. Appl. No. 16/289,165; Notice of Allowance, dated Jun. 13, 2019; 27 pages.
U.S. Appl. No. 16/444,206; Non-Final Office Action, dated Nov. 8, 2019; pages.
U.S. Appl. No. 16/444,206; Notice of Allowance, dated Feb. 27, 2020; 13 pages.
U.S. Appl. No. 16/585,532; Non-Final Office Action, dated Aug. 5, 2020; 39 pages.
U.S. Appl. No. 16/585,532; Non-Final Office Action, dated Oct. 6, 2020; 7 pages.
U.S. Appl. No. 16/585,532; Notice of Allowance, dated Jan. 7, 2021; 10 pages.
U.S. Appl. No. 16/880,600; Non-Final Office Action, dated Aug. 5, 2020; 20 pages.
U.S. Appl. No. 16/880,600; Non-Final Office Action, dated Nov. 5, 2020; 13 pages.
U.S. Appl. No. 16/880,600; Notice of Allowance, dated Jan. 12, 2021; 9 pages.
U.S. Appl. No. 16/880,634; Applicant-Initiated Interview Summary, dated Jan. 19, 2022; 2 pages.
U.S. Appl. No. 16/880,634; Final Office Action, dated May 27, 2021; 30 pages.
U.S. Appl. No. 16/880,634; Non-Final Office Action, dated Jan. 1, 2021; 39 pages.
U.S. Appl. No. 16/880,634; Non-Final Office Action, dated Nov. 18, 2021; 27 pages.
U.S. Appl. No. 16/950,203; Non-Final Office Action, dated Feb. 16, 2022; 31 pages.
U.S. Appl. No. 17/143,904; Non-Final Office Action, dated Feb. 17, 2022; 23 pages.
U.S. Appl. No. 17/143,904; Notice of Allowance, dated Jun. 30, 2022; 8 pages.
U.S. Appl. No. 17/167,714; Final Office Action, dated Apr. 26, 2022; 12 pages.
U.S. Appl. No. 17/167,714; Non-Final Office Action, dated Apr. 15, 2021; 23 pages.
U.S. Appl. No. 17/663,760; Application as filed, dated May 17, 2022; 43 pages.
Vardigan, J. et al., "Improved Cognition Without Adverse Effects: Novel M1 Muscarinic Potentiator Compares Favorably to Donepezil and Xanomeline in Rhesus Monkey", Psychopharmacol., 232(11):1859-66, (2015).
Wan, W. et al., "Use of Degradable and Nondegradable Nanomaterials for Controlled Release", Nanomed., 2(4):483-509, (2007).
Witte, L. et al., "Muscarinic Receptor Antoagonists for Overactive Bladder Treatment: Does One Fit All?", Curr Opin Urol., 19(1):13-9, (2009).
Wood, M. et al., "Discovery of VU0467485/AZ13713945: An M4 PAM Evaluated as a Preclinical Candidate for the Treatment of Schizophrenia", ACS Med Chem Lett., 8(2):233-8, (2017).

\* cited by examiner

Stability protocol for Xanomeline / Trospuim HCl Pellets

Manufacturing date: 2016DE12, Incubation date: 2016DE16

| Project | Lot (Strength) | Packaging | Stability conditions | | | | Time points (month) | | | | |
|---|---|---|---|---|---|---|---|---|---|---|---|
| | | | 25°C/ 60% RH | 30°C/ 65% RH | 40°C/ 75% RH | 0 | 1 | 2 | 3 | 6 | EXTRA |
| 286-02 | Xanomeline 50mg (fb) Trospuim HCl 20mg | 30cc HDPE bottles with sealed PP cap | 6 bottles (20 capsules/bottle) | | | 2016DE16 | 2017JA16 | 2017FE16 | 2017MR16 | 2017JN16 | TBD |
| | | | | 6 bottles (20 capsules/bottle) | | | 2017JA16 | 2017FE16 | 2017MR16 | 2017JN16 | TBD |
| | | | | | 4 bottles (20 capsules/bottle) | | 2017JA16 | 2017FE16 | 2017MR16 | 2017JN16 | TBD |
| | Xanomeline 50mg (fb) Trospuim HCl 10mg | | 5 bottles (20 capsules/bottle) | | | | 2017JA16 | 2017FE16 | 2017MR16 | 2017JN16 | TBD |
| | | | | 6 bottles (20 capsules/bottle) | | | 2017JA16 | 2017FE16 | 2017MR16 | 2017JN16 | TBD |
| | | | | | 3 bottles (20 capsules/bottle) | | 2017JA16 | 2017FE16 | 2017MR16 | 2017JN16 | TBD |

Sample to be analyzed for:
Appearance, Assay, Related Substances, KF and Dissolution
At the Client request, sample will be removed from chamber and analyzed.

FIG 1

| STORAGE | | T=0 | 25°C/60%RH | | |
|---|---|---|---|---|---|
| TEST DESCRIPTION | | Release, Rev 0 | 3 Months Stability, Rev 01 | 6 Months Stability, Rev 01 | 9 Months Stability, Rev 01 |
| SPECIFICATION used at time of analysis | | | | | |
| Conforms to acceptance criteria (Y/N) | | Y | Y | Y | Y |
| Description (Visual) | | Off-white opaque hard shell capsule with no markings | No change as compared to initials | No change as compared to initials | No change as compared to initials |
| Water content by KF (USP <921>, Method 1a) (n=3) | %w/w | 2.4 | 2.8 | 2.5 | 2.1 |
| Assay (Corealis-286602-AO-01) (n=2) | % label claim Xanomeline | 104.5 c | 99.8 | 102.3 | 102.3 |
| | mg Xanomeline/capsule | 52.3 c | 49.9 | 51.2 | 51.2 |
| | % label claim Trospium Chloride | 97.5 c | 97.7 | 99.8 | 97.8 |
| | mg Trospium Chloride/capsule | 9.8 a | 9.8 | 10.0 | 9.8 |
| | Method Revision | 0 | 01 | 02 | 03 |
| | Trospium Chloride related compound B | Not detected a | Not detected | Not detected | Not detected |
| | Trospium Chloride related compound A | Not detected a | <0.1 | Not detected | Not detected |
| Related substances (%LC) a,b (Corealis-286602-AO-01) (n=2) | Unspecified Impurity (Xanomeline_RRT0.20) c,f | 0.15 c | 0.14 | 0.14 | 0.14 |
| | Unspecified Impurity (Xanomeline_RRT1.09) c,f | - | 0.18 | 0.16 | 0.24 |
| | Total Impurities | 0.15 c | 0.32 d | 0.30 | 0.37 |
| | Method Revision | 0 | 01 | 02 | 03 |

FIG. 6

| STORAGE | | T=0 | 30°C/65%RH | |
|---|---|---|---|---|
| TEST DESCRIPTION | | | 3 Months | 6 Months |
| SPECIFICATION used at time of analysis | | Release, Rev 0 | Stability, Rev 01 | Stability, Rev 01 |
| Conforms to acceptance criteria (Y/N) | | Y | Y | Y |
| Description (Visual) | | Off-white opaque hard shell capsule with no markings | No change as compared to initials | No change as compared to initials |
| Water content by KF (USP <921>, Method 1a) (n=3) | %w/w | 2.4 | 2.5 | 2.7 |
| Assay (Corsello-28602-AO-01) (n=2) | % label claim Xanomeline | 104.5 c | 100.8 | 102.3 |
| | mg Xanomeline/capsule | 52.3 c | 50.3 | 51.2 |
| | % label claim Trospium Chloride | 97.5 c | 98.4 | 98.0 |
| | mg Trospium Chloride/capsule | 9.8 c | 9.8 | 9.8 |
| | Method Revision | 0 | 01 | 02 |
| Related substances (%LC) (Corsello-28602-AO-01) (n=2) | Trospium Chloride related compound B | Not detected c | Not detected | Not detected |
| | Trospium Chloride related compound A | Not detected c | Not detected | Not detected |
| | Unspecified Impurity (Xanomeline_RRT 0.34) c,f | 0.15 c | 0.14 | 0.14 |
| | Unspecified Impurity (Xanomeline_RRT 1.08) c,f | - | 0.16 | 0.19 |
| | Total Impurities | 0.15 c | 0.30 | 0.33 |
| | Method Revision | 0 | 01 | 02 |

FIG. 7

| STORAGE | | T=0 | 3 Months | 40°C/75%RH | 6 Months |
|---|---|---|---|---|---|
| TEST DESCRIPTION | | Release, Rev 0 | Stability, Rev 01 | | Stability, Rev 01 |
| SPECIFICATION used at time of analysis | | | | | |
| Conforms to acceptance criteria (Y/N) | | Y | Y | Y | Y |
| Description | | Off-white opaque hard shell capsule with no markings | No change as compared to initials | No change as compared to initials | No change as compared to initials |
| Water content by KF (USP <921>, Method 1a) (n=3) | %w/w | 2.4 | | 2.5 | 2.9 |
| Assay (Consalia-28602-AQ-01) (n=2) | % label claim Xanomeline | 104.5 ᶜ | | 99.3 | 101.7 |
| | mg Xanomeline/capsule | 52.3 ᶜ | | 49.6 | 50.9 |
| | % label claim Trospium Chloride | 97.5 ᶜ | | 97.0 | 100.4 |
| | mg Trospium Chloride/capsule | 9.8 ᶜ | | 9.7 | 10.0 |
| | Method Revision | 0 | | 01 | 02 |
| Related substances (HPLC) ᵃ (Consalia-28602-AQ-01) (n=2) | Trospium Chloride related compound B | Not detected ᶜ | Not detected | Not detected | Not detected |
| | Trospium Chloride related compound A | Not detected ᶜ | Not detected | | 0.19 |
| | Unspecified Impurity (Xanomeline_RRT 0.24) ᵃ,³ | 0.15 ᶜ | | 0.14 | 0.14 |
| | Unspecified Impurity (Xanomeline_RRT 1.09) ᵃ,³ | — | | 0.14 | 0.22 |
| | Total Impurities | 0.15 ᶜ | | 0.28 | 0.55 |
| | Method Revision | 0 | | 01 | 02 |

FIG. 8

| STORAGE | T=0 | | 3 Months | | 6 Months | | 9 Months | |
|---|---|---|---|---|---|---|---|---|
| TEST DESCRIPTION | Release, Rev 0 | | Stability, Rev 01 | | Stability, Rev 01 | | Stability, Rev 01 | |
| SPECIFICATION used at time of analysis | | | | | 25°C/60%RH | | | |
| Conforms to acceptance criteria (Y/N) | Y | | Y | | Y | | Y | |
| | %LC | Range | %LC | Range | %LC[a] | Range[a] | %LC | Range |
| Xanomeline Time (min.) | | | | | | | | |
| 10 | 34 | 12-69 | 30 | 7-67 | 34 | 1-74 | 47 | 26-82 |
| 20 | 88 | 90-102 | 85 | 75-97 | 89 | 62-101 | 96 | 85-102 |
| (Q=80%) 30 | 103 | 102-104 | 100 | 98-101 | 99 | 87-102 | 101 | 95-103 |
| 45 | 103 | 103-104 | 102 | 101-103 | 102 | 96-103 | 101 | 101-102 |
| Trospium Chloride Time (min.) | %LC | Range | %LC | Range | %LC[a] | Range[a] | %LC | Range |
| 10 | 49 | 11-83 | 27 | 6-60 | 32 | 0-65 | 43 | 22-63 |
| 20 | 93 | 87-98 | 86 | 75-98 | 86 | 86-97 | 96 | 86-103 |
| (Q=80%) 30 | 96 | 94-102 | 97 | 92-103 | 95 | 91-100 | 98 | 94-104 |
| 45 | 96 | 94-102 | 99 | 95-103 | 97 | 90-104 | 99 | 95-104 |
| Method Revision | 0 | | 01 | | 01 | | 01 | |
| Microbial Limits[b] USP<61>, <62> | | | | | | | | |
| Total Yeasts and Molds Counts (TYMC):≤100 cfu/g | <50 cfu/g | | N/A | | N/A | | N/A | |
| Total Aerobic Microbial Counts (TAMC): ≤1000 cfu/g | <500 cfu/g | | N/A | | N/A | | N/A | |
| Escherichia coli: Absent | Absent | | N/A | | N/A | | N/A | |

FIG. 9

| STORAGE | | | T = 0 | | 30°C/65%RH | | | |
|---|---|---|---|---|---|---|---|---|
| TEST DESCRIPTION | | | Release, Rev 0 | | 3 Months Stability, Rev 01 | | 6 Months Stability, Rev 01 | |
| SPECIFICATION used at time of analysis | | | | | | | | |
| Conforms to acceptance criteria (Y/N) | | | Y | | Y | | Y | |
| | Xanomeline | | %LC | Range | %LC | Range | %LC | Range |
| | Time (min.) | 10 | 54 | 12-89 | 35 | 14-59 | 35 | 3-64 |
| | | 20 | 98 | 90-102 | 85 | 89-96 | 97 | 89-103 |
| | (Q=80%) | 30 | 103 | 102-104 | 101 | 99-103 | 102 | 100-104 |
| | | 45 | 103 | 103-104 | 102 | 100-104 | 103 | 101-104 |
| | Trospium Chloride | | %LC | Range | %LC | Range | %LC | Range |
| | Time (min.) | 10 | 49 | 11-83 | 30 | 9-54 | 30 | 2-56 |
| | | 20 | 93 | 87-98 | 84 | 68-93 | 92 | 81-100 |
| | (Q=80%) | 30 | 98 | 94-102 | 96 | 94-102 | 97 | 93-105 |
| | | 45 | 96 | 94-102 | 99 | 95-102 | 97 | 93-105 |
| Dissolution (%LC) (Capsule-288x2-8-01) (n=6) (900 mL of 0.1N HCl, paddles at 50 rpm) | Method Reversion | | 0 | | 01 | | 01 | |
| Microbial Limits * USP <61>, <62> | Total Yeasts and Molds Counts (TYMC) ≤100 cfu/g | | <50 cfu/g | | N/A | | N/A | |
| | Total Aerobic Microbial Counts (TAMC) ≤1000 cfu/g | | < 500 cfu/g | | N/A | | N/A | |
| | Escherichia coli: Absent | | Absent | | N/A | | N/A | |

FIG. 10

| STORAGE | | T = 0 | | 40°C/75%RH | | | |
|---|---|---|---|---|---|---|---|
| TEST DESCRIPTION | | Release, Rev 0 | | 3 Months Stability, Rev 01 | | 6 Months Stability, Rev 01 | |
| SPECIFICATION used at time of analysis | | %LC | Range | %LC | Range | %LC | Range |
| Conforms to acceptance criteria (Y/N) | | Y | | Y | | Y | |
| Dissolution (%LC) (Contents-08632-8-01) (n=6) (900 mL of 0.1 N HCl, paddles at 50rpm) | Xanometine Time (min.) | | | | | | |
| | 10 | 54 | 12-89 | 45 | 6-90 | 45 | 17-71 |
| | 20 | 98 | 90-102 | 89 | 80-99 | 89 | 71-101 |
| | (Q=80%) 30 | 103 | 102-104 | 98 | 93-101 | 97 | 93-101 |
| | 45 | 103 | 103-104 | 100 | 98-101 | 98 | 97-101 |
| | Trospium Chloride Time (min.) | | | | | | |
| | 10 | 49 | 11-80 | 42 | 3-85 | 40 | 17-71 |
| | 20 | 93 | 87-98 | 86 | 74-94 | 87 | 75-96 |
| | (Q=80%) 30 | 98 | 94-102 | 95 | 87-101 | 95 | 91-99 |
| | 45 | 98 | 94-102 | 97 | 92-103 | 97 | 93-100 |
| Method Revision | | 0 | | 01 | | 01 | |
| Microbial Limits[a] USP <61>, <62> | Total Yeasts and Molds Counts (TYMC) ≤100 cfu/g | <50 cfu/g | | N/A | | N/A | |
| | Total Aerobic Microbial Counts (TAMC) ≤1000 cfu/g | < 500 cfu/g | | N/A | | N/A | |
| | Escherichia coli: Absent | Absent | | N/A | | N/A | |

FIG. 11

Xanomeline API Related Substances Profile for Xanomeline/Trospium Cl 50/10 mg Capsules

| Stability time point | | Initials | T = 3 months | T = 6 months | T = 9 months |
|---|---|---|---|---|---|
| Related Substances (%w/w) (n=1) (Corealis-28602-AD-01) | Unspecified impurity (RRT 0.23) | 0.14 | 0.14 | 0.14 | 0.14 |
| | Unspecified impurity (RRT 1.09) | <0.1 | 0.16 | 0.14 | 0.16 |
| | Method Revision | 0 | 01 | 02 | 03 |

FIG. 12

Trospium Chloride API Related Substances Profile for Xanomeline/Trospium Cl 50/10 mg Capsules

| Stability time point | | Initials | T = 3 months | T = 6 months | T = 9 months |
|---|---|---|---|---|---|
| Related Substances (%w/w) (n=1) (Corealis-28602-AD-01) | Unspecified impurity | Not Detected | Not Detected | Not Detected | Not Detected |
| | Method Revision | 0 | 01 | 02 | 03 |

FIG. 13

Specification for Xanomeline/Trospium Cl 50/10 mg Capsules

| TEST DESCRIPTION | ACCEPTANCE CRITERIA Release, Rev 0 | ACCEPTANCE CRITERIA Stability, Rev 01 |
|---|---|---|
| Description (Visual) | White to off-white opaque hard shell capsule with no markings | White to off-white opaque hard shell capsule with no markings |
| Water Content by KF (USP <921>, Method 1a) | Report result | Report results |
| Assay (%LC) (Corealis-28602-AD) | Xanomeline: 90 – 110% label claim (45 – 55 mg Xanomeline/capsule) Trospium Chloride: 90 – 110% label claim (9 – 11mg Trospium Chloride/capsule) | Xanomeline: 90 – 110% label claim (45 – 55 mg Xanomeline/capsule) Trospium Chloride: 90 – 110% label claim (9 – 11mg Trospium Chloride/capsule) |
| Related Substances (%LC)^A (Corealis-28602-AD) | Trospium Chloride related compound B: NMT 0.2%LC Trospium Chloride related compound A: NMT 0.2%LC Any single unspecified impurity: NMT 0.2%LC Total Impurities: NMT 1.5%LC | Trospium Chloride related compound B: NMT 0.2%LC Trospium Chloride related compound A: NMT 0.2%LC Any single unspecified impurity: NMT 0.2%LC Total Impurities: NMT 1.5%LC |
| Dissolution (Corealis-28602-B) | Xanomeline: NLT 80% (Q) of labeled amount of Xanomeline is dissolved at 30 minutes. Report profile Trospium Chloride: NLT 80% (Q) of labeled amount of Trospium Chloride is dissolved at 30 minutes. Report profile | Xanomeline: NLT 80% (Q) of labeled amount of Xanomeline is dissolved at 30 minutes. Report profile Trospium Chloride: NLT 80% (Q) of labeled amount of Trospium Chloride is dissolved at 30 minutes. Report profile |
| Microbial Limits^B USP<61>, <62> | Total Yeasts and Molds Counts (TYMC): ≤100 cfu/g Total Aerobic Microbial Counts (TAMC): ≤1000 cfu/g Escherichia coli: Absent | Total Yeasts and Molds Counts (TYMC): ≤100 cfu/g Total Aerobic Microbial Counts (TAMC): ≤1000 cfu/g Escherichia coli: Absent |

FIG. 14

| STORAGE | | T=0 | 3 months | 25°C/60%RH 6 months |
|---|---|---|---|---|
| TEST DESCRIPTION | | | | |
| SPECIFICATION used at time of analysis | | Stability, Rev 0 | Stability, Rev 0 | Stability, Rev 0 |
| Conforms to acceptance criteria (Y/N) | | Y | Y | Y |
| Description (Visual) | | Off-white opaque hard shell capsule with no markings | No change as compared to initials | No change as compared to initials |
| Water content by KF (USP <921>, Method 1a) (n=3) | %w/w | 2.9 | 2.7 | 3.0 |
| Assay (Corealis-28602-AD-01) (n=2) | % label claim Xanomeline | 101.8 | 101.9 | 102.2 |
| | mg Xanomeline/capsule | 50.9 | 51.0 | 51.1 |
| | % label claim Trospium Chloride | 98.3 | 98.2 | 98.3 |
| | mg Trospium Chloride/capsule | 19.7 | 19.6 | 19.7 |
| | Method Revision | 01 | 02 | 03 |
| Related substances (HLC)[4] (Corealis-28602-AD-01) (n=2) | Trospium Chloride related compound B | Not detected | Not detected | Not detected |
| | Trospium Chloride related compound A | Not detected | Not detected | Not detected |
| | Unspecified Impurity (Xanomeline_RRT0.23) c.8 | 0.13 | 0.14 | 0.14 |
| | Unspecified Impurity (Xanomeline_RRT1.00) c.8 | 0.17 | 0.14 | 0.20 |
| | Total Impurities | 0.30 | 0.28 | 0.34 |
| | Method Revision | 01 | 02 | 03 |

FIG. 15

| STORAGE | | T = 0 | 30°C/65%RH 6 months |
|---|---|---|---|
| TEST DESCRIPTION | | Stability, Rev 0 | Stability, Rev 0 |
| SPECIFICATION used at time of analysis | | | |
| Conforms to acceptance criteria (Y/N) | | Y | Y |
| Description (Visual) | | Off-white opaque hard shell capsule with no markings | No change as compared to initials |
| Water content by KF (USP <921>, Method 1a) (n=3) | %w/w | 2.9 | 3.0 |
| Assay (Centralis-28602-AD-01) (n=2) | % label claim Xanomeline | 101.8 | 101.5 |
| | mg Xanomeline/capsule | 50.9 | 50.8 |
| | % label claim Trospium Chloride | 98.3 | 96.4 |
| | mg Trospium Chloride/capsule | 19.7 | 19.3 |
| | Method Revision | 01 | 03 |
| Related substances (%LC) [a] (Centralis-28602-AD-01) (n=2) | Trospium Chloride related compound B | Not detected | Not detected |
| | Trospium Chloride related compound A | Not detected | Not detected |
| | Unspecified Impurity (Xanomeline_RRT 0.23) [b,c] | 0.13 | 0.14 |
| | Unspecified Impurity (Xanomeline_RRT 1.09) [b,c] | 0.17 | 0.23 |
| | Total Impurities | 0.30 | 0.37 |
| | Method Revision | 01 | 03 |

FIG. 16

| STORAGE | | T=0 | 40°C/75%RH | |
|---|---|---|---|---|
| TEST DESCRIPTION | | | 3 months | 6 months |
| SPECIFICATION used at time of analysis | | Stability, Rev 0 | Stability, Rev 0 | Stability, Rev 0 |
| Conforms to acceptance criteria (Y/N) | | Y | Y | N |
| Description (Visual) | | Off-white opaque hard shell capsule with no markings | No change as compared to initials | No change as compared to initials |
| Water content by KF (USP <921>, Method 1a) (n=3) | %w/w | 2.9 | 2.9 | 3.1 |
| Assay (Capsule-28902-AO-01) (n=2) | % label claim Xanomeline | 101.8 | 101.8 | 100.9 |
| | mg Xanomeline/capsule | 50.9 | 50.9 | 50.5 |
| | % label claim Trospium Chloride | 98.3 | 98.1 | 96.2 |
| | mg Trospium Chloride/capsule | 19.7 | 19.6 | 19.2 |
| | Method Revision | 01 | 02 | 03 |
| | Trospium Chloride related compound B | Not detected | Not detected | Not detected |
| | Trospium Chloride related compound A | Not detected | <0.1 | 0.14 |
| Related substances (HLC)^A (Capsule-28902-AO-01) (n=2) | Unspecified Impurity (Xanomeline_RRT 0.23)^c,b | 0.13 | 0.14 | 0.14 |
| | Unspecified Impurity (Xanomeline_RRT 1.09)^c,b | 0.17 | 0.20 | 0.26^d |
| | Total Impurities | 0.30 | 0.33 | 0.54 |
| | Method Revision | 01 | 02 | 03 |

FIG. 17

| STORAGE | | T = 0 | | 25°C/60%RH | | 25°C/60%RH | |
|---|---|---|---|---|---|---|---|
| TEST DESCRIPTION | | | | 3 months | | 6 months | |
| SPECIFICATION used at time of analysis | | Stability, Rev 0 | | Stability, Rev 0 | | Stability, Rev 0 | |
| Conforms to acceptance criteria (Y/N) | | Y | | Y | | Y | |
| | | %LC | Range | %LC | Range | %LC | Range |
| Dissolution (HLC) (Capsule-28602-B-01) (n=6) (900 mL of 0.1 N HCl, paddles at 50 rpm) | Xanomeline Time (min.) | | | | | | |
| | 10 | 34 | 0-66 | 27 | 11-46 | 29 | 0-71 |
| | 20 | 89 | 64-97 | 84 | 85-101 | 77 | 66-97 |
| | (Q=80%) 30 | 100 | 88-105 | 102 | 99-105 | 98 | 88-102 |
| | 45 | 103 | 99-106 | 103 | 99-105 | 102 | 99-107 |
| | Trospium Chloride Time (min.) | %LC | Range | %LC | Range | %LC | Range |
| | 10 | 30 | 0-63 | 26 | 11-43 | 29 | 0-66 |
| | 20 | 86 | 70-95 | 90 | 83-93 | 75 | 62-92 |
| | (Q=80%) 30 | 97 | 91-103 | 96 | 94-99 | 94 | 87-99 |
| | 45 | 100 | 97-103 | 97 | 94-100 | 98 | 95-101 |
| | Method Revision | 01 | | 01 | | 01 | |
| Microbial Limits a USP <61>, <62> | Total Yeasts and Molds Counts (TYMC): ≤100 cfu/g | <50 cfu/g | | N/A | | N/A | |
| | Total Aerobic Microbial Counts (TAMC): ≤1000 cfu/g | < 500 cfu/g | | N/A | | N/A | |
| | Escherichia coli: Absent | Absent | | N/A | | N/A | |

FIG. 18

| STORAGE | | T=0 | | | 30°C/65%RH 6 months | | |
|---|---|---|---|---|---|---|---|
| TEST DESCRIPTION | | Stability, Rev 0 | | | Stability, Rev 0 | | |
| SPECIFICATION used at time of analysis | | Y | | | Y | | |
| Conforms to acceptance criteria (Y/N) | | | | | | | |
| Dissolution (%LC) (Corealis-28602-B-01) (n=6) (900 mL of 0.1N HCl, paddles at 50 rpm) | Xanomeline Time (min.) | | %LC | Range | | %LC | Range |
| | 10 | | 34 | 0-66 | | 27 | 0-48 |
| | 20 | | 89 | 64-97 | | 78 | 60-99 |
| | (Q=80%) 30 | | 100 | 88-105 | | 94 | 85-103 |
| | 45 | | 103 | 99-106 | | 98 | 91-103 |
| | Trospium Chloride Time (min.) | | %LC | Range | | %LC | Range |
| | 10 | | 30 | 0-63 | | 29 | 0-49 |
| | 20 | | 86 | 70-95 | | 80 | 65-101 |
| | (Q=80%) 30 | | 97 | 91-103 | | 95 | 91-103 |
| | 45 | | 100 | 97-103 | | 99 | 95-103 |
| | Method Revision | | | 01 | | | 01 |
| Microbial Limits[B] USP<61>, <62> | Total Yeasts and Molds Counts (TYMC): ≤100 cfu/g | | | ≤50 cfu/g | | | N/A |
| | Total Aerobic Microbial Counts (TAMC): ≤1000 cfu/g | | | < 500 cfu/g | | | N/A |
| | Escherichia coli: Absent | | | Absent | | | N/A |

FIG. 19

| STORAGE | | | T = 0 | | | 3 months | | | 6 months | | |
|---|---|---|---|---|---|---|---|---|---|---|---|
| TEST DESCRIPTION | | | | | | 40°C/75%RH | | | 40°C/75%RH | | |
| SPECIFICATION used at time of analysis | | | Stability, Rev 0 | | | Stability, Rev 0 | | | Stability, Rev 0 | | |
| Conforms to acceptance criteria (Y/N) | | | Y | | | Y | | | N | | |
| | | Time (min.) | %LC | | Range | %LC | | Range | %LC | | Range |
| | Xanomeline | 10 | 34 | | 0-66 | 27 | | 3-58 | 32 | | 10-56 |
| | | 20 | 89 | | 64-97 | 89 | | 70-99 | 94 | | 75-101 |
| | | (Q=80%) 30 | 100 | | 88-105 | 97 | | 87-103 | 99 | | 93-102 |
| | | 45 | 103 | | 99-106 | 99 | | 95-103 | 100 | | 97-102 |
| Dissolution (%LC) (Corsalis-2802-B-01) (n=6) (900 mL of 0.1N HCl, paddles at 50 rpm) | | Time (min.) | %LC | | Range | %LC | | Range | %LC | | Range |
| | Trospium Chloride | 10 | 30 | | 0-63 | 26 | | 2-59 | 28 | | 8-45 |
| | | 20 | 86 | | 70-95 | 88 | | 75-96 | 93 | | 79-98 |
| | | (Q=80%) 30 | 97 | | 91-103 | 94 | | 87-98 | 98 | | 96-100 |
| | | 45 | 100 | | 97-103 | 96 | | 92-98 | 99 | | 98-101 |
| | | Method Revision | 01 | | | 01 | | | 01 | | |
| Microbial Limits* USP <61>, <62> | Total Yeasts and Molds Counts (TYMC): ≤100 cfu/g | | <50 cfu/g | | | N/A | | | N/A | | |
| | Total Aerobic Microbial Counts (TAMC): ≤1000 cfu/g | | < 500 cfu/g | | | N/A | | | N/A | | |
| | Escherichia coli: Absent | | Absent | | | N/A | | | N/A | | |

FIG. 20

Xanomeline API Related Substances Profile for Xanomeline/Trospium Cl 50/20 mg Capsules

| Stability time point | | Initials | T= 3 months | T= 6 months |
|---|---|---|---|---|
| Related Substances (%w/w) (n=1) (Corealis-28602-AD-01) | Unspecified impurity (RRT 0.24) | 0.14 | 0.14 | 0.14 |
| | Unspecified impurity (RRT 1.09) | 0.20 | 0.14 | 0.18 |
| | Method Revision | 01 | 02 | 03 |

FIG. 21

Trospium Chloride API Related Substances Profile for Xanomeline/Trospium Cl 50/20 mg Capsules

| Stability time point | | Initials | T= 3 months | T= 6 months |
|---|---|---|---|---|
| Related Substances (%w/w) (n=1) (Corealis-28602-AD-01) | Unspecified impurity | Not Detected | Not Detected | Not Detected |
| | Method Revision | 01 | 02 | 03 |

FIG. 22

Specification for Xanomeline/Trospium Cl 50/20 mg Capsules

| TEST DESCRIPTION | ACCEPTANCE CRITERIA Stability, Rev 0 |
|---|---|
| Description (Visual) | White to off-white opaque hard shell capsule with no markings |
| Water Content by KF (USP <921>, Method 1a) | Report result |
| Assay (%LC) (Corealis-28602-AD) | Xanomeline: 90 - 110% label claim (45 – 55 mg Xanomeline/capsule) |
| | Trospium Chloride: 90 - 110% label claim (18 – 22mg Trospium Chloride/capsule) |
| Related Substances (%LC)* (Corealis-28602-AD) | Trospium Chloride related compound B: NMT 0.2%LC |
| | Trospium Chloride related compound A: NMT 0.2%LC |
| | Any single unspecified Impurity: NMT 0.2%LC |
| | Total Impurities: NMT 1.5%LC |
| Dissolution (Corealis-28602-B) | Xanomeline: NLT 80% (Q) of labeled amount of Xanomeline is dissolved at 30 minutes. Report profile |
| | Trospium Chloride: NLT 80% (Q) of labeled amount of Trospium Chloride is dissolved at 30 minutes. Report profile |
| Microbial Limits * USP<61>, <62> | Total Yeasts and Molds Counts (TYMC): ≤100 cfu/g |
| | Total Aerobic Microbial Counts (TAMC): ≤1000 cfu/g |
| | Escherichia coli: Absent |

FIG. 23

| STORAGE | | | T = 0 | 25°C/60%RH | |
|---|---|---|---|---|---|
| | | | | 3 months | 6 months |
| TEST DESCRIPTION | | | | | |
| SPECIFICATION used at time of analysis | | | Stability, Rev 0 | Stability, Rev 0 | Stability, Rev 0 |
| Conforms to acceptance criteria (Y/N) | | | Y | Y | Y |
| Description (Visual) | | | Off-white opaque hard shell capsule with no markings | No change as compared to initials | No change as compared to initials |
| Water content by KF (USP <921>, Method 1a) (n=3) | | %w/w | 2.4 | 2.3 | 1.8 |
| Assay (Corealis-28602-AD-01) (n=2) | | % label claim Xanomeline | 102.0 | 104.6 | 103.7 |
| | | mg Xanomeline/capsule | 76.5 | 78.4 | 77.8 |
| | | % label claim Trospium Chloride | 95.9 | 99.7 | 97.9 |
| | | mg Trospium Chloride/capsule | 9.6 | 9.9 | 9.8 |
| | | Method Revision | 01 | 02 | 03 |
| Related substances (NLG)[A] (Corealis-28602-AD-01) (n=2) | | Trospium Chloride related compound B | Not detected | Not detected | Not detected |
| | | Trospium Chloride related compound A | Not detected | Not detected | Not detected |
| | | Unspecified impurity (Xanomeline_RRT0.24)[c,b] | 0.15 | 0.14 | 0.14 |
| | | Unspecified impurity (Xanomeline_RRT1.10)[c,b] | 0.15 | 0.13 | 0.20 |
| | | Total impurities | 0.30 | 0.27 | 0.34 |
| | | Method Revision | 01 | 02 | 03 |

FIG. 24

| STORAGE | | T=0 | 30°C/65%RH 6 months |
|---|---|---|---|
| TEST DESCRIPTION | | | |
| SPECIFICATION used at time of analysis | | Stability, Rev 0 | Stability, Rev 0 |
| Conforms to acceptance criteria (Y/N) | | Y | Y |
| Description (Visual) | | Off-white opaque hard shell capsule with no markings | No change as compared to initials |
| Water content by KF (USP <921>, Method 1a) (n=3) | %w/w | 2.4 | 2.2 |
| Assay (Cortellis-286602-AD-01) (n=2) | % label claim Xanomeline | 102.0 | 102.8 |
| | mg Xanomeline/capsule | 76.5 | 77.1 |
| | % label claim Trospium Chloride | 95.9 | 96.0 |
| | mg Trospium Chloride/capsule | 9.6 | 9.6 |
| | Method Revision | 01 | 03 |
| Related substances (%LC)[a] (Cortellis-286602-AD-01) (n=2) | Trospium Chloride related compound B | Not detected | Not detected |
| | Trospium Chloride related compound A | Not detected | Not detected |
| | Unspecified Impurity (Xanomeline_RRT 0.24)[c,b] | 0.15 | 0.14 |
| | Unspecified Impurity (Xanomeline_RRT 1.10)[c,b] | 0.15 | 0.24 |
| | Total Impurities | 0.30 | 0.38 |
| | Method Revision | 01 | 03 |

FIG. 25

| STORAGE | | T = 0 | 40°C/75%RH | | |
|---|---|---|---|---|---|
| | | | 3 months | 6 months | |
| TEST DESCRIPTION | SPECIFICATION used at time of analysis | Stability, Rev 0 | Stability, Rev 0 | Stability, Rev 0 | |
| Conforms to acceptance criteria (Y/N) | | Y | Y | Y | |
| Description (Visual) | | Off-white opaque hard shell capsule with no markings | No change as compared to initials | No change as compared to initials | |
| Water content by KF (USP <921>, Method 1a) (n=3) | %w/w | 2.4 | 2.3 | 2.3 | |
| Assay (Corealis-28602-AD-01) (n=2) | % label claim Xanomeline | 102.0 | 103.3ᴱ | 101.8 | |
| | mg Xanomeline/capsule | 76.5 | 77.5ᴱ | 76.3 | |
| | % label claim Trospium Chloride | 95.9 | 98.7ᴱ | 94.3 | |
| | mg Trospium Chloride/capsule | 9.6 | 9.9ᴱ | 9.4 | |
| | Method Revision | 01 | 02 | 03 | |
| Related substances (%LC)ᴬ (Corealis-28602-AD-01) (n=2) | Trospium Chloride related compound B | Not detected | Not detected | Not detected | |
| | Trospium Chloride related compound A | Not detected | <0.1 | 0.16 | |
| | Unspecified Impurity (Xanomeline_RRT 0.24)ᶜ,ᴮ | 0.15 | 0.14 | 0.14 | |
| | Unspecified Impurity (Xanomeline_RRT 1.10)ᶜ,ᴰ | 0.15 | 0.20 | 0.26ᴱ | |
| | Total Impurities | 0.30 | 0.34 | 0.56 | |
| | Method Revision | 01 | 02 | 03 | |

FIG. 26

| STORAGE | | T=0 | | 3 months | | | 6 months | | |
|---|---|---|---|---|---|---|---|---|---|
| TEST DESCRIPTION | | | | 25°C/60%RH | | | 25°C/60%RH | | |
| SPECIFICATION used at time of analysis | | Stability, Rev 0 | | Stability, Rev 0 | | | Stability, Rev 0 | | |
| Conforms to acceptance criteria (Y/N) | | Y | | Y | | | Y | | |
| | Xanomeline | %LC | Range | %LC | | Range | %LC | | Range |
| | Time (min.) | | | | | | | | |
| Dissolution (%LC) (Capsule-28502-E-01) (n=6) (900 mL of 0.1N HCl, paddles at 50 rpm) | 10 | 30 | 11-53 | 34 | | 2-73 | 20 | | 2-40 |
| | 20 | 87 | 79-98 | 89 | | 69-103 | 97 | | 83-103 |
| | (Q=80%) 30 | 101 | 99-103 | 100 | | 95-107 | 103 | | 97-105 |
| | 45 | 104 | 103-105 | 103 | | 99-107 | 104 | | 102-105 |
| | Trospium Chloride | %LC | Range | %LC | | Range | %LC | | Range |
| | Time (min.) | | | | | | | | |
| | 10 | 26 | 12-47 | 34 | | 2-64 | 16 | | 2-24 |
| | 20 | 84 | 74-91 | 86 | | 70-100 | 93 | | 84-104 |
| | (Q=80%) 30 | 98 | 93-103 | 94 | | 89-104 | 100 | | 95-107 |
| | 45 | 102 | 95-105 | 96 | | 91-104 | 101 | | 95-108 |
| Method Revision | | 01 | | 01 | | | 01 | | |
| Microbial Limits* USP<61>, <62> | Total Yeasts and Molds Counts (TYMC): ≤100 cfu/g | <50 cfu/g | | N/A | | | N/A | | |
| | Total Aerobic Microbial Counts (TAMC): ≤1000 cfu/g | < 500 cfu/g | | N/A | | | N/A | | |
| | Escherichia coli: Absent | Absent | | N/A | | | N/A | | |

FIG. 27

| STORAGE | | | T=0 | | 30°C/65%RH 6 months | |
|---|---|---|---|---|---|---|
| TEST DESCRIPTION | | | Stability, Rev 0 | | Stability, Rev 0 | |
| SPECIFICATION used at time of analysis | | | | | | |
| Conforms to acceptance criteria (Y/N) | | | Y | | Y | |
| Dissolution (%LC) (Corelis-28602-B-01) (n=6) (900 mL of 0.1N HCl, paddles at 50 rpm) | Xanomeline Time (min) | 10 | %LC | Range | %LC | Range |
| | | 10 | 30 | 11-53 | 24 | 0-48 |
| | | 20 | 87 | 79-98 | 83 | 86-101 |
| | | (Q=80%) 30 | 101 | 99-103 | 102 | 101-103 |
| | | 45 | 104 | 103-105 | 103 | 102-104 |
| | Trospium Chloride Time (min) | | %LC | Range | %LC | Range |
| | | 10 | 26 | 12-47 | 23 | 0-44 |
| | | 20 | 84 | 74-91 | 91 | 87-94 |
| | | (Q=80%) 30 | 98 | 93-103 | 99 | 96-100 |
| | | 45 | 102 | 95-105 | 99 | 96-107 |
| | Method Revision | | 01 | | 01 | |
| Microbial Limits ª USP <61>, <62> | Total Yeasts and Molds Counts (TYMC): ≤100 cfu/g | | | <50 cfu/g | | N/A |
| | Total Aerobic Microbial Counts (TAMC) ≤1000 cfu/g | | | < 500 cfu/g | | N/A |
| | Escherichia coli: Absent | | | Absent | | N/A |

FIG. 28

| STORAGE | | T = 0 | | 3 months 40°C/75%RH | | | 6 months | | |
|---|---|---|---|---|---|---|---|---|---|
| TEST DESCRIPTION | | Stability, Rev 0 | | Stability, Rev 0 | | | Stability, Rev 0 | | |
| SPECIFICATION used at time of analysis | | | | | | | | | |
| Conforms to acceptance criteria (Y/N) | | Y | | Y | | | N | | |
| | | %LC | Range | %LC | | Range | %LC[f] | | Range[f] |
| Dissolution (%LC) (Cornelis-28002-B-01) (n=6) (900 mL of 0.1N HCl, paddles at 50 rpm) | Xanomeline Time (min.) | | | | | | | | |
| | 10 | 30 | 11-53 | 39 | | 29-56 | 26 | | 5-58 |
| | 20 | 87 | 79-98 | 85 | | 81-102 | 85 | | 65-103 |
| | (Q=80%) 30 | 101 | 99-103 | 103 | | 99-106 | 97 | | 90-104 |
| | 45 | 104 | 103-105 | 104 | | 103-106 | 100 | | 95-104 |
| | Trospium Chloride Time (min.) | %LC | Range | %LC | | Range | %LC[f] | | Range[f] |
| | 10 | 26 | 12-47 | 36 | | 19-48 | 24 | | 3-51 |
| | 20 | 84 | 74-91 | 91 | | 80-99 | 83 | | 64-102 |
| | (Q=80%) 30 | 98 | 93-103 | 98 | | 94-104 | 94 | | 84-103 |
| | 45 | 102 | 95-105 | 99 | | 95-105 | 97 | | 89-104 |
| | Method Revision | 01 | | 01 | | | 01 | | |
| Microbial Limits[B] USP<61>, <62> | Total Yeasts and Molds Counts (TYMC): ≤100 cfu/g | <50 cfu/g | | N/A | | | N/A | | |
| | Total Aerobic Microbial Counts (TAMC): ≤1000 cfu/g | < 500 cfu/g | | N/A | | | N/A | | |
| | Escherichia coli: Absent | Absent | | N/A | | | N/A | | |

FIG. 29

Xanomeline API Related Substances Profile for Xanomeline/Trospium Cl 75/10 mg Capsules

| Stability time point | | Initials | T = 3 months | T = 6 months |
|---|---|---|---|---|
| Related Substances (%w/w) (n=1) (Corealis-28602-AD-01) | Unspecified impurity (RRT 0.23) | 0.14 | 0.14 | 0.14 |
| | Unspecified impurity (RRT 1.09) | 0.20 | 0.14 | 0.21 |
| | Method Revision | 01 | 02 | 03 |

FIG. 30

Trospium Chloride API Related Substances Profile for Xanomeline/Trospium Cl 75/10 mg Capsules

| Stability time point | | Initials | T = 3 months | T = 6 months |
|---|---|---|---|---|
| Related Substances (%w/w) (n=1) (Corealis-28602-AD-01) | Unspecified impurity | Not Detected | Not Detected | Not Detected |
| | Method Revision | 01 | 02 | 03 |

FIG. 31

Specification for Xanomeline/Trospium Cl 75/10 mg Capsules

| TEST DESCRIPTION | ACCEPTANCE CRITERIA Stability, Rev 0 |
|---|---|
| Description (Visual) | White to off-white opaque hard shell capsule with no markings |
| Water Content by KF (USP <921>, Method 1a) | Report result |
| Assay (%LC) (Corealis-28602-AD) | Xanomeline: 90 – 110% label claim (68 – 83 mg Xanomeline/capsule) |
| | Trospium Chloride: 90 – 110% label claim (9 – 11 mg Trospium Chloride/capsule) |
| Related Substances (%LC)ᴬ (Corealis-28602-AD) | Trospium Chloride related compound B: NMT 0.2%LC |
| | Trospium Chloride related compound A: NMT 0.2%LC |
| | Any single unspecified impurity: NMT 0.2%LC |
| | Total Impurities: NMT 1.5%LC |
| Dissolution (Corealis-28602-B) | Xanomeline: NLT 80% (Q) of labeled amount of Xanomeline is dissolved at 30 minutes. Report profile |
| | Trospium Chloride: NLT 80% (Q) of labeled amount of Trospium Chloride is dissolved at 30 minutes. Report profile |
| Microbial Limits ᴮ USP<61>, <62> | Total Yeasts and Molds Counts (TYMC): ≤100 cfu/g |
| | Total Aerobic Microbial Counts (TAMC): ≤1000 cfu/g |
| | Escherichia coli: Absent |

FIG. 32

| STORAGE | | T = 0 | | 25°C/60%RH | | | |
|---|---|---|---|---|---|---|---|
| TEST DESCRIPTION | | | | 3 Months | | 6 Months | |
| SPECIFICATION used at time of analysis | | Stability, Rev 0 | | Stability, Rev 0 | | Stability, Rev 0 | |
| Conforms to acceptance criteria (Y/N) | | Y | | Y | | Y | |
| | Xanomeline Time (min.) | %LC | Range | %LC | Range | %LC | Range |
| | 10 | 27 | 7-69 | 41 | 7-94 | 26 | 10-48 |
| | 20 | 86 | 74-99 | 96 | 94-105 | 95 | 89-101 |
| Dissolution (%LC) (Corsolis-28602-8-01) (n=6) (900 mL of 0.1N HCl, paddles at 50 rpm) | (Q=80%) 30 | 98 | 86-104 | 103 | 101-105 | 105 | 105-107 |
| | 45 | 101 | 91-105 | 103 | 102-105 | 106 | 105-108 |
| | Trospium Chloride Time (min.) | %LC | Range | %LC | Range | %LC | Range |
| | 10 | 26 | 7-65 | 35 | 5-82 | 22 | 9-39 |
| | 20 | 84 | 75-93 | 92 | 86-97 | 91 | 87-93 |
| | (Q=80%) 30 | 96 | 89-101 | 96 | 92-100 | 100 | 97-103 |
| | 45 | 99 | 93-102 | 96 | 93-100 | 101 | 97-104 |
| | Method Revision | 01 | | 01 | | 01 | |
| Microbial Limits<sup>a</sup> USP <61>, <62> | Total Yeasts and Molds Counts (TYMC): ≤100 cfu/g | <50 cfu/g | | N/A | | N/A | |
| | Total Aerobic Microbial Counts (TAMC): ≤1000 cfu/g | <500 cfu/g | | N/A | | N/A | |
| | Escherichia coli: Absent | Absent | | N/A | | N/A | |

FIG. 33

| STORAGE | | | T=0 | | 30°C/65%RH 6 Months | |
|---|---|---|---|---|---|---|
| TEST DESCRIPTION | | | Stability, Rev 0 | | Stability, Rev 0 | |
| SPECIFICATION used at time of analysis | | | Y | | Y | |
| Conforms to acceptance criteria (Y/N) | | | | | | |
| | Xanomeline | Time (min.) | %LC | Range | %LC | Range |
| Dissolution (%LC) (Coreais-28602-B-01) (n=6) (900 mL of 0.1N HCl, paddles at 50 rpm) | | 10 | 27 | 7-69 | 16 | 5-46 |
| | | 20 | 86 | 74-99 | 85 | 76-89 |
| | | (Q=80%) 30 | 98 | 86-104 | 99 | 86-101 |
| | | 45 | 101 | 91-105 | 103 | 99-105 |
| | Trospium Chloride | Time (min.) | %LC | Range | %LC | Range |
| | | 10 | 28 | 7-65 | 12 | 5-34 |
| | | 20 | 84 | 75-93 | 81 | 77-85 |
| | | (Q=80%) 30 | 96 | 89-101 | 94 | 92-96 |
| | | 45 | 99 | 93-102 | 97 | 95-100 |
| | Method Revision | | 01 | | 01 | |
| Microbial Limits * USP<61>, <62> | Total Yeasts and Molds Counts (TYMC): ≤100 cfu/g | | <50 cfu/g | | N/A | |
| | Total Aerobic Microbial Counts (TAMC): ≤1000 cfu/g | | < 500 cfu/g | | N/A | |
| | Escherichia coli: Absent | | Absent | | N/A | |

FIG. 34

| STORAGE | | T=0 | 40°C/75%RH | |
|---|---|---|---|---|
| TEST DESCRIPTION | | | 3 Months | 6 Months |
| SPECIFICATION used at time of analysis | | Stability, Rev 0 | Stability, Rev 0 | Stability, Rev 0 |
| Conforms to acceptance criteria (Y/N) | | Y | Y | N |
| Description (Visual) | | Off-white opaque hard shell capsule with no markings | No change as compared to initials | No change as compared to initials |
| Water content by KF (USP <921>, Method 1a) (n=3) | %w/w | 2.9 | 3.1 | 2.8 |
| Assay (Coreolis-286632-AO-01) (n=2) | % label claim Xanomeline | 102.1 | 102.8 | 102.9 |
| | mg Xanomeline/capsule | 76.5 | 77.1 | 77.2 |
| | % label claim Trospium Chloride | 94.6 | 101.3 | 95.4 |
| | mg Trospium Chloride/capsule | 18.9 | 20.3 | 19.1 |
| | Method Revision | 01 | 02 | 03 |
| Related substances (%LC)[a] (Coreolis-286632-AO-01) (n=2) | Trospium Chloride related compound B | Not detected | Not detected | Not detected |
| | Trospium Chloride related compound A | Not detected | <0.1 | 0.14 |
| | Unspecified impurity (Xanomeline_RRT 0.24) c, b | 0.15 | 0.14 | 0.14 |
| | Unspecified impurity (Xanomeline_RRT 1.10) c, b | 0.18 | 0.21 | 0.27[c] |
| | Total Impurities | 0.32 | 0.35 | 0.55 |
| | Method Revision | 01 | 02 | 03 |

FIG. 35

| STORAGE | | T = 0 | | 25°C/60%RH | | | |
|---|---|---|---|---|---|---|---|
| TEST DESCRIPTION | | Stability, Rev 0 | | 3 Months Stability, Rev 0 | | 6 Months Stability, Rev 0 | |
| SPECIFICATION used at time of analysis | | | | | | | |
| Conforms to acceptance criteria (Y/N) | | Y | | Y | | Y | |
| | Xanomeline Time (min.) | %LC | Range | %LC | Range | %LC | Range |
| Dissolution (%LC) (Corresis-29/02-9-01) (Rot) (900 mL of 0.1N HCl, paddles at 50 rpm) | 10 | 27 | 7-89 | 41 | 7-94 | 28 | 10-48 |
| | 20 | 86 | 74-89 | 98 | 94-105 | 95 | 89-101 |
| | 30 (Q=80%) | 98 | 86-104 | 100 | 101-105 | 105 | 105-107 |
| | 45 | 101 | 91-105 | 103 | 102-105 | 105 | 105-108 |
| | Trospium Chloride Time (min.) | %LC | Range | %LC | Range | %LC | Range |
| | 10 | 26 | 7-65 | 35 | 5-82 | 22 | 9-39 |
| | 20 | 84 | 75-90 | 92 | 86-97 | 91 | 87-93 |
| | 30 (Q=80%) | 96 | 89-101 | 96 | 92-100 | 100 | 97-103 |
| | 45 | 99 | 93-102 | 96 | 93-100 | 101 | 97-104 |
| | Method Revision | 01 | | 01 | | 01 | |
| Microbial Limits USP<61>, <62> | Total Yeasts and Molds Counts (TYMC): ≤100 cfu/g | <50 cfu/g | | N/A | | N/A | |
| | Total Aerobic Microbial Counts (TAMC): ≤1000 cfu/g | <500 cfu/g | | N/A | | N/A | |
| | Escherichia coli: Absent | Absent | | N/A | | N/A | |

FIG. 36

| STORAGE | | T=0 | | 30°C/65%RH 6 Months | |
|---|---|---|---|---|---|
| TEST DESCRIPTION | | Stability, Rev 0 | | Stability, Rev 0 | |
| SPECIFICATION used at time of analysis | | | | | |
| Conforms to acceptance criteria (Y/N) | | Y | | Y | |
| | Xanomeline Time (min.) | %LC | Range | %LC | Range |
| Dissolution (%LC) (Coreais-28602-B-01) (n=6) (900 mL of 0.1N HCl, paddles at 50 rpm) | 10 | 27 | 7-69 | 18 | 5-46 |
| | 20 | 88 | 74-99 | 85 | 76-89 |
| | (Q=80%) 30 | 98 | 86-104 | 99 | 96-101 |
| | 45 | 101 | 91-105 | 103 | 99-105 |
| | Trospium Chloride Time (min.) | %LC | Range | %LC | Range |
| | 10 | 28 | 7-65 | 12 | 5-34 |
| | 20 | 84 | 75-93 | 81 | 77-85 |
| | (Q=80%) 30 | 96 | 89-101 | 94 | 92-96 |
| | 45 | 99 | 93-102 | 97 | 95-100 |
| | Method Revision | 01 | | 01 | |
| Microbial Limits * USP <61>, <62> | Total Yeasts and Molds Counts (TYMC): ≤100 cfu/g | <50 cfu/g | | N/A | |
| | Total Aerobic Microbial Counts (TAMC): ≤1000 cfu/g | < 500 cfu/g | | N/A | |
| | Escherichia coli: Absent | Absent | | N/A | |

FIG. 37

| STORAGE | | T = 0 | | 40°C/75%RH | | | |
|---|---|---|---|---|---|---|---|
| TEST DESCRIPTION | | | | 3 Months | | 6 Months | |
| SPECIFICATION used at time of analysis | | Stability, Rev 0 | | Stability, Rev 0 | | Stability, Rev 0 | |
| Conforms to acceptance criteria (Y/N) | | Y | | Y | | N | |
| Xanomeline Time (min.) | | %LC | Range | %LC* | Range* | %LC | Range |
| | 10 | 27 | 7-69 | 43 | 22-64 | 24 | 11-47 |
| | 20 | 86 | 74-99 | 91 | 71-100 | 93 | 78-100 |
| (Q=80%) | 30 | 98 | 86-104 | 99 | 83-103 | 100 | 92-103 |
| | 45 | 101 | 91-105 | 100 | 84-103 | 102 | 98-104 |
| Trospium Chloride Time (min.) | | %LC | Range | %LC* | Range* | %LC | Range |
| | 10 | 26 | 7-65 | 39 | 18-67 | 24 | 9-45 |
| | 20 | 84 | 75-93 | 89 | 73-100 | 90 | 84-96 |
| (Q=80%) | 30 | 98 | 89-101 | 96 | 90-105 | 97 | 92-100 |
| | 45 | 99 | 93-102 | 97 | 90-106 | 99 | 94-103 |
| Method Revision | | 01 | | 01 | | 01 | |
| Microbial Limits* USP <61>, <62> | Total Yeasts and Molds Counts (TYMC): ≤100 cfu/g | <50 cfu/g | | N/A | | N/A | |
| | Total Aerobic Microbial Counts (TAMC): ≤1000 cfu/g | <500 cfu/g | | N/A | | N/A | |
| | Escherichia coli: Absent | Absent | | N/A | | N/A | |

Dissolution (%LC) (Coresta-28R02.B-01) (n=6) (900 mL of 0.1 N HCl, paddles at 50 rpm)

FIG. 38

Xanomeline API Related Substances Profile for Xanomeline/Trospium Cl 75/20 mg Capsules

| Stability time point | | Initials | T = 3 months | T = 6 months |
|---|---|---|---|---|
| Related Substances (%w/w) (n=1) (Corealis-28602-AD-01) | Unspecified impurity (RRT 0.23) | 0.14 | 0.14 | 0.14 |
| | Unspecified impurity (RRT 1.09) | 0.20 | 0.14 | 0.21 |
| | Method Revision | 01 | 02 | 03 |

FIG. 39

Trospium Chloride API Related Substances Profile for Xanomeline/Trospium Cl 75/20 Capsules

| Stability time point | | Initials | T = 3 months | T = 6 months |
|---|---|---|---|---|
| Related Substances (%w/w) (n=1) (Corealis-28602-AD-01) | Unspecified impurity | Not Detected | Not Detected | Not Detected |
| | Method Revision | 01 | 02 | 03 |

FIG. 40

Specification for Xanomeline/Trospium Cl 75/20 mg Capsules

| TEST DESCRIPTION | ACCEPTANCE CRITERIA |
|---|---|
| | Stability, Rev 0 |
| Description (Visual) | White to off-white opaque hard shell capsule with no markings |
| Water Content by KF (USP <921>, Method 1a) | Report result |
| Assay (%LC) (Corealis-28602-AD) | Xanomeline: 90 - 110% label claim (68 – 83 mg Xanomeline/capsule) |
| | Trospium Chloride: 90 - 110% label claim (18 – 22mg Trospium Chloride/capsule) |
| Related Substances (%LC) ª (Corealis-28602-AD) | Trospium Chloride related compound B: NMT 0.2%LC |
| | Trospium Chloride related compound A: NMT 0.2%LC |
| | Any single unspecified impurity: NMT 0.2%LC |
| | Total Impurities: NMT 1.5%LC |
| Dissolution (Corealis-28602-B) | Xanomeline: NLT 80% (Q) of labeled amount of Xanomeline is dissolved at 30 minutes. Report profile |
| | Trospium Chloride: NLT 80% (Q) of labeled amount of Trospium Chloride is dissolved at 30 minutes. Report profile |
| Microbial Limits ᵇ USP<61>, <62> | Total Yeasts and Molds Counts (TYMC): ≤100 cfu/g |
| | Total Aerobic Microbial Counts (TAMC): ≤1000 cfu/g |
| | Escherichia coli: Absent |

FIG. 41

COMPOSITIONS AND METHODS FOR TREATING DISORDERS AMELIORATED BY MUSCARINIC RECEPTOR ACTIVATION

This application claims the benefit of the filing date as a continuation of U.S. patent application Ser. No. 17/143,904, filed on Jan. 7, 2021, which is a continuation of United States patent application No. 16/585,532, filed on Sep. 27, 2019 (now U.S. Pat. No. 10,933,020), and claims the benefit of priority of U.S. Provisional Patent Application Ser. No. 62/738,333 filed Sep. 28, 2018, the disclosures of which are each incorporated by reference in their entireties for all purposes.

The present disclosure relates to compositions and their application as pharmaceuticals for treating disorders ameliorated by activating muscarinic receptors in a human or animal subject.

Schizophrenia affects about 0.5 to 1% of the population. The disease is characterized by a set of symptoms divided into positive symptoms (e.g., hallucinations, delusional thoughts, etc.), negative symptoms (e.g., social isolation, anhedonia, etc.), and cognitive symptoms (e.g., inability to process information, poor working memory, etc.). Patients who suffer from schizophrenia experience a major decline in quality of life and are at increased risk for mortality due to many factors, such as an increased suicide rate. The cost of schizophrenia to society is high, as sufferers of schizophrenia are much more likely to be incarcerated, homeless, or unemployed.

Existing treatments for schizophrenia rely upon dopamine and serotonin receptors, as was the case with the first antipsychotic, chlorpromazine, discovered in 1952. For more than 60 years, the same fundamental pharmacology has been the standard of care in schizophrenia. Current antipsychotics are only efficacious toward positive symptoms, leaving negative and cognitive symptoms untreated. Alzheimer's disease is another therapeutic area in which it has proven extremely difficult to develop new therapies, with a success rate of only 0.4% for molecules that enter clinical development and receive marketing approval. New treatments are desperately needed by patients in these areas, but development has been extremely difficult despite substantial efforts from scientists and drug developers around the world.

Activating the muscarinic system through muscarinic agonists may treat several diseases, such as schizophrenia, Alzheimer's disease, Parkinson's disease, depression, movement disorders, drug addiction, pain, and neurodegeneration, such as tauopathies or synucleinopathies. Muscarinic cholinergic receptors are G-protein coupled receptors with five different receptor subtypes (M1-M5), each of which is found in the CNS with different tissue distributions. M1 and M4 subtypes have been of interest as therapeutic targets for various diseases. For instance, the mood stabilizers lithium and valproic acid, used for treating bipolar depression, may exert their effects via the muscarinic system, particularly through the M4 subtype receptor. Genetic evidence directly links the muscarinic system and alcohol addiction.

In a double-blind placebo-controlled trial of schizophrenic patients using xanomeline, a muscarinic cholinergic receptor agonist with preferential activity at the M1 and M4 subtype receptors, schizophrenia was alleviated. However, because xanomeline also bound to muscarinic receptors outside the brain, many serious side effects resulted, including GI side effects, cardiac side effects, and hypersalivation. Dose-limited adverse events were problematic and led to very high discontinuation rates (including a 56% dropout rate in a 26-week study of Alzheimer's disease) and eventually to discontinuation of xanomeline development. Despite the early promise, xanomeline development halted for more than 15 years. Many companies attempted and failed to develop muscarinic receptor agonists for CNS disorders, which avoided these unacceptable side effects, but no such agonist has reached the market. Past development efforts focused on medicinal chemistry to develop molecules that would be more tolerable, typically by selecting for the M1 and M4 subtypes over the M2 and M3 muscarinic receptor subtypes. However, M1 and/or M4 activation outside the brain may still cause muscarinic related intolerance. Very little progress has been made to mitigate adverse effects due to the activation of peripheral muscarinic receptors.

There remains a need in the art for a pharmaceutical composition with increased tolerability for xanomeline, especially to treat cognitive and psychotic disorders. The following embodiments and aspects thereof are described and illustrated with compositions and methods, which are meant to be exemplary and illustrative, not limiting in scope. In various embodiments, one or more of the above-described problems have been reduced or eliminated, while other embodiments are directed to other improvements.

Provided herein is an oral pharmaceutical composition, comprising a plurality of xanomeline beads comprising xanomeline or a salt thereof; and a plurality of trospium beads comprising a salt of trospium.

In certain embodiments, the size of the xanomeline beads is between 0.425 mm and 1.18 mm. In certain embodiments, the size of the xanomeline beads is between 0.6 mm and 0.85 mm. In certain embodiments, the size of the trospium beads is between 0.425 mm and 1.18 mm. In certain embodiments, the size of the trospium beads is between 0.6 mm and 0.85 mm.

In certain embodiments, the xanomeline beads contain about 2.5 times as much xanomeline as the trospium beads contain trospium chloride.

In certain embodiments, the plurality of xanomeline and the plurality of trospium beads have a dissolution rate of more than about 95% within about the first 45 minutes following contact with an aqueous solution. In certain embodiments, the dissolution rate of more than about 95% occurs within about the first 20 minutes following contact with an aqueous solution.

In certain embodiments, when administered to a patient for at least 7 days at 20 mg trospium twice daily, the oral pharmaceutical composition provides a mean $C_{max}$ of trospium at 7850±3360 pg/mL. In certain embodiments, when administered to a patient for at least 7 days at 20 mg trospium twice daily, oral pharmaceutical composition provides a mean $AUC_{0-12}$ of 41900±15500 hr·pg/mL.

In certain embodiments, the xanomeline salt is xanomeline tartrate. In certain embodiments, the xanomeline beads comprise between 30 wt. % and 80 wt. % xanomeline tartrate, such as 66 wt. % xanomeline tartrate. In certain embodiments, the xanomeline beads comprise between 15 wt. % and 65 wt. % microcrystalline cellulose, such as 33.5 wt. % microcrystalline cellulose. In certain embodiments, the xanomeline beads comprise between 0 wt. % and 2 wt. % talc, such as 0.5 wt. % talc. In certain embodiments, the xanomeline beads comprise between 30 wt. % and 80 wt. % xanomeline tartrate, between 15 wt. % and 65 wt. % microcrystalline cellulose, and between 0 wt. % and 2 wt. % talc. In certain embodiments, the xanomeline beads comprise 66 wt. % xanomeline tartrate, 33.5 wt. % microcrystalline cellulose, and 0.5 wt. % talc.

In certain embodiments, the trospium salt is trospium chloride. In certain embodiments, the trospium beads comprise between 8 wt. % and 35 wt. % trospium chloride, such as 17.7 wt. % trospium chloride. In certain embodiments, the trospium beads comprise between 25 wt. % and 80 wt. % microcrystalline cellulose, such as 46.8 wt. % microcrystalline cellulose. In certain embodiments, the trospium beads comprise between 15 wt. % and 70 wt. % lactose monohydrate, such as 35 wt. % lactose monohydrate. In certain embodiments, the trospium beads comprise between 0 wt. % and 2 wt. % talc, such as 0.5 wt. % talc. In certain embodiments, the trospium beads comprise between 8 wt. % and 35 wt. % trospium chloride, between 25 wt. % and 80 wt. % microcrystalline cellulose, between 15 wt. % and 70 wt. % lactose monohydrate, and between 0 wt. % and 2 wt. % talc. In certain embodiments, the trospium beads comprise 17.7 wt. % trospium chloride, 46.8 wt. % microcrystalline cellulose, 35 wt. % lactose monohydrate, and 0.5 wt. % talc.

In certain embodiments, the oral pharmaceutical composition further comprises a capsule containing the plurality of xanomeline beads and the plurality of trospium beads. In certain embodiments, the capsule has a dosage strength of 50 mg xanomeline free base and 20 mg trospium chloride. In certain embodiments, the capsule has a dosage strength of 50 mg xanomeline free base and 10 mg trospium chloride. In certain embodiments, the capsule has a dosage strength of 75 mg xanomeline free base and 20 mg trospium chloride. In certain embodiments, the capsule has a dosage strength of 75 mg xanomeline free base and 10 mg trospium chloride. In certain embodiments, the capsule has a dosage strength of 125 mg xanomeline free base and 30 mg trospium chloride. In certain embodiments, the capsule has a dosage strength of 125 mg xanomeline free base and 40 mg trospium chloride.

The present disclosure also provides an oral pharmaceutical composition, comprising: a plurality of xanomeline beads having a size between 0.425 mm and 1.18 mm, and core comprising between 30 wt. % and 80 wt. % xanomeline tartrate, between 15 wt. % and 65 wt. % microcrystalline cellulose, and between 0.2 wt. % and 2 wt. % talc; and a plurality of trospium beads having a size between 0.425 mm and 1.18 mm, and a core comprising between 8 wt. % and 35 wt. % trospium, between 25 wt. % and 80 wt. % microcrystalline cellulose, between 15 wt. % and 70 wt. % lactose monohydrate, and between 0.2 wt. % and 2 wt. % talc; the plurality of xanomeline and the plurality of trospium beads having a dissolution rate of more than about 95% within about the first 45 minutes following entry of the dosage form into an aqueous solution; and wherein, when administered to a patient for at least 7 days at 20 mg trospium twice daily, providing a mean $C_{max}$ of trospium at 7850±3360 pg/mL and a mean $AUC_{0-12}$ of 41900±15500 hr·pg/mL.

The present disclosure also provides an oral pharmaceutical composition, comprising: a capsule containing a plurality of xanomeline beads and a plurality of trospium beads; the plurality of xanomeline beads having a size between 0.6 mm and 0.85 mm, and a core comprising between 66 wt. % xanomeline tartrate, 33.5 wt. % microcrystalline cellulose, and 0.5 wt. % talc; and the plurality of trospium beads having a size between 0.6 mm and 0.85 mm, and a core comprising 17.7 wt. % trospium chloride, 46.8 wt. % microcrystalline cellulose, 35 wt. % lactose monohydrate, and 0.5 wt. % talc; the plurality of xanomeline and the plurality of trospium beads having a dissolution rate of more than about 95% within about the first 20 minutes following the entry of the dosage form into an aqueous solution; and wherein, when administered to a patient for at least 7 days at 20 mg trospium twice daily, providing a mean $C_{max}$ of trospium at 7850±3360 pg/mL and a mean $AUC_{0-12}$ of 41900±15500 hr·pg/mL.

Further provided is a method of activating muscarinic receptors in a biological sample comprising contacting the biological sample with any oral pharmaceutical composition described herein.

Also provided is a method for treating a disorder ameliorated by activating muscarinic receptors in a subject in need thereof, comprising administering to a patient in need thereof any oral pharmaceutical composition described herein. In certain embodiments, the subject is a human. In certain embodiments, the disorder is selected from schizophrenia, Alzheimer's disease, Parkinson's disease, depression, movement disorders, pain, drug addiction, tauopathy, and synucleinopathy.

Further provided is a method of treating a disorder ameliorated by activating muscarinic receptors in a subject in need thereof, comprising the sequential or co-administration of any oral pharmaceutical composition described herein; and a second therapeutic agent.

The present disclosure also provides an oral pharmaceutical composition, comprising xanomeline and/or a salt thereof and less than 0.5 wt. % 3-[(4-hexyloxy)-1,2,5-thiadiazol-3-yl]-5-hydroxyl-1-methylpyridin-1-ium. Also provided is an oral pharmaceutical composition, comprising a plurality of xanomeline beads comprising xanomeline or a salt thereof and less than 0.5 wt. % 3-[(4-hexyloxy)-1,2,5-thiadiazol-3-yl]-5-hydroxyl-1-methylpyridin-1-ium; and a plurality of trospium beads comprising a salt of trospium.

The present disclosure further provides an oral pharmaceutical composition, comprising xanomeline and/or a salt thereof and trospium chloride for treating a muscarinic disorder in a patient in need thereof, wherein when administered to the patient in need thereof, the composition is sufficient to provide an in-vivo plasma profile comprising a median $T_{max}$ for xanomeline of 2 hours and a median $T_{max}$ for trospium of 1 hour. In certain embodiments, the in-vivo plasma profile further comprises a mean dose-normalized $C_{max}$ of between 48.5 and 121.3 pg/mL/mg and a mean dose-normalized $C_{max}$ of trospium of between 156 and 375 pg/mL/mg. In certain embodiments, the in-vivo plasma profile further comprises a mean dose-normalized $AUC_{0-12}$ of xanomeline of between 263 and 577 hr·pg/mL/mg and a mean dose-normalized $AUC_{0-12}$ of trospium of between 881 and 2024 hr·pg/mL/mg.

Further aspects and advantages will be apparent to those of ordinary skill in the art from a review of the following detailed description. While the dosage form, method of making, and method of treatment are susceptible of embodiments in various forms, the description hereafter includes specific embodiments with the understanding that the disclosure is illustrative and is not intended to limit the disclosure to the specific embodiments described herein.

BRIEF DESCRIPTION OF THE DRAWINGS

The disclosure will be readily understood by the following detailed description in conjunction with the accompanying drawings, wherein like reference numerals designate like structural elements. The drawings provide exemplary embodiments or aspects of the disclosure and do not limit the scope of the disclosure.

FIG. 1 shows the stability schedule and protocol for xanomeline/trospium capsules.

FIG. 6 shows the stability data for xanomeline/trospium Cl, 50/10 mg capsules stored at 25° C./60% RH and measured at time 0, 3 months, 6 months, and 9 months.

FIG. 7 shows the stability data for xanomeline/trospium Cl, 50/10 mg capsules stored at 30° C./65% RH and measured at time 0, 3 months, and 6 months.

FIG. 8 shows the stability data for xanomeline/trospium Cl, 50/10 mg capsules stored at 40° C./75% RH and measured at time 0, 3 months, and 6 months.

FIG. 9 is the dissolution for xanomeline/trospium Cl, 50/10 mg capsules stored at 25° C./60% RH and measured at time 0, 3 months, 6 months, and 9 months.

FIG. 10 is the dissolution profile for xanomeline/trospium Cl, 50/10 mg capsules stored at 30° C./65% RH and measured at time 0, 3 months, and 6 months.

FIG. 11 is the dissolution profile for xanomeline/trospium Cl, 50/10 mg capsules stored at 40° C./75% RH and measured at time 0, 3 months, and 6 months.

FIG. 12 is the xanomeline active pharmaceutical ingredient related substances profile for xanomeline/trospium Cl 50/10 mg capsules and measured at time 0, 3 months, 6 months, and 9 months.

FIG. 13 is trospium chloride active pharmaceutical ingredient related substances profile for xanomeline/trospium Cl 50/10 mg capsules and measured at time 0, 3 months, 6 months, and 9 months.

FIG. 14 is the specification for xanomeline/trospium Cl 50/10 mg capsules.

FIG. 15 shows the stability data for xanomeline/trospium Cl, 50/20 mg capsules stored at 25° C./60% RH and measured at time 0, 3 months, and 6 months.

FIG. 16 shows the stability data for xanomeline/trospium Cl, 50/20 mg capsules stored at 30° C./65% RH and measured at time 0 and 6 months.

FIG. 17 shows the stability data for xanomeline/trospium Cl, 50/20 mg capsules stored at 40° C./75% RH and measured at time 0, 3 months, and 6 months.

FIG. 18 is the dissolution for xanomeline/trospium Cl, 50/20 mg capsules stored at 25° C./60% RH and measured at time 0, 3 months, 6, and 9 months.

FIG. 19 is the dissolution profile for xanomeline/trospium Cl, 50/20 mg capsules stored at 30° C./65% RH and measured at time 0 and 6 months.

FIG. 20 is the dissolution profile for xanomeline/trospium Cl, 50/20 mg capsules stored at 40° C./75% RH and measured at time 0, 3 months, and 6 months.

FIG. 21 is the xanomeline active pharmaceutical ingredient related substances profile for xanomeline/trospium Cl 50/20 mg capsules and measured at time 0, 3 months, and 6 months.

FIG. 22 is trospium chloride active pharmaceutical ingredient related substances profile for xanomeline/trospium Cl 50/20 mg capsules and measured at time 0, 3 months, and 6 months.

FIG. 23 is the specification for xanomeline/trospium Cl 50/20 mg capsules.

FIG. 24 shows the stability data for xanomeline/trospium Cl, 75/10 mg capsules stored at 25° C./60% RH and measured at time 0, 3 months, and 6 months.

FIG. 25 shows the stability data for xanomeline/trospium Cl, 75/10 mg capsules stored at 30° C./65% RH and measured at time 0 and 6 months.

FIG. 26 shows the stability data for xanomeline/trospium Cl, 75/10 mg capsules stored at 40° C./75% RH and measured at time 0, 3 months, and 6 months.

FIG. 27 is the dissolution for xanomeline/trospium Cl, 75/10 mg capsules stored at 25° C./60% RH and measured at time 0, 3 months, and 6 months.

FIG. 28 is the dissolution profile for xanomeline/trospium Cl, 75/10 mg capsules stored at 30° C./65% RH and measured at time 0 and 6 months.

FIG. 29 is the dissolution profile for xanomeline/trospium Cl, 75/10 mg capsules stored at 40° C./75% RH and measured at time 0, 3 months, and 6 months.

FIG. 30 is the xanomeline active pharmaceutical ingredient related substances profile for xanomeline/trospium Cl 75/10 mg capsules and measured at time 0, 3 months, and 6 months.

FIG. 31 is trospium chloride active pharmaceutical ingredient related substances profile for xanomeline/trospium Cl 75/10 mg capsules and measured at time 0, 3 months, and 6 months.

FIG. 32 is the specification for xanomeline/trospium Cl 75/10 mg capsules.

FIG. 33 is the dissolution for xanomeline/trospium Cl, 75/20 mg capsules stored at 25° C./60% RH and measured at time 0, 3 months, and 6 months.

FIG. 34 is the dissolution for xanomeline/trospium Cl, 75/20 mg capsules stored at 30° C./65% RH and measured at time 0 and 6 months.

FIG. 35 shows the stability data for xanomeline/trospium Cl, 75/20 mg capsules stored at 40° C./75% RH and measured at time 0, 3 months, and 6 months.

FIG. 36 is the dissolution for xanomeline/trospium Cl, 75/20 mg capsules stored at 25° C./60% RH and measured at time 0, 3 months, and 6 months.

FIG. 37 is the dissolution profile for xanomeline/trospium Cl, 75/20 mg capsules stored at 30° C./65% RH and measured at time 0 and 6 months.

FIG. 38 is the dissolution profile for xanomeline/trospium Cl, 75/20 mg capsules stored at 40° C./75% RH and measured at time 0, 3 months, and 6 months.

FIG. 39 is the xanomeline active pharmaceutical ingredient related substances profile for xanomeline/trospium Cl 75/20 mg capsules and measured at time 0, 3 months, and 6 months.

FIG. 40 is trospium chloride active pharmaceutical ingredient related substances profile for xanomeline/trospium Cl 75/20 mg capsules and measured at time 0, 3 months, and 6 months.

FIG. 41 is the specification for xanomeline/trospium Cl 75/20 mg capsules.

DETAILED DESCRIPTION

Figure 2:
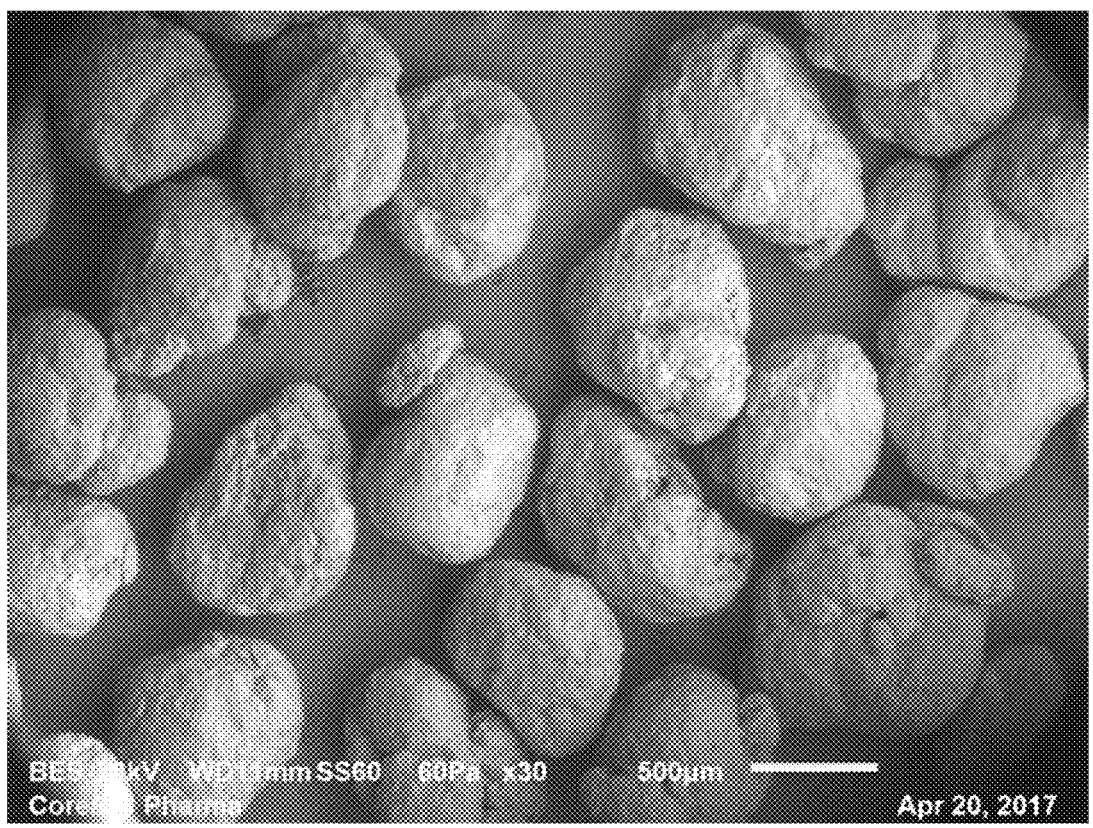
FIG. 2 is a scanning electron microscope (SEM) image of xanomeline tartrate 66% beads at 30× magnification, showing that the beads are sized between 0.6 mm and 0.85 mm used for xanomeline/trospium capsules.

The articles "a" and "an" refer to one or to more than one (i.e., to at least one) of the grammatical object of the article. By way of example, "an element" means one element or more than one element.

The terms "comprise" and "comprising" are inclusive, open sense, meaning that additional elements may be included.

The term "consisting" limits the elements to those specified except for impurities ordinarily associated therewith.

The term "consisting essentially of" limits the elements to those specified and those that do not materially affect the basic and novel characteristics of the material or steps.

All ranges set forth herein include all possible subsets of ranges and any combinations of such subset ranges. By default, ranges include the stated endpoints, unless stated otherwise, where a range of values is provided, each intervening value between the upper and lower limit of that range and any other stated or intervening value in that stated range is encompassed within the disclosure. The upper and lower limits of these smaller ranges may independently be included in the smaller ranges and are also encompassed within the disclosure, subject to any specifically excluded limit in the stated range. Where the stated range includes one or both limits, ranges excluding either or both of those included limits are also contemplated to be part of the disclosure.

The term "wt. %" is the weight percent based on the total weight, e.g., of the core, or enteric coating, or total bead, as described in context. Unless stated otherwise, the wt. % is intended to describe the weight percent based on dry weight (e.g., for a core following drying).

The term "controlled release" is defined as a prolonged-release pattern of one or more drugs, such that the drugs are released over a period. A controlled release formulation has release kinetics that results in measurable serum levels of the drug over a period longer than what would be possible following intravenous injection or following administration of an immediate release oral dosage form. Controlled release, slow-release, sustained-release, extended-release, prolonged-release, and delayed-release have the same definitions herein.

The term "including" means "including but not limited to." "Including" and "including but not limited to" are used interchangeably.

The term "mammal" is known in the art. Exemplary mammals include humans, primates, bovines, porcines, canines, felines, and rodents (e.g., mice and rats).

The terms "parenteral administration" and "administered parenterally" are art-recognized and refer to modes of administration other than enteral and topical administration, usually by injection. These modes include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, and intrasternal injection and infusion.

A "patient," "subject," or "host" to be treated by the subject method means either a human or non-human mammal.

The term "pharmaceutically-acceptable carrier" is art-recognized and refers to a pharmaceutically-acceptable material, composition, or vehicle, such as a liquid or solid filler, diluent, excipient, solvent, or encapsulating material, involved in carrying or transporting any subject composition or component thereof from one organ, or portion of the body, to another organ, or portion of the body. Each carrier must be "acceptable" in the sense of being compatible with the subject composition and its components and not injurious to the patient. Some examples of materials that may serve as pharmaceutically acceptable carriers include sugars, such as lactose, glucose, and sucrose; starches, such as corn starch and potato starch; cellulose and its derivatives, such as sodium carboxymethyl cellulose, ethylcellulose, and cellulose acetate; powdered tragacanth; malt; gelatin; talc; excipients, such as cocoa butter and suppository waxes; oils, such as peanut oil, cottonseed oil, safflower oil, sesame oil, olive oil, corn oil, and soybean oil; glycols, such as propylene glycol; polyols, such as glycerin, sorbitol, mannitol, and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

The term "pharmaceutically-acceptable salts" is art-recognized and refers to salts prepared from relatively nontoxic acids or bases, including inorganic acids and bases and organic acids and bases, including, for example, those contained in compositions of the present disclosure. Suitable non-toxic acids include inorganic and organic acids such as acetic, benzenesulfonic, benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, hydrochloric, hydrobromic, phosphoric, and sulfuric acids and the like.

The term "treating" is art-recognized and refers to curing as well as ameliorating at least one symptom of any condition or disorder.

In jurisdictions that forbid the patenting of methods practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation consistent with laws or regulations defining patentable subject matter is intended. In jurisdictions that do not forbid the patenting of methods practiced on the human body, the "administering" of compositions includes both methods practiced on the human body and the foregoing activities.

The term "therapeutic agent" is art-recognized and refers to any chemical moiety that is a biologically, physiologically, or pharmacologically active substance acting locally or systemically in a subject. Examples of therapeutic agents also referred to as "drugs," are described in well-known literature references such as the *Merck Index* (14th edition), the *Physicians' Desk Reference* (64th edition), and *The Pharmacological Basis of Therapeutics* (12th edition). These therapeutic agents include without limitation medicaments; vitamins; mineral supplements; substances used for the treatment, prevention, diagnosis, cure, or mitigation of a disease or illness; substances that affect the structure or function of the body, or pro-drugs, which become biologically active or more active after they have been placed in a physiological environment.

The term "psychotherapy" refers to non-pharmacological therapies in which those skilled in the art use a variety of techniques involving verbal and other interactions with a patient to affect a positive therapeutic outcome. Such techniques include, but are not limited to, behavior therapy, cognitive therapy, psychodynamic therapy, psychoanalytic therapy, group therapy, family counseling, art therapy, music therapy, vocational therapy, humanistic therapy, existential therapy, transpersonal therapy, client-centered therapy (also called person-centered therapy), Gestalt therapy, biofeedback therapy, rational emotive behavioral therapy, reality therapy, response-based therapy, Sandplay therapy, status dynamics therapy, hypnosis, and validation therapy. Psychotherapy may involve combining two or more techniques. A therapist can select and adjust the techniques based on the needs of the individual patient and the patient's response.

The term "muscarinic disorder" refers to any disease or condition ameliorated by activating the muscarinic system. Such diseases include ones in which direct activation of muscarinic receptors themselves or inhibition of cholinesterase enzymes has produced a therapeutic effect.

The terms "diseases related to schizophrenia" and "disorders related to schizophrenia" include, but are not limited to, schizo-affective disorder, psychosis, delusional disorders, psychosis associated with Alzheimer's disease, psychosis associated with Parkinson's disease, psychotic depression, bipolar disorder, bipolar with psychosis, Huntington's disease, Lewy Body dementia, or any other disease with psychotic features.

The term "movement disorders" includes, but is not limited to, Gilles de la Tourette's syndrome, Friederich's ataxia, Huntington's chorea, restless leg syndrome, and other diseases or disorders whose symptoms include excessive movements, tics, and spasms.

The term "mood disorders" includes major depressive disorder, dysthymia, recurrent brief depression, minor depression disorder, bipolar disorder, mania, and anxiety.

The term "cognitive disorders" refers to diseases or disorders marked by a cognitive deficit (e.g., having abnormal working memory, problem-solving abilities, etc.). Diseases include but are not limited to Alzheimer's disease, Parkinson's Disease, dementia (including, but not limited to, AIDS-related dementia, vascular dementia, age-related dementia, dementia associated with Lewy bodies, and idiopathic dementia), Pick's disease, tauopathies, synucleinopathies, confusion, cognitive deficit associated with fatigue, learning disorders, traumatic brain injury, autism, age-related cognitive decline, and Cushing's Disease, a cognitive impairment associated with autoimmune diseases.

The term "attention disorders" refers to diseases or conditions marked by having an abnormal or decreased attention span. Diseases include, but are not limited to, attention deficit and hyperactivity disorder (ADHD), attention deficit disorder (ADD), Dubowitz Syndrome, FG Syndrome, Down's Syndrome, growth delay due to insulin-like growth factor I (IGF1) deficiency, hepatic encephalopathy syndrome, and Strauss Syndrome.

The term "addictive disorders" refers to diseases or conditions marked by addiction or substance dependence as defined by the Diagnostic & Statistical Manual V (DSM-5). Such disorders are characterized by physical dependence, withdrawal, and tolerance to a substance. Such substances include but are not limited to alcohol, cocaine, amphetamines, opioids, benzodiazepines, inhalants, nicotine, barbiturates, cocaine, and *cannabis*. Addictive disorders also encompass behaviors that a patient does compulsively or continually despite clear negative consequences. For instance, ludomania (gambling addiction or compulsive gambling) is recognized by those skilled in the art as being an addictive behavior that often has devastating consequences. In certain embodiments, the addictive behavior may be Internet Gaming Disorder (gaming addiction), as defined in the DSM-5.

The term "pain" refers to physical suffering or discomfort caused by illness or injury. Pain is a subjective experience, and the perception of pain is performed as part of the central nervous system (CNS). Usually, noxious (peripheral) stimuli are transmitted to the CNS beforehand, but the pain is not always associated with nociception. A broad variety of clinical pain exists, derived from different underlying pathophysiological mechanisms, and needs different treatment approaches. Three major types of clinical pain have been characterized: acute pain, chronic pain, and neuropathic pain.

Acute clinical pain may result, for example, from inflammation or soft tissue injury. This type of pain is adaptive and has the biologically relevant function of warning and enabling healing and repair of an already damaged body part to occur undisturbed. A protective function is achieved by making the injured or inflamed area and surrounding tissue hypersensitive to all stimuli so that contact with any external stimulus can be avoided. The neuronal mechanisms underlying this type of clinical pain are well understood, and pharmacological control of acute clinical pain is available and effective, for example, by means of nonsteroidal anti-inflammatory drugs (NSAIDs) up to opioids depending on the type and extent of the sensation of pain.

Chronic clinical pain appears as sustained sensory abnormalities resulting from an ongoing peripheral pathology such as cancer or chronic inflammation (e.g., arthritis), or it can be independent of such initiating triggers. Chronic pain independent of initiating triggers is maladaptive, offering no survival advantage, and very often, no effective treatment is available.

Neuropathic pain can be classified as peripheral or central. Peripheral neuropathic pain is caused by injury or infection of peripheral sensory nerves, whereas central neuropathic pain is caused by damage to the CNS or/and the spinal cord. Both peripheral and central neuropathic pain can occur without obvious initial nerve damage.

The term "activator" means a molecule described as an agonist, partial agonist, co-agonist, physiological agonist, potentiator, stimulator, allosteric potentiator, positive allosteric modulator, allosteric agonist, or a molecule that increases the activity or signaling of receptors directly or indirectly.

The term "inhibitor" means a molecule described as an antagonist, partial antagonist, competitive antagonist, non-competitive antagonist, uncompetitive antagonist, silent antagonist, inverse agonist, reversible antagonist, physiological antagonist, irreversible antagonist, inhibitor, reversible inhibitor, irreversible inhibitor, negative allosteric modulator, allosteric antagonist, or a molecule that decreases the activity or signaling of receptors directly or indirectly.

The term "maximum tolerated dose" means the highest dose of a drug or therapeutic that a patient can take without the patient experiencing intolerable side effects. The maximum tolerated dose is typically determined empirically in clinical trials.

The term "muscarinic receptors" refers to G-protein linked receptors that bind the neurotransmitter acetylcholine. To date, five subtypes of the muscarinic receptor have been identified. "M1" means the subtype one muscarinic receptor. "M2" means the subtype two muscarinic receptor. "M3" means the subtype three muscarinic receptor. "M4" means the subtype four muscarinic receptor. "M5" means the subtype five muscarinic receptor.

The term "antipsychotic" refers to a drug that diminishes psychosis, hallucinations, or delusions. Antipsychotics include, but are not limited to haloperidol, droperidol, chlorpromazine, fluphenazine, perphenazine, prochlorperazine, thioridazine, trifluoperazine, mesoridazine, periciazine, promazine, triflupromazine, levomepromazine, promethazine, pimozide, chlorprothixene, flupenthixol, thiothixene, zuclopenthixol, clozapine, olanzapine, risperidone, quetiapine, ziprasidone, amisulpride, asenapine, paliperidone, zotepine, aripiprazole, bifeprunox, and tetrabenazine.

The term "anxiolytics" refers to drugs that reduce anxiety, fear, panic, or related feelings. Such drugs include, but are not limited to, benzodiazepines (e.g., alprazolam, chlordiazepoxide, clonazepam, clorazepate, diazepam, lorazepam), buspirone, barbiturates (e.g., amobarbital, pentobarbital, secobarbital, phenobarbital), and hydroxyzine.

The term "anti-depressants" refers to drugs that alleviate depression and related conditions (e.g., dysthymia). Such drugs include, but are not limited to, selective serotonin-reuptake inhibitors (SSRIs, e.g., citalopram, escitalopram, fluoxetine, fluvoxamine, paroxetine, sertraline), serotonin-norepinephrine reuptake inhibitors (SNRIs, e.g., desvenlafaxine, duloxetine, milnacipran, venlafaxine), mianserin, mirtazapine, norepinephrine reuptake inhibitors (e.g., atomoxetine, mazindol, reboxetine, viloxazine), bupropion, tianeptine, agomelatine, tricyclic antidepressants (e.g., amitriptyline, clomipramine, doxepin, imipramine, trimipramine, desipramine, nortriptyline, protriptyline), and monoamine oxidase inhibitors (e.g., isocarboxazid, moclobemide, phenelzine, selegiline, tranylcypromine).

The terms "sedatives" or "tranquilizers" refer to drugs that induce somnolence, promote a feeling of being tired or desire to sleep, or promote a state of unconsciousness. Such drugs include, but are not limited to, benzodiazepines, barbiturates (e.g., amobarbital, pentobarbital, secobarbital, phenobarbital), eszopiclone, zaleplon, zolpidem, and zopiclone.

Pharmaceutical Compositions

Earlier development of xanomeline, a muscarinic receptor agonist, as monotherapy was halted due to peripheral cholinergic side effects. The current disclosure provides a dosage form with dissolution kinetics having a more effective therapeutic effect for both active ingredients, enhanced pharmacokinetics for trospium chloride, and greater dosing compliance. The current disclosure also provides dosage forms with different strengths and/or different ratios of the two actives.

Provided herein is an oral pharmaceutical composition, comprising a plurality of xanomeline beads comprising xanomeline or a salt thereof; and a plurality of trospium beads comprising a salt of trospium. In certain embodiments, the plurality of xanomeline beads has a core comprising xanomeline or a salt thereof. In certain embodiments, the plurality of trospium beads has a core comprising a trospium salt.

In certain embodiments, a capsule shell comprising hydroxypropyl methylcellulose (HPMC) containing separate populations of drug beads containing xanomeline tartrate or trospium chloride wherein the drug beads are of comparable size and release the actives rapidly and at substantially similar rates. Following the dissolution of the capsule shell in the stomach, the drug beads may dissolve in the stomach and/or pass through the pyloric valve into the duodenum intact or partially intact, but the ratio of the two drugs, both in dissolved form and in undissolved form remains relatively constant in the gastrointestinal tract until the drugs are absorbed.

The formulation for each drug bead allows substantially similar performance from two actives at different dose ranges, where the actives are released into the blood serum at substantially similar rates and/or achieve a substantially similar $T_{max}$. In certain embodiments, a capsule containing 50 mg xanomeline as the tartrate salt and 10 mg trospium chloride. Because 50 mg xanomeline as free base corresponds to about 76 mg xanomeline tartrate, the ratio of the active ingredients in such a formulation is about 7.6 to 1.

A discrepancy in the number of drug beads in the capsule increases the probability that the ratio of drug beads would not remain substantially constant after the beads are released and disperse. Thus, in certain embodiments, the trospium beads are formulated with a lower drug load such that effective doses of trospium and of xanomeline are contained in roughly equivalent numbers of beads. In certain embodiments, despite the differences in drug loads, the trospium and xanomeline beads release at roughly similar rates. For example, if the dissolution of the capsules is assessed using a United States Pharmacopeia (USP) dissolution apparatus, the percentage of xanomeline dissolved is substantially equivalent to the percentage of dissolved trospium chloride, such as at 10 min, 20 min, or 30 min.

The medicament may also include one or more pharmaceutically acceptable salts. The medicament may include one or more pharmaceutically-acceptable carriers. The medicament may be administered orally. The medicament may be delivered orally using tablets, troches, liquids, emulsions, suspensions, drops, capsules, caplets or gel caps, and other methods of oral administration known to one skilled in the art.

The medicament may be in a dosage form that immediately releases the drug. In an alternative embodiment, the medicament may have a controlled release dosage form.

The medicament may be in dosage forms that use other methods of controlled release formulation known to one in the art.

In another embodiment, the medicament is combined with one or more therapies, including psychotherapy and drugs. Therapeutic agents include, but are not limited, to antipsychotics, anxiolytics, anti-depressants, sedatives, tranquilizers, analgesics, and other pharmacological interventions known to one skilled in the art. A therapeutic agent may fall under the category of more than one drug. For instance, benzodiazepines can be considered anxiolytics, sedatives, and tranquilizers.

Bead/Core Excipients

The bead and/or core can comprise one or more excipients. In one embodiment, the excipients include one or more fillers, binders, and surfactants. Other optional ingredients include, but are not limited to, glidants, lubricants, disintegrants, swelling agents, and antioxidants. The xanomeline or a pharmaceutically acceptable salt thereof and the salt of trospium may be in separate matrices within the same medicament.

The amount of xanomeline free base in the core can be at least 10 wt. % or at least 15 wt. %, or at least 20 wt. %, or at least 25 wt. %, or at least 30 wt. %. For example, the amount of xanomeline tartrate can be at least 50 wt. %, or at least 55 wt. %, or at least 60 wt. %, or at least 65 wt. %, or at least 70 wt. %, or at least 75 wt. %, or at least 80 wt. %, or at least 85 wt. % of the core, for example in a range of about 60 wt. % to about 90 wt. % or about 65 wt. % to about 85 wt. %. It is understood that all ranges including these values as endpoints are contemplated, for example, at least between about 15 wt. % and about 90 wt. %, between about 20 wt. % and about 85 wt. %, between about 30 wt. % and about 85 wt. %, or between about 50 wt. % and about 90 wt. %. In certain embodiments, the xanomeline beads comprise between 30 wt. % and 80 wt. % xanomeline tartrate, such as 66 wt. % xanomeline tartrate.

The amount of trospium salt in the core can be at least 10 wt. % or at least 15 wt. %, or at least 20 wt. %, or at least 25 wt. %, or at least 30 wt. %. For example, the amount of trospium chloride can be at least 50 wt. %, or at least 55 wt. %, or at least 60 wt. %, or at least 65 wt. %, or at least 70 wt. %, or at least 75 wt. %, or at least 80 wt. %, or at least 85 wt. % of the core, for example in a range of about 60 wt. % to about 90 wt. % or about 65 wt. % to about 85 wt. %. It is understood that all ranges including these values as endpoints are contemplated, for example, at least between about 15 wt. % and about 90 wt. %, between about 20 wt. % and about 85 wt. %, between about 30 wt. % and about 85 wt. %, or between about 50 wt. % and about 90 wt. %. In certain embodiments, the trospium is trospium chloride. In certain embodiments, the trospium beads comprise between 8 wt. % and 35 wt. % trospium chloride, such as 17.7 wt. % trospium chloride.

In a further embodiment, the matrix comprises a polymer, for example, to modify the release profile of the active in the matrix. In a further embodiment, the polymer comprises a water-soluble polymer. In a further embodiment, the water-soluble polymer is selected from Eudragit™ RL, polyvinyl alcohol, polyvinylpyrrolidone, methylcellulose, hydroxypropyl cellulose, hydroxypropylmethylcellulose, polyethylene glycol, and mixtures thereof. In a further embodiment, the polymer comprises a water-insoluble polymer. In a further embodiment, the water-insoluble polymer is selected from Eudragit™ RS, ethylcellulose, cellulose acetate, cellulose propionate, cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), poly(ethylene), poly(ethylene) low density, poly(ethylene) high density, poly(propylene), poly(ethylene terephthalate), poly(vinyl isobutyl ether), poly(vinyl acetate), poly(vinyl chloride), polyurethane, and mixtures thereof.

Fillers include, but are not limited to, lactose, saccharose, glucose, starch, microcrystalline cellulose, microfine cellulose, mannitol, sorbitol, calcium hydrogen phosphate, aluminum silicate, amorphous silica, and sodium chloride, starch, and dibasic calcium phosphate dihydrate. In one embodiment, the filler is not water-soluble, although it may absorb water. In one embodiment, the filler is a spheronization aid. Spheronization aids can include one or more of crospovidone, carrageenan, chitosan, pectinic acid, glycerides, β-cyclodextrin (β-CD), cellulose derivatives, microcrystalline cellulose, powdered cellulose, polyplasdone crospovidone, and polyethylene oxide. In one embodiment, the filler includes microcrystalline cellulose.

The amount of filler in the xanomeline core is not particularly limited. In embodiments, the amount of filler (e.g., microcrystalline cellulose) can be in a range of about 10 wt. % to about 70 wt. %, or about 16 wt. % to about 23 wt. %, or at least 19 wt. % or at least 19.5 wt. %, for example, about 20 wt. %. In certain embodiments, the xanomeline beads comprise between 15 wt. % and 65 wt. % microcrystalline cellulose, such as between about 15 wt. % and 20 wt. %, between about 20 wt. % and 25 wt. %, between about 25 wt. % and 30 wt. %, between about 30 wt. % and 35 wt. %, between about 35 wt. % and 40 wt. %, between about 40 wt. % and 45 wt. %, between about 45 wt. % and 50 wt. %, between about 50 wt. % and 55 wt. %, between about 55 wt. % and 60 wt. %, or between about 60 wt. % and 65 wt. %. In certain embodiments, the xanomeline beads comprise 33.5 wt. % microcrystalline cellulose.

The amount of filler in the trospium core is not particularly limited. In embodiments, the amount of filler (e.g., microcrystalline cellulose or lactose) can be in a range of about 10 wt. % to about 80 wt. %, or about 16 wt. % to about 23 wt. %, or at least 19 wt. % or at least 19.5 wt. %, for example about 20 wt. %. In certain embodiments, the trospium beads comprise between 25 wt. % and 80 wt. % microcrystalline cellulose, such as between about 25 wt. % and 30 wt. %, between about 30 wt. % and 35 wt. %, between about 35 wt. % and 40 wt. %, between about 40 wt. % and 45 wt. %, between about 45 wt. % and 50 wt. %, between about 50 wt. % and 55 wt. %, between about 55 wt. % and 60 wt. %, between about 60 wt. % and 65 wt. %, between about 65 wt. % and 70 wt. %, between about 70 wt. % and 75 wt. %, or between about 75 wt. % and 80 wt. %. In certain embodiments, the trospium beads comprise 46.8 wt. % microcrystalline cellulose.

In certain embodiments, the trospium beads comprise between 15 wt. % and 70 wt. % lactose monohydrate, such as between about 15 wt. % and 20 wt. %, between about 20 wt. % and 25 wt. %, between about 25 wt. % and 30 wt. %, between about 30 wt. % and 35 wt. %, between about 35 wt.

% and 40 wt. %, between about 40 wt. % and 45 wt. %, between about 45 wt. % and 50 wt. %, between about 50 wt. % and 55 wt. %, between about 55 wt. % and 60 wt. %, between about 60 wt. % and 65 wt. %, or between about 65 wt. % and 70 wt. %. In certain embodiments, the trospium beads comprise 35 wt. % lactose monohydrate.

Binders include, but are not limited to, cellulose ethers, methylcellulose, ethylcellulose, hydroxyethylcellulose, propyl cellulose, hydroxypropyl cellulose, lower-substituted hydroxypropyl cellulose, hydroxypropylmethylcellulose (hypromellose, e.g., hypromellose 2910, Methocel™ E), carboxymethyl cellulose, starch, pregelatinized starch, acacia, tragacanth, gelatin, polyvinyl pyrrolidone (povidone), cross-linked polyvinyl pyrrolidone, sodium alginate, microcrystalline cellulose, and lower-alkyl-substituted hydroxypropyl cellulose. In one embodiment, the binders are selected from wet binders. In one embodiment, the binder is selected from cellulose ethers, e.g., hypromellose.

The amount of binder in the xanomeline core is not particularly limited. In embodiments, the amount of binder (e.g., hypromellose) can be in a range between about 1 wt. % and about 10 wt. %, between about 2 wt. % and about 8 wt. %, or between about 4 wt. % and about 6 wt. %, for example, about 5 wt. %.

The amount of binder in the trospium core is not particularly limited. In embodiments, the amount of binder (e.g., hypromellose) can be in a range between about 1 wt. % and about 10 wt. %, between about 2 wt. % and about 8 wt. %, or between about 4 wt. % and about 6 wt. %, for example, about 5 wt. %.

Surfactants include, but are not limited to, anionic surfactants, including sodium lauryl sulfate, sodium deoxycholate, dioctyl sodium sulfosuccinate, and sodium stearyl fumarate, nonionic surfactants, including polyoxyethylene ethers, and polysorbate 80, and cationic surfactants, including quaternary ammonium compounds. In one embodiment, the surfactant is selected from anionic surfactants, e.g., sodium lauryl sulfate.

The amount of surfactant, e.g., as a processing aid, in the xanomeline core, is not particularly limited. In embodiments, the amount of surfactant (e.g., microcrystalline cellulose) can be in a range between about 0.1 wt. % and about 1 wt. %, between about 0.2 wt. % and about 0.8 wt. %, or between about 0.4 wt. % and about 0.6 wt. %, for example, about 0.5 wt. %.

The amount of surfactant, e.g., as a processing aid, in the trospium core, is not particularly limited. In embodiments, the amount of surfactant (e.g., sodium lauryl sulfate) can be in a range between about 0.1 wt. % and about 1 wt. %, between about 0.2 wt. % and about 0.8 wt. %, or between about 0.4 wt. % and about 0.6 wt. %, for example, about 0.5 wt. %.

Disintegrants include, but are not limited to, starch, sodium cross-linked carboxymethyl cellulose, carmellose sodium, carmellose calcium, cross-linked polyvinyl pyrrolidone, and sodium starch glycolate, low-substituted hydroxypropyl cellulose, and hydroxypropyl starch.

Glidants include, but are not limited to, polyethylene glycols of various molecular weights, magnesium stearate, calcium stearate, calcium silicate, fumed silicon dioxide, magnesium carbonate, magnesium lauryl sulfate, aluminum stearate, stearic acid, palmitic acid, cetanol, stearol, and talc.

Lubricants include, but are not limited to, stearic acid, magnesium stearate, calcium stearate, aluminum stearate, and siliconized talc. In certain embodiments, the xanomeline beads comprise between 0 wt. % and 2 wt. % talc, such as 0.5 wt. % talc. In certain embodiments, the trospium beads comprise between 0 wt. % and 2 wt. % talc, such as 0.5 wt. % talc.

In certain embodiments, the formulation further comprises one or more antioxidants. Examples of pharmaceutically-acceptable antioxidants include (1) water-soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediaminetetra-acetic acid (EDTA), sorbitol, tartaric acid, phosphoric acid, and the like. In certain embodiments, the formulation comprises less than 1 wt. % antioxidant, such as 0.9 wt. %, 0.8 wt. %, 0.7 wt. %, 0.6 wt. %, 0.5 wt. %, 0.4 wt. %, 0.3 wt. %, 0.2 wt. %, 0.1 wt. %, 0.09 wt. %, 0.08 wt. %, 0.07 wt. %, 0.06 wt. %, 0.05 wt. %, 0.04 wt. %, 0.03 wt. %, 0.02 wt. %, or 0.01 wt. %. In certain embodiments, the formulation comprises about 0.05 wt. % BHT or 0.5 wt. % ascorbic acid. In certain embodiments, the antioxidant is present in the xanomeline core or the xanomeline beads.

In certain embodiments, the xanomeline beads comprise between 30 wt. % and 80 wt. % xanomeline tartrate, between 15 wt. % and 65 wt. % microcrystalline cellulose, and between 0 wt. % and 2 wt. % talc. In certain embodiments, the trospium beads comprise between 0.2 wt. % and 2 wt. % talc, such as 0.5 wt. % talc. In certain embodiments, the trospium beads comprise between 8 wt. % and 35 wt. % trospium chloride, between 25 wt. % and 80 wt. % microcrystalline cellulose, between 15 wt. % and 70 wt. % lactose monohydrate, and between 0.2 wt. % and 2 wt. % talc.

In certain embodiments, the xanomeline tartrate drug beads comprise 66 wt. % xanomeline tartrate, 33.5 wt. % microcrystalline cellulose, and 0.5 wt. % talc. In certain embodiments, the trospium chloride beads comprise 17.7 wt. % trospium chloride, 46.8 wt. % microcrystalline cellulose, 35 wt. % lactose monohydrate, and 0.5 wt. % talc. In this example, the xanomeline tartrate beads contain about 2.5 times as much xanomeline as the trospium chloride beads contain trospium chloride.

Depending on dosing requirements, capsules can be prepared with different amounts of xanomeline tartrate and trospium chloride beads. In various embodiments, capsules contain 50 mg xanomeline and 10 mg trospium chloride, 50 mg xanomeline and 20 mg trospium chloride, 75 mg xanomeline and 10 mg trospium chloride, 75 mg xanomeline and 20 mg trospium chloride, 125 mg xanomeline and 30 mg trospium chloride, or 125 mg xanomeline and 40 mg trospium chloride. In certain embodiments, the capsule contains 25 mg xanomeline as xanomeline tartrate and 10 mg trospium chloride. In certain embodiments, the capsule contains 50 mg xanomeline as xanomeline tartrate and 10 mg trospium chloride. In certain embodiments, the capsule contains 50 mg xanomeline as xanomeline tartrate and 20 mg trospium chloride. In certain embodiments, the capsule contains 75 mg xanomeline as xanomeline tartrate and 10 mg trospium chloride. In certain embodiments, the capsule contains 75 mg xanomeline as xanomeline tartrate and 20 mg trospium chloride. In certain embodiments, the capsule contains 125 mg xanomeline as xanomeline tartrate and 20 mg trospium chloride. In certain embodiments, the capsule contains 125 mg xanomeline as xanomeline tartrate and 40 mg trospium chloride.

In another embodiment, the medicament contains from five milligrams to 700 milligrams of xanomeline. In an embodiment, the medicament contains from 25 milligrams to 300 milligrams of xanomeline.

In another embodiment, the medicament contains from one milligram to 400 milligrams of trospium chloride. In an embodiment, the medicament contains from 6.5 milligrams to 200 milligrams of trospium chloride.

In one embodiment, trospium chloride extended-release is used as the trospium chloride in the medicament. In another embodiment, the medicament contains from one milligram to 400 milligrams of trospium chloride extended-release. In an embodiment, the medicament contains from 6.5 milligrams to 200 milligrams of trospium chloride extended-release.

In an embodiment, the medicament contains 75 mg or 225 milligrams of xanomeline, and the same medicament contains 20 mg or 40 milligrams of trospium chloride. In another embodiment, the medicament contains 75 mg or 225 milligrams of xanomeline, and a different medicament to be co-administered contains 20 mg or 40 milligrams of trospium chloride.

Bead Coatings

In other embodiments, the beads may be coated with functional or non-functional coatings, for example, for aesthetic, handling, or stability. In certain embodiments, the beads might be coated with a pH-sensitive coating so that they do not dissolve in the low pH of the stomach. A nonfunctional coating might be used to maintain chemical separation between the beads or for cosmetic reasons.

In a further embodiment, the controlled release formulation comprises a semi-permeable coating. The xanomeline and trospium chloride may be in different coatings in the same formulation. In another embodiment, the xanomeline and trospium chloride can be in different coatings in different formulations or dosing vehicles. In a further embodiment, the semi-permeable coating comprises a polymer. In a further embodiment, the controlled release formulation comprises a matrix that suspends the xanomeline and trospium chloride.

In certain embodiments, the distribution of coating thicknesses can be stated in the weight gain of coating material based on the total weight of the coated beads. Thus, in one embodiment, the distribution of coating thicknesses is at least 2% based on the total weight of the coated beads. In another embodiment, the distribution of coating thicknesses is at least 3%. In another embodiment, the distribution of coating thicknesses is at least 4%. In another embodiment, the distribution of coating thicknesses is at least 5%. In another embodiment, the distribution of coating thicknesses is at least 6%. In another embodiment, the distribution of coating thicknesses is at least 7%. In another embodiment, the distribution of coating thicknesses is at least 8%. In another embodiment, the distribution of coating thicknesses is at least 9%. In another embodiment, the distribution of coating thicknesses is at least 10%. In another embodiment, the distribution of coating thicknesses is at least 11%. In another embodiment, the distribution of coating thicknesses is at least 12%. In another embodiment, the distribution of coating thicknesses is at least 13%. In another embodiment, the distribution of coating thicknesses is at least 14%.

For example, the difference in coating thickness from bead to bead can be in a range of +/−1-7% based on the total weight of the coated beads. The distribution of coating thicknesses can between about 2% and about 14% based on the weight of the coated beads, such as between about 3% and about 13%, between about 4% and about 12%, between about 5% and about 11%, between about 6% to about 10%, between about 7% and 9%, between about 3% and 14%, between about 4% and 14%, between about 4% and 13%, or between 4% and about 12%.

In one embodiment, the absorption (area under the curve, AUC) of the dosage form when dosed orally is advantageously increased, compared to other dosage forms of xanomeline or trospium chloride. Without intending to be bound by any theory, the increase in absorption is influenced by the dosage form exhibiting a pseudo-extended release profile. The pseudo-extended release profile is influenced by one or more factors, including distribution of coating thicknesses when present, distribution of bead particle sizes, and the beads having irregular bead shapes. For example, in an embodiment wherein the beads have a distribution of coating thicknesses, for beads with a relatively thin coating, the coating completely dissolves at the trigger pH relatively quickly to release the xanomeline and/or trospium chloride compositions, whereas for beads having a relatively thick coating the coating takes somewhat longer to completely dissolve and release the xanomeline and/or trospium chloride compositions. In an embodiment where the beads have a distribution of particle sizes and/or irregular bead shapes, the gut transit time of the beads could be varied due to bead size and/or shape, such that the transit time until reaching the coating dissolution pH is varied, thus contributing to a pseudo-extended release profile. In another embodiment, the dosage form exhibits substantially equivalent (e.g., bioequivalent) $C_{max}$ and/or AUC characteristics when administered orally inside a capsule shell or without a capsule shell.

In certain embodiments, the dosage form provides a progressive and predictable absorption curve. In one embodiment, the $T_{max}$ of the dosage form when dosed orally is more stable on a dose-to-dose basis because the beads are individually coated. A predictable, consistent $T_{max}$ is advantageous for accomplishing a more consistent, sustained therapeutic effect. For example, process-related variations in coating thickness or other influences on coating dissolution affect only a fraction of the xanomeline and trospium chloride in the dosage form and tend to lead to the pseudo-extended release behavior. In contrast, coated capsules comprising xanomeline and trospium chloride microspheres exhibit significant variability in absorption time from capsule to capsule.

In certain embodiments, the oral pharmaceutical composition comprises xanomeline and/or a salt thereof and trospium chloride for treating a muscarinic disorder in a patient in need thereof, which when administered to the patient in need thereof, the composition is sufficient to provide an in-vivo plasma profile comprising a median $T_{max}$ for xanomeline of 2 hours and a median $T_{max}$ for trospium of 1 hour. In certain embodiments, the in-vivo plasma profile further comprises a mean dose-normalized $C_{max}$ of between 48.5 and 121.3 pg/mL/mg. In certain embodiments, the in-vivo plasma profile further comprises a mean dose-normalized $C_{max}$ of trospium of between 156 and 375 pg/mL/mg. In certain embodiments, the in-vivo plasma profile further comprises a mean dose-normalized $AUC_{0-12}$ of xanomeline of between 263 and 577 hr·pg/mL/mg. In certain embodiments, the in-vivo plasma profile further comprises a mean dose-normalized $AUC_{0-12}$ of trospium of between 881 and 2024 hr·pg/mL/mg. In certain embodiments, the in-vivo plasma profile further comprises a mean $C_{max}$ of trospium at 7850±3360 pg/mL. In certain embodiments, the in-vivo plasma profile further comprises a mean $AUC_{0-12}$ of 41900±15500 hr·pg/mL.

In another embodiment, the dosage form exhibits advantageous storage stability, e.g., as measured by the amount of xanomeline present following storage and/or by the total amount of related substances. The storage stability can be assessed following storage at typical ambient conditions (e.g., 25° C. and 60% relative humidity) or at accelerated stability conditions involving increased temperature and/or humidity.

The dosage form and methods are contemplated to include embodiments of any combination of one or more of the additional optional elements, features, and steps further described below (including those shown in the figures and Examples) unless stated otherwise. Reference to a bead and properties thereof apply equally to a collection of beads (e.g., a plurality of such beads). Likewise, a reference to a core and properties thereof apply equally to a collection of cores (e.g., a plurality of such cores).

The enteric (gastro-resistant) coating material, e.g., polymer, can be one that will dissolve in intestinal juices at a pH level higher than that of the stomach, e.g., a pH of greater than 4.5, such as within the small intestine, and therefore permit the release of the active substance in the regions of the small intestine and substantially not in the upper portion of the GI tract. In one embodiment, the enteric material begins to dissolve in an aqueous solution at pH between about 4.5 and about 5.5. In another embodiment, the enteric material rapidly dissolves in an aqueous solution at a pH of about 5. In another embodiment, the enteric material rapidly dissolves in an aqueous solution at a pH of about 5.5.

For example, pH-sensitive materials do not significantly dissolve until the dosage form has emptied from the stomach. The pH of the small intestine gradually increases from about 4.5 to about 6.5 in the duodenal bulb to about 7.2 in the distal portions of the small intestine (ileum). To provide predictable dissolution corresponding to the small intestine transit time of about 3 hours (e.g., 2-3 hours) and permit reproducible release therein, the coating should begin to dissolve within the pH range of the duodenum and continue to dissolve at the pH range within the small intestine. Therefore, the amount (thickness) of enteric coating should be sufficient to be substantially dissolved during the about three-hour transit time within the small intestine (e.g., the proximal and mid-small intestine).

Suitable enteric (gastro-resistant) materials include, but are not limited to, cross-linked polyvinyl pyrrolidone; non-crosslinked polyvinylpyrrolidone; hydroxypropylmethyl cellulose phthalate, hydroxypropylmethyl cellulose acetate succinate, cellulose acetate succinate; cellulose acetate phthalate, hydroxypropylmethyl cellulose acetate succinate, cellulose acetate trimellitate; starch acetate phthalate; polyvinyl acetate phthalate; carboxymethyl cellulose; methyl cellulose phthalate; methyl cellulose succinate; methyl cellulose phthalate succinate; methyl cellulose phthalic acid half ester; ethyl cellulose succinate; carboxymethylamide; potassium methacrylate divinylbenzene copolymer; polyvinyl alcohols; polyoxyethylene glycols; polyethylene glycol; sodium alginate; galactomannan; carboxypolymethylene; sodium carboxymethyl starch; copolymers of acrylic acid and/or methacrylic acid with a monomer selected from the following: methyl methacrylate, ethyl methacrylate, ethyl acrylate, butyl methacrylate, hexyl methacrylate, decyl methacrylate, lauryl methacrylate, phenyl methacrylate, methyl acrylate, isopropyl acrylate, isobutyl acrylate, or octadecyl acrylate, e.g. Eudragit™-L and -S series, including L 100-55, L 30 D-55, L 100, S 100, L 12.5, and S 12.5, available from Evonik Industries; polyvinyl acetate; fats; oils; waxes; fatty alcohols; shellac; zein; gluten; ethylacrylate-maleic acid anhydride copolymer; maleic acid anhydride-vinyl methyl ether copolymer; styrol-maleic acid copolymer; 2-ethyl-hexyl-acrylate maleic acid anhydride; crotonic acid-vinyl acetate copolymer; glutaminic acid/glutamic acid ester copolymer; carboxymethylethylcellulose glycerol monooctanoate; polyarginine; poly(ethylene); poly (propylene); poly(ethylene oxide); poly(ethylene terephthalate); poly(vinyl isobutyl ether); poly(vinyl chloride); and polyurethane. A combination of enteric materials may also be used. In one embodiment, the enteric material rapidly dissolves at pH 5.5 and higher to provide fast dissolution in the upper bowel. For example, the enteric material can be selected from a copolymer of methacrylic acid and methyl methacrylate and a copolymer of methacrylic acid and ethyl acrylate. For example, an enteric polymer is poly(methacrylic acid co-ethyl acrylate) 1:1 (Eudragit™ L 30 D-55 and Eudragit™ L 100-55).

Other suitable examples of enteric coating coatings include beeswax and glyceryl monostearate; beeswax, shellac and cellulose; and cetyl alcohol, mastic and shellac, and shellac and stearic acid; polyvinyl acetate and ethyl cellulose; and neutral copolymer of polymethacrylic acid esters (Eudragit™ L 30D); copolymers of methacrylic acid and methacrylic acid methylester, or a neutral copolymer of polymethacrylic acid esters containing metallic stearates. Such coatings comprise mixtures of fats and fatty acids, shellac and shellac derivatives, and the cellulose acid phthalates, e.g., those having a free carboxyl content.

One or more plasticizers can be added to enteric polymers to increase their pliability and reduce brittleness, as known in the art. Suitable plasticizers include, for example, butyl citrates, triethyl citrate, diethyl phthalate, dibutyl sebacate, polyethylene glycols (PEGs, such as PEG 6000), acetyl triethyl citrate, and triacetin. In one embodiment, the plasticizer is triethyl citrate. While some enteric materials are flexible and do not require plasticizers, more brittle polymers (e.g., Eudragit™ L/S types, Eudragit™ RL/RS, and Eudragit™ FS 30 D) benefit from plasticizers, for example ranging from between 5 wt. % and 30 wt. % based on the dry polymer mass, between about 8 wt. % and about 12 wt. % triethyl citrate with poly(methacrylic acid co-ethyl acrylate) 1:1.

In certain embodiments, the enteric coatings comprise one or more anti-tacking agents (antiadherents) to reduce the tackiness of the film and prevent agglomeration, as it is known in the art. Suitable anti-tacking agents include, but are not limited to talc, glyceryl monostearate, fumed silica (e.g., Aerosil™ 200), precipitated silica (e.g., Sipernat™ PQ), and magnesium stearate. Anti-tacking agents can be used in any suitable quantity, for example ranging between about 10 wt. % and 100 wt. % based on dry polymer mass, between about 10 wt. % and about 50 wt. %, between about 10 wt. % and about 30 wt. %, or between about 15 wt. % and about 30 wt. %. For example, in one embodiment, it ranges between 15 wt. % and about 30 wt. % based on dry polymer mass.

One or more surfactants can also be added to an enteric coating mixture to increase substrate wettability and/or stabilize suspensions, as it is known in the art. Surfactants include Polysorbate 80, sorbitan monooleate, and sodium dodecyl sulfate, and other surfactants described herein.

The enteric coating can be formed by any suitable process. Coating processes include pan coating, fluid bed coating, and dry coating (e.g., heat dry coating and electrostatic dry coating), for example. Pan coating and fluid bed coating using solvent are well-established processes. In liquid coating, the enteric material and optional excipients (e.g., pigments, plasticizers, anti-tacking agents) are mixed in an organic solvent or water to form a solution or dispersion. The coating solution or dispersion is sprayed into solid dosage forms in a pan coater or a fluid bed dryer and dried by hot air. For example, in a Wurster fluid bed coating process, the coating fluid is sprayed from the bottom of the fluid bed apparatus. Alternatively, the coating fluid is applied by top spraying. In certain embodiments, a tangential spray is applied.

The amount of enteric material applied is sufficient to achieve the desired acid resistance and release characteristics. For example, in one embodiment, the amount of enteric coating meets USP<711> requirements (USP 36-NF 31) for delayed-release dosage forms, thereby not releasing 10.0 wt. % of the drug after 2 hours in 0.1 N HCl. In certain embodiments, the formulation releases at least 80% of the active in 20 minutes in pH 6.8 buffer solution, e.g., using a dissolution method of USP 36-NF 31 section<711>.

In one embodiment, the enteric coating is present in an amount in a range between about 10% and 40%, or between 25% and about 35% as measured by the weight gain compared to the uncoated particle cores, or ranging between about 25% and about 31% weight gain, between about 27% and about 31% weight gain, or between about 28.5% and about 31% weight gain, based on the weight of the uncoated particle cores.

The formulation can include a capsule shell in which the beads are disposed. Soft and hard capsule shells are known. In one embodiment, the capsule shell is a hard-capsule shell, e.g., a gelatin capsule shell or a vegetable-based hard capsule shell. In certain embodiments, the capsule shell comprises one or more enteric coatings described herein. During accelerated storage, gelatin capsules may collapse. Thus, in certain embodiments, the formulation can include a hydroxypropylmethylcellulose capsule shell.

Thus, for example, one embodiment combining various of the features described above includes a pharmaceutical dosage form comprising a plurality of xanomeline beads, the beads comprising a core comprising xanomeline tartrate, a filler (optionally microcrystalline cellulose), a binder (optionally hypromellose), and an enteric coating (optionally Eudragit™ L 30 D-55) surrounding the core, wherein the plurality of beads has a distribution of particle sizes ranging between about 0.7 mm and about 2.5 mm, wherein the enteric coating ranges between about 20% and about 40% based on the weight of the bead cores, and wherein the beads are disposed in a capsule shell.

Bead Size and Shape

The plurality of beads has a distribution of particle sizes. The plurality of beads has bead shapes. The plurality of beads has a distribution of coating thicknesses when present.

Beads having a distribution of particle sizes were shown to exhibit advantageous pharmacokinetics. Without intending to be bound by any theory, it is contemplated that the pharmacokinetics are influenced by the plurality of beads having a distribution of core sizes.

In one embodiment, the particle sizes of the beads range between about 0.4 mm and about 1.2 mm, such as between about 0.4 mm and about 0.5 mm, between about 0.5 mm and about 0.6 mm, between about 0.6 mm and about 0.7 mm, between about 0.7 mm and about 0.8 mm, between about 0.8 mm and about 0.9 mm, between about 0.9 mm and about 1.0 mm, between about 1.0 mm and about 1.1 mm, or between about 1.1 mm and about 1.2 mm. In certain embodiments, the size of the xanomeline beads is between about 0.425 mm and about 1.18 mm. In certain embodiments, the size of the xanomeline beads is between about 0.6 mm and about 0.85 mm. In certain embodiments, the size of the trospium beads is between about 0.425 mm and about 1.18 mm. In certain embodiments, the size of the trospium beads is between about 0.6 mm and about 0.85 mm.

The beads or bead mixtures may be used, for example, in suspensions, filled into capsules, compressed into tablets, or filled into sachets. One or more types of modified release beads can be mixed together and encapsulated or used as a sprinkle on the subject's food. In certain embodiments, the oral solid dosage form may be any of these forms. In certain embodiments, the dosage form is a capsule.

As the particle size of the beads becomes too small, the variability in the content of the active increases. As the particle size becomes too large, the beads are too large for drug products labeled to be administered via sprinkling (e.g., on applesauce or other soft foods, such as jellies) and swallowed without chewing or administered via an enteral feeding tube. Also, as the particle size increases, the larger particles get coated more than the smaller particles, resulting in lower relative assay compared to smaller particles. To compensate, relatively more beads are needed to meet the label strength per capsule. Filling a capsule shell with sufficient large particles to meet the label strength per capsule becomes difficult or impossible (e.g., to fill a size 0 capsule to a 75-mg strength of xanomeline free base).

In one embodiment, the beads are formulated into capsules, e.g., with an encapsulation machine. Various capsule sizes may accommodate the strength and fill weight of the target formulations. Capsule size ranges from 00 to 5 for fill weights ranging between about 15 mg and about 630 mg.

The beads can be sorted (e.g., via sieving) to the desired particle size. In certain embodiments, the particle size range is any particle size range or combination thereof described above regarding the cores. In one embodiment, the particle size range is the same as the particle size range of the uncoated cores. For example, the beads can be sieved such that 5% or less of the bead cores by weight is retained on a #12 mesh (1.68 mm) screen, and 10% or less by weight pass through a #20 mesh (0.84 mm) screen.

Method of Making

Provided is a method for preparing an oral pharmaceutical composition comprising admixing beads comprising a plurality of xanomeline beads comprising xanomeline or a pharmaceutically acceptable salt thereof with a plurality of trospium beads comprising a salt of trospium, such as trospium chloride. In certain embodiments, the method further comprises formulating the admixed beads into capsules.

Also disclosed herein are a method for preparing the dosage form, comprising coating a core comprising xanomeline or a pharmaceutically acceptable salt thereof and an excipient with an enteric polymer to form the enteric coating, and coating a core comprising trospium chloride or a pharmaceutically acceptable salt thereof and an excipient with an enteric polymer to form the enteric coating. Optionally, the core can be formed by a wet granulation method. Optionally, drug beads are sorted (e.g., via sieving) to a desired particle size range before enteric coating, and optionally again following enteric coating.

The drug beads may be made by different processes, including, but not limited to, spheronizing an extruded wet mass and coating of inert core spheres in a fluidized bed. In certain embodiments, the beads are prepared by extrusion and spheronization.

The beads are formulated to flow freely and to be compatible with modern encapsulation equipment. In some embodiments, the beads are blended together to form a uniform mixture that can be filled into capsules in a single stage. In other embodiments, the beads are filled separately into capsules using a two-stage capsule filler.

The cores comprising xanomeline or pharmaceutically acceptable salts thereof can be formed by any suitable process. In one embodiment, the core is formed by granulating a mixture of xanomeline or a pharmaceutically acceptable salt thereof with an excipient and milling to a desired particle size range. In another embodiment, the core can be formed by extrusion and spheronization of a mixture of xanomeline or a pharmaceutically acceptable salt thereof with an excipient.

The cores comprising trospium chloride or pharmaceutically acceptable salts thereof can be formed by any suitable process. In one embodiment, the core is formed by granulating a mixture of trospium chloride or a pharmaceutically acceptable salt thereof with an excipient and milling to a desired particle size range. In another embodiment, the core can be formed by extrusion and spheronization of a mixture of trospium chloride or a pharmaceutically acceptable salt thereof with an excipient.

Granulating processes can include fluid bed granulation, wet granulation, hot melt granulation, and spray congealing, for example. Other processes include slugging and roller compaction. The mixtures to be granulated can first be dry-blended. The dry-blended dry ingredients can be mixed with water before extrusion.

Extrusion and spheronization of a mixture of xanomeline or a pharmaceutically acceptable salt thereof and trospium chloride with an excipient provide desirable cores with a distribution of particle sizes as described herein and one or more other desirable properties. In certain embodiments, short processing times can lead to a more stable product. For example, reducing spheronization reduces friction and related heat. Reducing the time that the product is exposed to air (either when moist and/or before packaging) also diminishes oxidation. On the other hand, rapid processing by extrusion and spheronization can lead to a poor-quality product, for example, in having a large fraction of the bead cores falling outside a desired particle size range. The moisture absorbed by spheronization aids (which happens over time) influences the spheronization characteristics of the beads.

Accordingly, in one embodiment, the moisture content of the granulation mixture, before drying, ranging between about 20 wt. % and about 40 wt. %, such as between 25 wt. % and about 35 wt. %, between about 28 wt. % and about 32 wt. %, at least about 28 wt. %, at least about 28.5, between about 20 wt. % and about 40 wt. %, between about 25 wt. % and about 35 wt. %, between about 27 wt. % and about 31 wt. %, or between about 28.5 wt. % and about 31 wt. %.

In certain embodiments, the wet mass can be held before extrusion, for example, to allow the spheronization aid to swell with granulating fluid. The hold time can be at least 15 minutes, such as at least 30 minutes, at least 45 minutes, or at least 60 minutes. In certain embodiments, the hold time ranging between about 15 minutes and about 120 minutes, such as between about 30 minutes and 100 minutes, or between 60 minutes and 90 minutes.

As described above relating to cores, the method can include a step of sorting (e.g., by sieving) the cores before optional coating to retain particles in a predetermined size range, for example, sizes ranging between about 0.7 mm and about 2.8 mm, such as between about 0.7 mm and about 2.5 mm, between about 0.8 mm and about 1.7 mm, or any range described herein.

As described above relating to beads, the method can include a step of sorting (e.g., by sieving) the beads after optional coating to retain particles in a size range, for example, sizes ranging between about 0.7 mm and about 2.8 mm, such as between about 0.7 mm and about 2.5 mm, or between about 0.8 mm and about 1.7 mm, or any range described herein.

In an extrusion and spheronization process, the following optional features can be employed, individually or in one or more combinations thereof. Water can be a granulation agent. Microcrystalline cellulose can be in the cores as a spheronization aid. Hypromellose can be included in the cores as a binder. The extrusion screen size can be 1.0 mm. The friction plate of the spheronizer can be cross-hatched. The friction plate of the spheronizer can be cross-hatched with a square pitch of at least about 3 mm, or greater than about 3 mm, or at least about 4 mm, or greater than about 4 mm, or ranging between about 3 mm and about 7 mm, or about 5 mm. The spheronization time can be less than about 5 minutes, or less than about 4 minutes, or less than about 3 minutes, or less than about 2 minutes, or up to 1 minute. The spheronized particles can include non-spherical particles (i.e., irregular shapes), for example, a substantial fraction thereof, such as at least about 20 wt. %, at least about 30 wt. %, at least about 40 wt. %, at least about 50 wt. %, at least about 60 wt. %, or at least about 70 wt. % thereof.

In certain embodiments, the pharmaceutical composition is stored with a desiccant, for example, pharmaceutical grades of silica gel, crystalline sodium, potassium or calcium aluminosilicate, colloidal silica, anhydrous calcium sulfate, and the like.

In certain embodiments, the pharmaceutical composition is stored with an oxygen absorber.

In certain embodiments, the pharmaceutical composition is stored under a dry inert gas such as nitrogen, helium, argon, neon, xenon, krypton, or a mixture thereof.

In certain embodiments, the pharmaceutical composition is stored under reduced pressure in comparison with the external ambient air.

In certain embodiments, the pharmaceutical composition is stored at a reduced temperature, e.g., at refrigerated temperatures (e.g., 2° C. to 8° C.). In certain embodiments, the pharmaceutical composition is stored in such a manner that has fewer impurities, such as Impurity A, than when stored at 25° C.

In certain embodiments, the pharmaceutical composition is stored by a manufacturer, a distributor, a pharmacy, or a hospital at a temperature of between about 2° C. and about 8° C. prior to dispensing the oral pharmaceutical composition to the subject. In certain embodiments, after the oral pharmaceutical composition is dispensed to the subject, the pharmaceutical composition is stored at a temperature of between about 20° C. and about 25° C.

Also provided is a method of stabilizing a pharmaceutical dosage form or composition as described herein, comprising storing the dosage form at a temperature of about 2° C. to about 8° C.

In certain embodiments, a method for preparing a pharmaceutical dosage form comprising xanomeline beads comprises forming a wet mass comprising xanomeline tartrate and an excipient, optionally microcrystalline cellulose, with a moisture content ranging between about 20 wt. % and about 40 wt. %, extruding and spheronizing the wet mass comprising xanomeline tartrate and excipient to make cores, sorting the cores to a target particle size range, optionally between about 0.7 mm and about 2.5 mm, coating the sorted cores with a polymer to form beads comprising a core and a coating, and sorting the bead particles to a target particle size range, optionally between about 0.7 mm and about 2.5 mm.

In certain embodiments, a method for preparing a pharmaceutical dosage form comprising trospium beads comprises forming a wet mass comprising trospium chloride and an excipient, optionally microcrystalline cellulose, with a moisture content ranging between about 20 wt. % and about 40 wt. %, extruding, spheronizing, and drying the wet mass comprising trospium chloride and excipient to make cores, sorting the cores to a target particle size range, optionally between about 0.7 mm and about 2.5 mm, coating the sorted cores with a polymer to form beads comprising a core and a coating, and sorting the bead particles to a target particle size range, optionally between about 0.7 mm and about 2.5 mm.

Purity

Also provided is the compound 3-[(4-hexyloxy)-1,2,5-thiadiazol-3-yl]-5-hydroxyl-1-methylpyridin-1-ium.

Also provided is a pharmaceutical composition, comprising xanomeline and/or a salt thereof and less than 0.5 wt. % 3-[(4-hexyloxy)-1,2,5-thiadiazol-3-yl]-5-hydroxyl-1-methylpyridin-1-ium (Impurity A). In certain embodiments, the pharmaceutical composition comprises less than 0.30 wt. % of Impurity A, such as less than 0.25 wt. %, less than 0.20 wt. %, less than 0.15 wt. %, less than 0.14 wt. % or less than 0.1 wt. %. Also provided is a pharmaceutical composition, comprising xanomeline and/or a salt thereof and less than 0.15 wt. % 3-[(4-hexyloxy)-1,2,5-thiadiazol-3-yl]-5-hydroxyl-1-methylpyridin-1-ium (Impurity A).

Also provided is an oral pharmaceutical composition, comprising a plurality of xanomeline beads comprising xanomeline or a salt thereof and less than 0.5 wt. % 3-[(4-hexyloxy)-1,2,5-thiadiazol-3-yl]-5-hydroxyl-1-methylpyridin-1-ium; and a plurality of trospium beads comprising a salt of trospium. Also provided is an oral pharmaceutical composition, comprising a plurality of xanomeline beads comprising xanomeline or a salt thereof and less than 0.15 wt. % 3-[(4-hexyloxy)-1,2,5-thiadiazol-3-yl]-5-hydroxyl-1-methylpyridin-1-ium; and a plurality of trospium beads comprising a salt of trospium.

In certain embodiments, the pharmaceutical composition comprises less than 0.5 wt. % of Impurity A after the pharmaceutical composition is stored for at least 3 months at 40° C. and 75% relative humidity.

In certain embodiments, the total impurities in the pharmaceutical compositions provided herein are no greater than about 5% by weight, no greater than about 4% by weight, no greater than about 3% by weight, no greater than about 2.5% by weight, no greater than about 2% by weight, no greater than about 1.5% by weight, no greater than about 1% by weight, no greater than about 0.5% by weight, or no greater than about 0.1% by weight.

Method of Treating

Further provided a method of activating muscarinic receptors in a biological sample, the method comprising contacting the biological sample with any oral pharmaceutical composition described herein. Also provided is a method for treating a disorder ameliorated by activating muscarinic receptors in a subject in need thereof, comprising administering to the subject in need thereof any oral pharmaceutical composition described herein.

While activators of M1 and M4 muscarinic receptors have been suggested to be efficacious treatments for schizophrenia, the activation of muscarinic receptors located outside the brain has resulted in side effects that barred xanomeline from the clinic. For instance, in both Phase I and subsequent trials, the muscarinic agonist xanomeline had unacceptable GI and other side effects linked to the binding of muscarinic receptors in the body's periphery. By combining a xanomeline with trospium chloride, the desired therapeutic effect is achieved while diminishing or eliminating the side effects associated with activating muscarinic receptors located outside the brain.

The tolerability of xanomeline, a muscarinic activator, is increased by co-administering trospium chloride, a muscarinic antagonist. The most common adverse events observed with administering xanomeline are nausea, vomiting, diarrhea, excessive sweating, and excessive salivation (so-called cholinergic adverse events). The disclosed compositions reduced the incidence of these adverse events in humans, evincing increased xanomeline tolerability.

In one embodiment, xanomeline is combined with trospium chloride to treat muscarinic disorders, ameliorating symptoms in response to muscarinic activation by xanomeline in living tissues found outside the brain. In an embodiment, such diseases or disorders include schizophrenia and diseases related to schizophrenia, cognitive disorders in neurodegenerative diseases such as Alzheimer's, and pain such as nociceptive pain or neuropathic pain. The combination of xanomeline and trospium chloride is a safer method for treating those diseases shown to be responsive to activation of muscarinic receptors.

In another embodiment, xanomeline and trospium chloride treat mood disorders. In another embodiment, xanomeline and trospium chloride treat movement disorders. In another embodiment, xanomeline and trospium chloride treat cognitive disorders, including enhancing cognitive function not associated with a specific pathology. In another embodiment, xanomeline and trospium chloride treat attention disorders. In another embodiment, xanomeline and trospium chloride treat pain. Outside disease treatment, enhancing attention accelerates learning and decreases fatigue due to both lack of sleep and circadian rhythm disturbances, such as jet lag. In another embodiment, xanomeline and trospium chloride treat addictive disorders.

In one embodiment, xanomeline combined with trospium chloride treats an animal. In a further embodiment, the animal is a mammal. In an embodiment, the mammal is a human being.

In one embodiment, trospium chloride decreases the side effects associated with xanomeline. Such side effects include, but are not limited to, GI side effects, cardiac side effects, excessive sweating, and excessive salivation. Use of trospium with xanomeline allows the xanomeline to be used clinically when the xanomeline would not otherwise be used clinically due to its side effects. In another embodiment, use of trospium chloride with the xanomeline allows for the xanomeline to achieve a higher maximum tolerated dose than xanomeline would otherwise achieve.

Various time and resource-intensive methods demonstrated the efficacy of the combination of xanomeline and trospium chloride. For example, animal models demonstrate the efficacy of new therapeutics for schizophrenia, including both pharmacological models (e.g., ketamine model) and genetic models (e.g., DISC1 mouse). Likewise, animal models, including rodents, dogs, and non-human primates, demonstrate the side effect profile of pharmacological agents. Animal models are an experimental proxy for humans but may suffer from deficiencies in the physiological differences between humans and animals and thus may have limited predictive power for human experiments, particularly for central nervous system disorders. Alternatively, the disclosed combination can be tried in controlled clinical trials of people. Standard measures based on patient self-report can be used by those skilled in the art to assess various side effects such as GI discomfort. As another example, objective physiological measures (e.g., EKGs) may be used by those skilled in the art. A set of standard measures has also been developed to assess schizophrenia symptoms, including the Brief Psychiatric Rating Scale (BPRS), the Positive and Negative Syndrome Scale (PANSS), and Clinical Global Impression (CGI). Typically, clinical trials are double-blinded, where one group of patients receives an inactive placebo, and the other group the active intervention.

Before administering the claimed combinations, patients may have a lead-in period from one to fourteen days, during which lead-in period trospium chloride is given alone. In one embodiment, the trospium chloride is administered for one or more dose periods before administering xanomeline to accumulate trospium chloride in the body or for the trospium chloride to reach or approach steady-state exposure levels. This accumulation, or higher exposure levels of the trospium chloride, increases the blockade of muscarinic receptors outside of the brain and reduces adverse events when xanomeline is administered. In another embodiment, the trospium chloride is administered for one or more days before xanomeline.

In one embodiment, xanomeline and trospium chloride are administered to a patient 6 times during a 24-hour period. In another embodiment, xanomeline and trospium chloride are administered to a patient 5 times during a 24-hour period. In another embodiment, xanomeline and trospium chloride are administered to a patient 4 times during a 24-hour period. In an embodiment, xanomeline and trospium chloride are administered to a patient 3 times during a 24-hour period. In another embodiment, xanomeline and trospium chloride are administered to a patient twice during a 24-hour period. In another embodiment, xanomeline and trospium chloride are administered to a patient once during a 24-hour period.

In one embodiment, an extended-release formulation of trospium chloride is used in combination with xanomeline. In another embodiment, trospium chloride extended-release is administered to a patient from one time to five times during a 24-hour period. In an embodiment, trospium chloride extended-release is administered from one to three times during a 24-hour period. In another embodiment, from five milligrams to 400 milligrams of trospium chloride, extended-release is used during a 24-hour period. In an embodiment, from 20 milligrams to 200 milligrams of trospium chloride, extended-release is used during a 24-hour period.

In one embodiment, 225 mg xanomeline and 40 mg trospium chloride are administered to a patient in a 24-hour period. In another embodiment, 100 mg xanomeline and 20 mg trospium chloride are administered to a patient in a 24-hour period. In another embodiment, 125 mg xanomeline and 20 mg trospium chloride are administered to a patient in a 24-hour period. In another embodiment, 125 mg xanomeline and 30 mg trospium chloride are administered to a patient in a 24-hour period. In another embodiment, 125 mg xanomeline and 40 mg trospium chloride are administered to a patient in a 24-hour period. In another embodiment, 200 mg xanomeline and 40 mg trospium chloride are administered to a patient in a 24-hour period. In another embodiment, 200 mg xanomeline and 80 mg trospium chloride are administered to a patient in a 24-hour period. In another embodiment, 250 mg xanomeline and 60 mg trospium chloride are administered to a patient in a 24-hour period. In another embodiment, 250 mg xanomeline and 80 mg trospium chloride are administered to a patient in a 24-hour period. In another embodiment, 300 mg xanomeline and 40 mg trospium chloride are administered to a patient in a 24-hour period. In another embodiment, 300 mg xanomeline and 80 mg trospium chloride are administered to a patient in a 24-hour period.

Treatment may be initiated with smaller dosages. Thereafter, the dosage may be increased by small increments until a balance between therapeutic effect and side effects is attained. While the subject is being treated, the health of the patient may be monitored by measuring one or more of the relevant indices at predetermined times during the treatment period. Treatment, including composition, amounts, times of administration, and formulation, may be adjusted per such monitoring. The patient may be periodically reevaluated to determine improvement by measuring the same parameters. Adjustments to the disclosed composition administered and possibly to the time of administration may be made based on these reevaluations.

EXAMPLES

The following examples are provided for illustration and are not intended to limit the scope of the disclosure.

Example 1—Immediate Release Beads

Beads were prepared for xanomeline tartrate (Table 1) and trospium chloride (Table 2).

TABLE 1

| Xanomeline tartrate (66%) Bead without Talc | | |
|---|---|---|
| Ingredient | % w/w (dry basis) | g/batch |
| Xanomeline tartrate | 66 | 99 |
| Microcrystalline cellulose | 34 | 51 |
| Purified water* | (30) | (45) |
| Total: | 100 | 150 |

*Removed during drying.

TABLE 2

| Trospium chloride (17.7%) Bead without Talc | | |
|---|---|---|
| Ingredient | % w/w (dry basis) | g/batch |
| Trospium chloride | 17.7 | 17.7 |
| Microcrystalline cellulose | 35 | 35 |
| Lactose monohydrate | 47.3 | 47.3 |
| Purified water* | (45) | (45) |
| Total: | 100 | 100 |

*Removed during drying.

The powders were screened using Quadro Comil Model 197 equipped with 457-μm round hole screen, 0.2-inch spacer at 1625 rpm and mixed for 2 min in a Hobart low shear mixer/granulator (model N-50) at a fixed speed of 60 rpm. The dry blending step is optional, as blend uniformity is driven by subsequent wet granulation. Beads were screened by hand through a 40 mesh (425 μm) sieve.

Wetting was carried out in the Hobart. The water was added using a Cole-Parmer peristaltic pump. Water addition rate (amount of water/dose time) is a process variable.

The wet mass was extruded through a perforated screen (dome configuration) single screw extruder using an LCI Multi Granulator MG-55 at 30 rpm (shaft speed). The wet mass was extruded directly after wetting. Hold time, shaft speed, and extrusion rate (load) were process variables.

The extrudates were placed into an LCI Marumerizer (spheronizer) QJ-230T equipped with a 2.0 mm friction plate. The extrudates were spheronized at different plate speeds for a total of not more than 4 minutes. Spheronization speed and time are process variables.

The beads were dried using an Aeromatic™ Strea-1 fluid bed at an inlet temperature of 60° C. until a water content of not more than 3% was obtained. Because beads melted after a few minutes at 60° C., the beads were dried at 30° C.

Water content was evaluated gravimetrically by loss-on-drying (LOD) using a Mettler Toledo Halogen Moisture Analyser, type HR83. The beads were heated at 105° C. until the rate of weight loss dropped to less or equal to 0.0% within 60 seconds.

TABLE 3

Extrusion/Spheronization Process Parameters

| Parameter | Xanomeline tartrate (66% w/w) | Trospium chloride (17.7% w/w) |
|---|---|---|
| *Wet massing* | | |
| Powder (g) | 150 | 100 |
| Water (g) | 45 | 45 |
| % (w/w) dry basis | 30 | 45 |
| Dose time (min) | 3 | 3 |
| Total massing time (min) | 3.5 | 3.5 |
| Liquid rate (g/min) | 15 | 17 |
| *Extrusion* | | |
| Hold time (min) | 0 | 0 |
| Die hole size (mm) | 0.8 | 0.8 |
| Shaft speed (rpm) | 30 | 30 |
| Load (Ap) | 2.3 | 2.2-2.4 |
| *Spheronization* | | |
| Plate speed (rpm) | 900/1500 | 900 |
| Spheronization time (min) | 1/1 | 2 |
| *Drying* | | |
| Inlet Temp.(° C.) | 60 | 60 |
| Outlet Temp. (° C.) | NMT 53 | NMT 53 |
| Drying time (min) | 75 | 30 |
| LOD (%) | 3.5 | 2.5 |

Example 2—Scaling Up Immediate Release Bead Formulations

The beads from Example 1 were scaled-up with and without talc (Tables 4-7). Extrusion/Spheronization process parameters are shown in Table 8.

TABLE 4

Xanomeline Tartrate (66%) Beads Without Talc

| Ingredient | % w/w (dry basis) | g/batch |
|---|---|---|
| Xanomeline tartrate | 66 | 660 |
| Microcrystalline cellulose | 34 | 340 |
| Purified water* | (24) | (240) |
| Total: | 100 | 1000 |

*Removed during drying.

TABLE 5

Xanomeline tartrate (66%) Bead with Talc

| Ingredient | Purpose | % w/w (dry basis) | g/batch |
|---|---|---|---|
| Xanomeline tartrate | Active | 66.0 | 3,465.0 |
| Microcrystalline cellulose (USP, Ph. Eur.) | Binder, disintegrant | 33.5 | 1758.75 |
| Purified water* (USP) | Granulating fluid | (30.0) | (1575.0) |
| Talc (USP, Ph. Eur.) | Glidant | 0.5 | 26.25 |
| Total | | 100.0 | 5,250.0 |

Abbreviations:
Ph. Eur = European Pharmacopeia,
USP = United States Pharmacopeia
*Evaporated during the process thus not included in total weight

TABLE 6

Trospium Chloride (17.7%) Beads Without Talc

| Ingredient | % w/w (dry basis) | g/batch |
|---|---|---|
| Trospium chloride | 17.7 | 88.7 |
| Microcrystalline cellulose | 35 | 175.0 |
| Lactose monohydrate | 47.3 | 236.3 |
| Purified water* | (59) | (295) |
| Total: | 100 | 500 |

*Removed during drying.

TABLE 7

Trospium chloride (17.7%) Bead with Talc

| Ingredient | Purpose | % w/w (dry basis) | g/batch |
|---|---|---|---|
| Trospium chloride (USP) | Active | 17.7 | 593.6 |
| Microcrystalline cellulose (USP, Ph. Eur.) | Binder, disintegrant | 46.8 | 1567.15 |
| Lactose monohydrate (NF) | Filler | 35.0 | 1,172.5 |
| Purified water* (USP) | Granulating fluid | (47.0) | (1574.5) |
| Talc (USP, Ph. Eur.) | Glidant | 0.5 | 16.75 |
| Total | | 100 | 3,350.0 |

Abbreviations:
NF = National Formulary,
Ph. Eur = European Pharmacopeia,
USP = United States Pharmacopeia.
*Evaporated during process

TABLE 8

Extrusion/Spheronization Process Parameters

| Parameter | Xanomeline tartrate (66% w/w) | Trospium chloride (17.7% w/w) |
|---|---|---|
| *Wet massing* | | |
| Powder (g) | 1000 | 500 |
| Water (g) | 240 | 295 |
| % (w/w) dry basis | 24 | 59 |
| Dose time (min) | 3 | 4 |
| Total massing time (min) | 3.5 | 4.5 |
| Liquid rate (g/min) | 80 | 82 |
| *Extrusion* | | |
| Hold time (min) | 0 | 0 |
| Die hole size (mm) | 0.8 | 0.8 |

TABLE 8-continued

Extrusion/Spheronization Process Parameters

| Parameter | Xanomeline tartrate (66% w/w) | Trospium chloride (17.7% w/w) |
|---|---|---|
| Shaft speed (rpm) | 30 | 30 |
| Load (Ap) | 2.2-2.3 | 2.4-2.5 |
| Spheronization | | |
| Plate speed (rpm) | 900 | 900 |
| Spheronization time (min) | 0.5 | 1 |
| Drying | | |
| Inlet Temp. (° C.) | 60 | 60 |
| Outlet Temp. (° C.) | NMT 50 | NMT 49 |
| Drying time (min) | 50 | 40 |
| LOD (%) | 2.3 | 2.4 |

Example 3—Capsule Stability and Dissolution Testing

Capsules were produced by weighing beads and filling them into HPMC capsules manually. Beads were encapsulated by hand using an Accofil™ capsule filling machine where beads premixed with talc (0.5%) were filled individually/one-after-the-other in the capsule, as shown in Table 9.

TABLE 9

Composition of Xanomeline/Trospium Chloride Capsules. Ingredients are listed in milligrams per capsule.

| Ingredient | Function | 25 mg/ 10 mg | 50 mg/ 10 mg | 50 mg/ 20 mg | 75 mg/ 10 mg | 75 mg/ 20 mg |
|---|---|---|---|---|---|---|
| Xanomeline drug beads | Active ingredient | 58.1 | 116.1 | 116.1 | 174.2 | 174.2 |
| Xanomeline tartrate | Drug substance | 38.3 | 76.6 | 76.6 | 115.0 | 115.0 |
| [total weight (freebase)] | | (25.0) | (50.0) | (50.0) | (75.0) | (75.0) |
| Microcrystalline cellulose (USP, Ph.Eur.) | Binder, disintegrant | 19.5 | 38.9 | 38.9 | 58.4 | 58.4 |
| Talc (USP, Ph. Eur.) | Glidant | 0.3 | 0.6 | 0.6 | 0.9 | 0.9 |
| Trospium drug beads | Active ingredient | 56.5 | 56.5 | 113.0 | 56.5 | 113.0 |
| Trospium chloride (USP) | Drug substance | 10 | 10 | 20 | 10 | 20 |
| Microcrystalline cellulose (USP, Ph. Eur.) | Binder, disintegrant | 26.4 | 26.4 | 52.9 | 26.4 | 52.9 |
| Lactose monohydrate, NF | Filler | 19.8 | 19.8 | 39.6 | 19.8 | 39.6 |
| Talc (USP, Ph. Eur.) | Glidant | 0.3 | 0.3 | 0.6 | 0.3 | 0.6 |
| HPMC capsule shell | Capsule | 95.6 | 95.6 | 95.6 | 95.6 | 95.6 |
| Hydroxypropyl methyl-cellulose (USP, Ph. Eur.) | Structure | 93.7 | 93.7 | 93.7 | 93.7 | 93.7 |
| Titanium dioxide (USP, Ph. Eur.) | Colorant | 1.9 | 1.9 | 1.9 | 1.9 | 1.9 |
| Total | | 210.2 | 268.2 | 324.7 | 326.3 | 382.8 |

After drying, the beads were screened by shaking for 5 min through 16 mesh (1.18 mm) and 40 mesh (0.425 mm) screens. The beads in size between sieves 1.18 mm and 0.425 mm were retained for further analysis.

The morphology and surface characteristics of beads were examined by scanning electron microscopy (SEM) using a JSM-6010LV InTouchScope™ (JEOL Ltd, Tokyo, JP) microscope with a back-scattered electron detector (BES). Samples were placed on metallic stubs using double-sided carbon conductive tape. The images were obtained with accelerating voltages of 20 kV under low vacuum (60 Pa) and magnification 30×.

Bulk and tapped density were determined in duplicate using the USP<616> method using a tapped density tester (JV 1000, Copley Scientific). The bulk density was measured from the volume of a known mass of powder sample in a graduated cylinder. The tapped density was measured by mechanically tapping the measuring cylinder until the volume changed no further.

The powder flow properties were evaluated using Carr's Compressibility Index and Hausner ratio. Both were derived using the measured values for bulk and tapped density. Carr's Compressibility Index (CI) was calculated using bulk and tapped density data when fitted into the equation: Compressibility Index=(Tapped density−Bulk density)/Tapped density×100%. Hausner Ratio (H) was calculated as the ratio of tapped to bulk density. Capsules were analyzed for appearance, assay, related substances, water content, and dissolution. FIG. 1 shows the stability schedule and protocol for xanomeline/trospium capsules.

Figure 3:
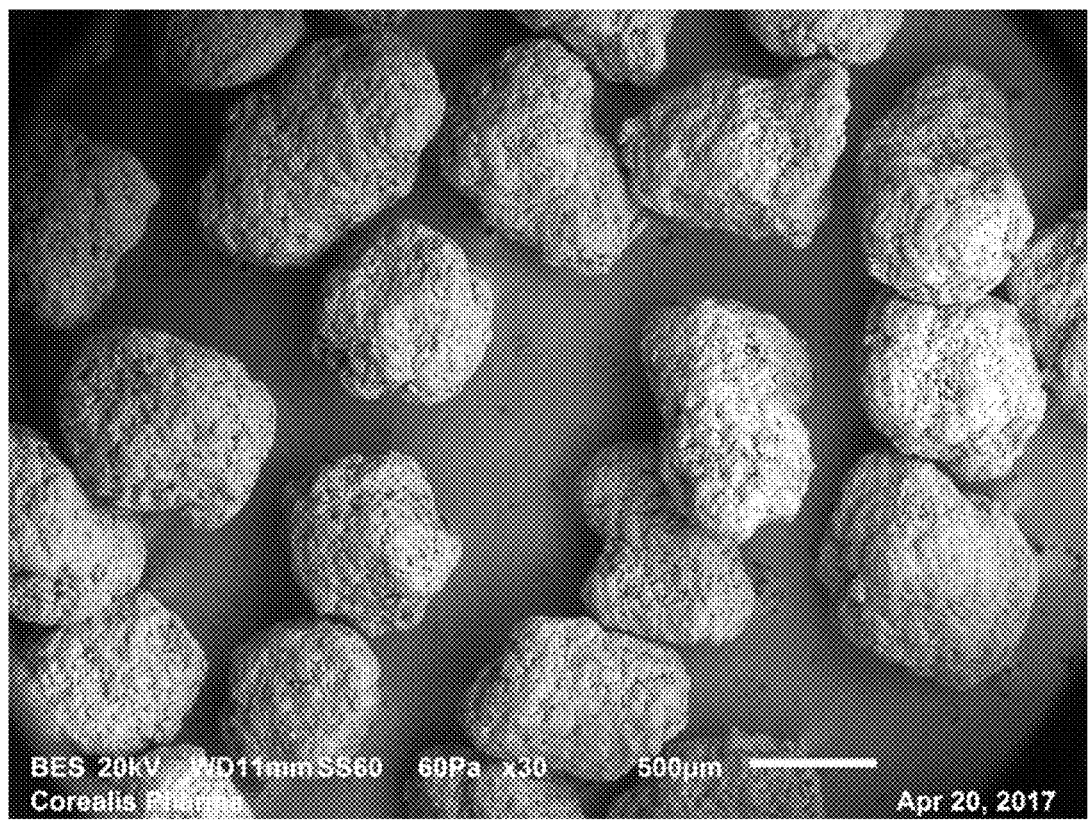
FIG. 3 is an SEM image of trospium chloride 17.7% beads at 30× magnification, showing that the beads are sized between 0.6 mm and 0.85 mm used for xanomeline/trospium capsules.
Figure 4:
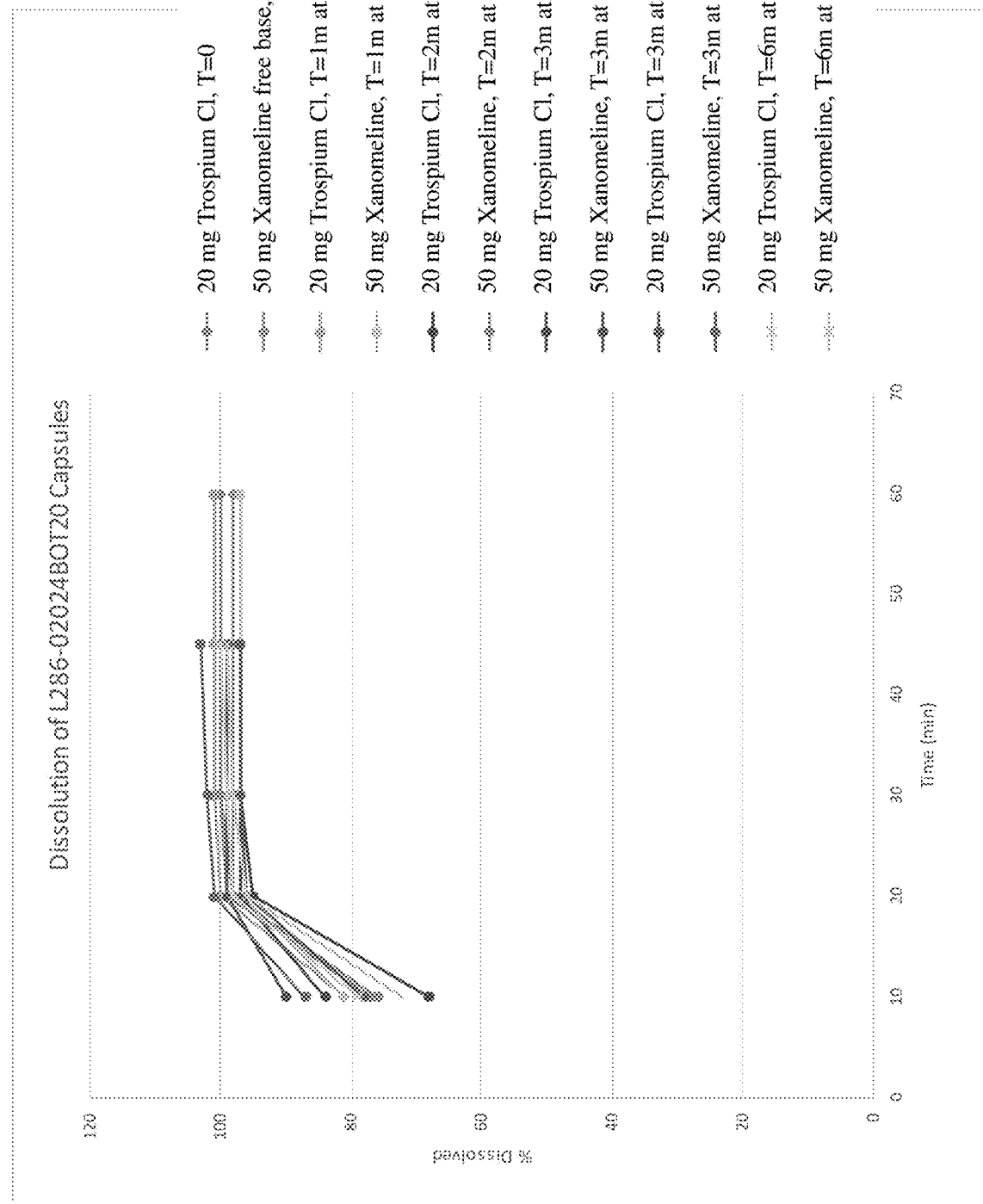
FIG. 4 is the dissolution profile of xanomeline/trospium Cl, 50/20 mg capsules containing xanomeline beads and trospium Cl beads and measured at time 0, 1 month, 2 months, 3 months, and 6 months following storage at 40° C./75% RH, as well as 3 months after storage at 25° C./60% RH.
Figure 5:
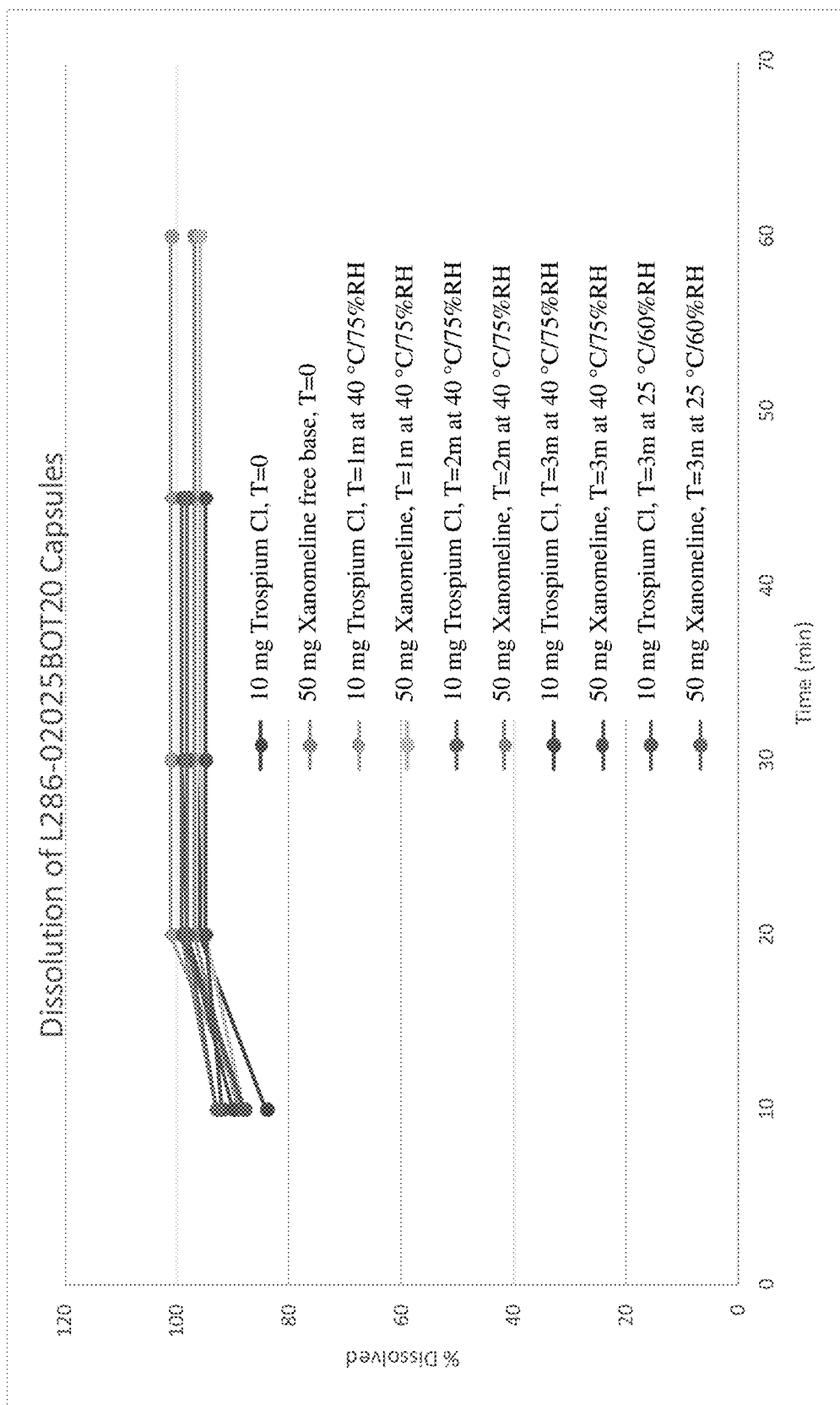
FIG. 5 is the dissolution profile of xanomeline/trospium Cl, 50/10 mg capsules containing xanomeline beads and trospium Cl beads and measured at time 0, 1 month, 2 months, and 3 months following storage at 40° C./75% RH as well as 3 months after storage at 25° C./60% RH.

The beads were further sized between 0.6 mm and 0.85 mm. Some beads exhibited similar morphological properties. Modifications in some other beads decreased the density of beads and led to rough surfaces and loss of sphericity. Scanning electron microscope (SEM) images of xanomeline tartrate 66% beads (FIG. 2) trospium chloride 17.7% beads (FIG. 3) at 30× magnification showed that the beads are sized between 0.6 mm and 0.85 mm. These beads were used in xanomeline/trospium capsules. Particle size distribution (PSD) of beads was determined by mechanical sieving. As shown in Table 10, most beads for both APIs were sized between 0.425 and 1.18 mm.

TABLE 10

Particle Size Distribution by Mechanical Sieving of Beads

| | % Retained | |
|---|---|---|
| Sieve No. (opening diameter) | 66% Xanomeline tartrate | 17.7% Trospium chloride |
| 16 mesh (1.18 mm) | 8.1 | 0.4 |
| 40 mesh (0.425 mm) | 90.6 | 97.3 |
| Receiver | 1.3 | 2.3 |
| Total: | 100 | 100 |

Table 11 shows the densities and flow properties of beads collected between 0.425 mm and 1.18 mm sieves. Xanomeline tartrate and trospium chloride IR beads showed different densities and flow properties, which can be critical when mixing bead systems.

TABLE 11

Density and Flow Properties of 0.425-1.18 mm Beads

| Sample ID | Bulk density (g/cm$^3$) | Tapped density (g/cm$^3$) | Carr Index (%) | Hausner Ratio |
|---|---|---|---|---|
| Xanomeline tartrate (66%) beads - Example 1 | 0.59/0.58 | 0.63/0.62 | 7/7 | 1.08/1.08 |
| Xanomeline tartrate (66%) beads - Scale up | 0.54/0.54 | 0.58/0.57 | 6/6 | 1.07/1.07 |
| Trospium chloride (17.7%) beads - Example 1 | 0.81/0.80 | 0.83/0.83 | 2/3 | 1.02/1.04 |
| Trospium chloride (17.7%) beads - Scale up | 0.78/0.79 | 0.81/0.82 | 3/3 | 1.03/1.03 |

The analysis in Table 12 shows favorable results for assay and related substances and moisture content for 50 mg xanomeline and 20 mg trospium chloride capsules. Data in Table 13 show that these attributes were retained during storage stability studies. Similar data are provided for the 50 mg xanomeline and 10 mg trospium chloride capsules in Table 14. Dissolution data for these two dosage forms are provided in Table 15 and Table 16. Other tables showing stability for the xanomeline/trospium chloride formulations are shown in FIGS. 6-41.

TABLE 12

Analytical Results

| Formulation | Trospium Chloride/ Xanomeline Tartrate Beads in Capsules | Trospium Chloride/ Xanomeline Tartrate Beads in Capsules |
|---|---|---|
| Dose strength | 20 mg salt Trospium Chloride 50 mg Xanomeline free base | 10 mg salt Trospium Chloride 50 mg Xanomeline free base |
| Description | White opaque capsules | White opaque capsules |
| Assay (% LC) | Trospium chloride 98.9% (n = 2: 99.2, 98.5) Xanomeline free base 99.4% (n = 2: 100.1, 98.8) | Trospium chloride 97.1% (n = 2: 97.1, 97.1) Xanomeline free base 100.6% (n = 2: 100.3, 101.0) |
| Related Substances (% LC) | No impurities ≥0.1% LC | No impurities ≥0.1% LC |
| Moisture (KF) (% w/w) | 2.4% | 2.2% |

TABLE 13

Stability of KarXT 50/20

| Description | T = 0 | White opaque capsules |
|---|---|---|
| | T = 1 m, 40° C./75% RH | No change from initials |
| | T = 2 m, 40° C./75% RH | No change from initials |
| | T = 3 m, 25° C./60% RH | No change from initials |
| | T = 3 m, 40° C./75% RH | No change from initials |
| | T = 6 m, 40° C./75% RH | No change from initials |
| Assay (% LC) | T = 0 | Trospium chloride: 98.9 (99.2, 98.5) Xanomeline free base: 99.4 (100.1, 98.8) |
| | T = 1 m 40° C./75% RH | Trospium chloride 100.4 (97.8, 103.1) Xanomeline free base: 101.7 (101.6, 101.8) |
| | T = 2 m 40° C./75% RH | Trospium chloride: 98.2 (98.7, 97.7) Xanomeline free base: 99.3 (100.3, 98.3) |
| | T = 3 m 25° C./60% RH | Trospium chloride: 99.1 (99.7, 98.4) Xanomeline free base: 102.0 (103.7, 100.3) |
| | T = 3 m 40° C./75% RH | Trospium chloride: 98.4 (98.5, 98.3) Xanomeline free base: 99.9 (99.8, 100.0) |
| | T = 6 m 40° C./75% RH | Trospium chloride: 96.0 (95.6, 96.4) Xanomeline free base: 97.8 (97.6, 98.1) |
| Related Substances (% LC) | T = 0 | No impurities ≥0.1% LC |
| | T = 1 m, 40° C./75% RH | No impurities ≥0.1% LC |
| | T = 2 m, 40° C./75% RH | 0.14% |
| | T = 3 m, 25° C./60% RH | No impurities ≥0.1% LC |
| | T = 3 m, 40° C./75% RH | 0.14% |
| | T = 6 m, 40° C./75% RH | 0.2% |
| Moisture (KF) (% w/w) USP <921> Method Ia | T = 0 | 2.4% |
| | T = 1 m, 40° C./75% RH | 3.0% |
| | T = 2 m, 40° C./75% RH | 3.3% |
| | T = 3 m, 25° C./60% RH | 2.7% |
| | T = 3 m, 40° C./75% RH | 2.6% |
| | T = 6 m, 40° C./75% RH | 3.4% |

TABLE 14

Dissolution of KarXT 50/20

| Active Time | | (min) | Trospium chloride % LC Range | Xanomeline free base % LC Range |
|---|---|---|---|---|
| Dissolution T = 0 900 mL 0.1N HCl Paddles @ 50 rpm, ramp @ 200 rpm after 45 min (n = 3) | | 10 | 77  90, 88, 52 | 76  93, 87, 47 |
| | | 20 | 99  101, 99, 97 | 98  98, 97, 98 |
| | | 30 | 100  101, 99, 99 | 98  99, 97, 99 |
| | | 45 | 100  101, 100, 99 | 98  98, 97, 99 |
| | | 60 (ramp) | 100  101, 99, 99 | 98  98, 97, 99 |
| | T = 1 m 40° C./ 75% RH | 10 | 81  78, 78, 85 | 81  77, 86, 80 |
| | | 20 | 100  102, 95, 102 | 97  99, 98, 93 |
| | | 30 | 101  102, 97, 103 | 97  99, 99, 94 |
| | | 45 | 101  102, 97, 103 | 97  99, 99, 93 |
| | | 60 (ramp) | 101  102, 97, 103 | 97  99, 99, 93 |
| | T = 2 m 40° C./ 75% RH | 10 | 68  83, 74, 48 | 76  92, 82, 55 |
| | | 20 | 95  98, 93, 94 | 98  101, 98, 96 |
| | | 30 | 97  99, 95, 96 | 100  103, 99, 98 |
| | | 45 | 97  99, 95, 96 | 100  103, 99, 98 |
| | T = 3 m 25° C./ 60% RH | 10 | 78  84, 80, 69 | 87  94, 93, 75 |
| | | 20 | 96  99, 96, 91 | 101  104, 103, 97 |
| | | 30 | 97  99, 97, 95 | 102  104, 104, 99 |
| | | 45 | 97  99, 97, 96 | 103  104, 104, 101 |
| | T = 3 m 40° C./ 75% RH | 10 | 84  90, 84, 78 | 90  95, 89, 87 |
| | | 20 | 97  98, 98, 96 | 99  99, 98, 99 |
| | | 30 | 97  97, 98, 96 | 99  99, 99, 100 |
| | | 45 | 97  97, 98, 96 | 99  99, 99, 100 |
| | T = 6 m 40° C./ 75% RH | 10 | 72  85, 53, 78 | 79  92, 58, 86 |
| | | 20 | 96  98, 92, 98 | 98  99, 94, 100 |
| | | 30 | 98  99, 95, 99 | 99  99, 97, 101 |
| | | 45 | 99  100, 96, 99 | 100  100, 98, 101 |

TABLE 15

Assay and Related Substances of KarXT 50/10

| Description | T = 0 | White opaque capsules |
|---|---|---|
| | T = 1 m, 40° C./75% RH | No change from initials |
| | T = 2 m, 40° C./75% RH | No change from initials |
| | T = 3 m, 25° C./60% RH | No change from initials |
| | T = 3 m, 40° C./75% RH | No change from initials |
| Assay (% LC) | T = 0 | Trospium chloride: 97.1 (97.1, 97.1) |
| | | Xanomeline free base: 100.6 (100.3, 101.0) |
| | T = 1 m 40° C./75% RH | Trospium chloride: 98.5 (98.2, 98.9) |
| | | Xanomeline free base: 102.7 (104.4, 101.1) |
| | T = 2 m 40° C./75% RH | Trospium chloride: 96.7 (95.7, 97.6) |
| | | Xanomeline free base: 98.8 (99.3, 98.3) |
| | T = 3 m 25° C./60% RH | Trospium chloride: 98.5 (96.5, 100.5) |
| | | Xanomeline free base: 99.2 (98.2, 100.1) |
| | T = 3 m 40° C./75% RH | Trospium chloride: 98.1 (97.6, 98.6) |
| | | Xanomeline free base: 99.4 (99.0, 99.8) |
| Related Substances (% LC) | T = 0 | No impurities ≥0.1% LC |
| | T = 1 m, 40° C./75% RH | No impurities ≥0.1% LC |
| | T = 2 m, 40° C./75% RH | 0.14% |
| | T = 3 m, 25° C./60% RH | No impurities ≥0.1% LC |
| | T = 3 m, 40° C./75% RH | 0.14% |
| Moisture (KF) (% w/w) USP <921> Method Ia | T = 0 | 2.2% (n = 2: 2.4, 2.1) |
| | T = 1 m, 40° C./75% RH | 2.1% (n = 2: 2.4, 1.9) |
| | T = 2 m, 40° C./75% RH | 2.2% (n = 3: 1.8, 2.4, 2.4) |
| | T = 3 m, 25° C./60% RH | 2.1% (n = 3: 1.9, 2.4, 2.1) |
| | T = 3 m, 40° C./75% RH | 2.5% (n = 3: 2.3, 2.6, 2.4) |

TABLE 16

Dissolution of KarXT 50/10

| | | | 10 mg Trospium Chloride | | 50 mg Xanomeline free base | |
|---|---|---|---|---|---|---|
| | | Active Time | Trospium Chloride | | Xanomeline free base | |
| Dose strength | | (min) | % LC | Range | % LC | Range |
| Dissolution 900 ml 0.1N HCl Paddles @ 50 rpm ramp @ 200 rpm after 45 min (n = 3) | T = 0 | 10 | 84 | 85, 86, 82 | 89 | 88, 90, 88 |
| | | 20 | 96 | 97, 96, 94 | 97 | 96, 96, 98 |
| | | 30 | 96 | 97, 97, 94 | 97 | 96, 97, 98 |
| | | 45 | 96 | 97, 96, 94 | 97 | 96, 96, 98 |
| | | 60 (ramp) | 96 | 97, 97, 94 | 97 | 96, 96, 98 |
| | T = 1 m 40° C./ 75% RH | 10 | 88 | 83, 91, 89 | 88 | 87, 92, 85 |
| | | 20 | 101 | 100, 101, 101 | 95 | 96, 97, 94 |
| | | 30 | 101 | 101, 101, 101 | 96 | 97, 97, 94 |
| | | 45 | 101 | 102, 101, 101 | 96 | 97, 97, 94 |
| | | 60 (ramp) | 101 | 102, 101, 102 | 96 | 97, 97, 94 |
| | T = 2 m 40° C./ 75% RH | 10 | 88 | 89, 91, 83 | 93 | 94, 91, 93 |
| | | 20 | 98 | 97, 102, 96 | 99 | 99, 98, 101 |
| | | 30 | 99 | 98, 103, 97 | 99 | 99, 98, 101 |
| | | 45 | 99 | 97, 103, 96 | 99 | 99, 98, 101 |
| | T = 3 m 25° C./ 60% RH | 10 | 88 | 79, 91, 94 | 93 | 86, 94, 99 |
| | | 20 | 99 | 95, 99, 102 | 98 | 95, 97, 102 |
| | | 30 | 99 | 95, 99, 102 | 98 | 95, 96, 102 |
| | | 45 | 99 | 95, 99, 102 | 98 | 95, 96, 102 |
| | T = 3 m 40° C./ 75% RH | 10 | 90 | 89, 90, 91 | 92 | 90, 95, 90 |
| | | 20 | 98 | 99, 95, 99 | 95 | 95, 97, 94 |
| | | 30 | 98 | 99, 95, 99 | 95 | 95, 97, 94 |
| | | 45 | 98 | 99, 95, 99 | 95 | 95, 97, 94 |

Subsequent testing showed that KarXT 50/10, 50/20, and 75/20 in hard-shell capsules were stable for at least 12 months 25° C./60% RH. Based on available data, a shelf-life of 15 months at 25° C./60% RH is proposed.

The dissolution results show that the two compounds release quickly, which may increase their bioavailability, and that they also release at comparable rates despite substantial differences in compositions between the two bead formulations. Both xanomeline and trospium chloride have low bioavailabilities, and rapid release can increase bioavailability by overwhelming saturable processes that limit absorption into the general circulation.

An unknown xanomeline impurity with a relative retention time of about 1.09 was observed during stability studies of the combination drug products. The impurity was first observed during testing at the three-month time point for the 50 mg xanomeline/10 mg trospium chloride drug product and at the initial time point for the other three combination products, both of which occurred at the same time. The impurity peak increased both with time and with increasing storage temperature. The impurity had not been observed before the present studies.

Preliminary studies suggest that the RRT 1.09 impurity is 3-[(4-hexyloxy)-1,2,5-thiadiazol-3-yl]-5-hydroxyl-1-methylpyridin-1-ium ($C_{14}H_{20}N_3O_2S^+$, MW=294.1271 Da):

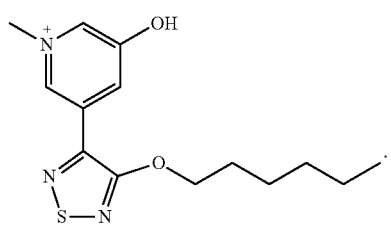

The RRT 1.09 impurity is a hydroxylated version of Compound V ($C_{14}H_{20}N_3OS^+$, MW=278.1322 Da), which is the penultimate intermediate in the synthesis of xanomeline with negative mutagenic potential:

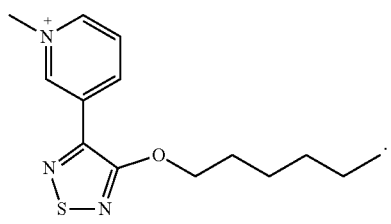

To reduce the presence of the impurity, the storage temperature for the drug product was lowered. Bottles were flushed with argon to minimize headspace oxygen during packaging. In certain embodiments, the xanomeline bead formulation was formulated with an antioxidant, such as 0.5 wt. % ascorbic acid or 0.05 wt. % BHT.

Example 4—KAR-001 Phase I Study of Combination of Xanomeline and Trospium Chloride A Phase I, double-blind, randomized multiple-dose pilot study was conducted with xanomeline administered alone compared to xanomeline administered with trospium chloride in normal healthy volunteers. The primary objectives of this study were (1) to assess the safety and tolerability of administering, for 7 days, 225 mg daily of xanomeline with 40 mg daily of trospium chloride, versus administering 225 mg daily of xanomeline alone for 7 days; and (2) to determine whether adding trospium 40 mg daily (20 mg BID) to xanomeline 225 mg daily (75 mg TID) over 7 days significantly reduces peripheral cholinergic side effects (nausea, diarrhea, vomiting, sweating, excess salivation) versus xanomeline 225 mg daily, alone. Table 17 lists the parameters from this study.

TABLE 17

Parameters of the KAR-001 study

| | |
|---|---|
| Sample Size: | N = 70 subjects |
| Study Population: | Normal healthy volunteers; ages 18-60 |
| Study Duration: | Treatment: Nine days; a two-day run-in period of either placebo or trospium 40 mg/day, followed by 7 days of active treatment |
| | Follow-up: 14 days following discharge from the clinic |
| Test product, dose, and mode of administration: | Xanomeline, 75 mg capsules, TID, for a 225-mg total daily dose |
| | Trospium chloride, 20 mg tablet, over-encapsulated, for a 40-mg total daily dose, BID. Matching placebo. |
| Study Design | The study was an inpatient study conducted in normal healthy volunteers. Between study days −21 to −7, normal healthy volunteers visited the clinic to receive and sign Informed Consent and undergo screening procedures. |
| | Patients entered the clinic on Study Day 0 for baseline safety assessment and enrollment in the study. |
| | On the morning of Study Day 1 subjects began administration of study drug. Subjects randomized to the xanomeline-only arm received placebo for the first two days, and began TID xanomeline treatment on Day 3. Subjects randomized to the xanomeline + trospium arm received BID trospium chloride for the first two days, and then TID xanomeline plus BID trospium starting on Day 3. Matching placebo was administered to maintain the blind. Patients remained in clinic under observation for the full duration of treatment (9 days). |
| Main criteria for inclusion: | Age 18-60 |
| | Female subjects had to be postmenopausal (at least 2 years prior to dosing) or agree to use an acceptable form of birth control from screening until 14 days after completion of the study. If on birth control pills, had to have been on a stable dose for ≥12 months. |
| | Good general health |
| | Ability to give informed consent and understand verbal instructions. |
| | Willingness to spend 10 days in an in-patient facility. |
| Main criteria for exclusion: | History or presence of clinically significant cardiovascular, pulmonary, hepatic, renal, hematologic, gastrointestinal, endocrine, immunologic, dermatologic, neurologic, oncologic, or psychiatric disease or any other condition that, in the opinion of the investigator, would jeopardize the safety of the subject or the validity of the study results. (Subjects with any history of resolved cancer that was >5 years passed could be included.) |
| | Body Mass Index <18 or >40 kg/m$^2$ |
| | History of or high risk of urinary retention, gastric retention, or narrow-angle glaucoma. |
| | History of alcohol or drug abuse within the last 24 months, or current abuse as determined by urine toxicology screen. |
| | Clinically significant abnormal finding on the physical exam, medical history, ECG, or clinical laboratory results at screening. |
| | Had participated in another clinical trial within 90 days before the first dose of study medication. |
| | Needed to take any prescription medication besides the investigational product or those specifically noted above. |
| | Use of any vitamins, herbs, supplements, or over-the-counter medications are excluded within one week of enrollment, and during the trial. Specifically, subjects were not permitted to take Benadryl ® for one week prior to and during the study. Use of any tobacco products within the past 30 days. |
| | Previous positive test for HIV 1 and/or 2, or Hepatitis A, B, or C, or a positive test obtained at screening. |
| Selected Endpoints: | Treatment emergent signs and symptoms (adverse event incidence rates). |
| | Cholinergic treatment emergent signs and symptoms (salivation, sweating, nausea, vomiting, diarrhea) (cholinergic adverse event incidence rates). These adverse events were observed at high rates in past xanomeline studies and were drivers of subject discontinuation. |

Seventy total study subjects were randomized, and of these, 68 study subjects received at least one assessment on day 3, which was the first day of xanomeline administration. Table 18 lists the demographics of the study subjects.

TABLE 18

Demographics of the KAR-001 study subjects

| Characteristic | Xanomeline alone (N = 33) | Xanomeline + Trospium (N = 35) |
|---|---|---|
| Age (years; Mean [SD]) | 34.8 [8.8] | 40.9 [12.3] |
| Gender (M/F; [%]) | 21/12 | 27/8 |
|  | 64%/36% | 77%/23% |
| Race (White/ | 9/24 | 13/21 |
| Non-White; [%]) | 27%/70% | 37%/60% |
| Weight (kg; Mean [SD]) | 88 [17] | 88 [16] |
| BMI (kg/m2; Mean [SD]) | 29.1 [5.0] | 28.8 [5.0] |

The most common adverse events with xanomeline are the so-called cholinergic adverse events of nausea, vomiting, diarrhea, excessive sweating, and excessive salivation. In this study, the co-administration of trospium chloride with xanomeline led to a statistically significant (p=0.016) 43% reduction in the incidence rate of cholinergic adverse events compared to xanomeline co-administered with placebo. In the xanomeline+placebo arm of the study, 63% of subjects reported at least one cholinergic adverse event, compared to only 34% of subjects reporting such an event in the xanomeline+trospium chloride arm of the study.

Further, in the study, each kind of individual cholinergic adverse event also had a decreased incidence rate in subjects administered xanomeline+trospium chloride, compared to the incidence rate in subjects administered xanomeline+placebo. The decrease in the incidence rate of sweating was statistically significant on its own, at 20.0% in the xanomeline+trospium chloride arm, down from 48.5% in the xanomeline+placebo arm, which was a 59% reduction (p=0.013).

The overall cholinergic adverse event rate in the xanomeline+trospium chloride arm of the study was very similar to the 32% incidence rate reported during the two-day run-in period for subjects on placebo+placebo. Although these two data points did not occur during different periods of the study, the fact that the cholinergic adverse event rate was comparable to that of placebo suggests that the 43% reduction in adverse events due to trospium chloride may have been close to the maximum reduction possible in this study.

Table 19 shows the incidence and number of cholinergic adverse events in the evaluable population of the study were as follows, with all p-values based on a chi-squared test, except those marked with an *, which were based on a Fisher's exact test.

TABLE 19

Cholinergic adverse events

| Category | Xanomeline + placebo (n = 34) (n [%] [# of events]) | Xanomeline + Trospium (n = 35) (n [%] [# of events]) | P-value for difference | % Reduction |
|---|---|---|---|---|
| Any | 21 (63.6%) 64 | 12 (34.3%) 33 TEAEs | 0.0155 | 46% |
| Nausea | 8 (24.2%) 11 | 6 (17.1%) 8 | 0.4693 | 29% |
| Vomiting | 5 (15.2%) 5 | 2 (5.7%) 2 | 0.2522* | 62% |
| Diarrhea | 7 (21.2%) 8 | 2 (5.7%) 4 | 0.0794* | 73% |
| Sweating | 16 (48.5%) 24 | 7 (20.0%) 8 | 0.0131 | 59% |
| Salivation | 12 (36.4%) 16 | 9 (25.7%) 11 | 0.342 | 39% |

In addition to evaluating whether adding trospium chloride increased the tolerability of xanomeline, the study also provided data about the overall safety and tolerability of xanomeline+trospium chloride. Table 20 shows that overall the combination was well tolerated with no severe adverse events and no serious adverse events, and with most adverse events being mild.

TABLE 20

Tolerability

| Category (n (%) # events) | Xanomeline + placebo (N = 33) | Xanomeline + Trospium (N = 35) |
|---|---|---|
| Subjects with any TEAE | 27 (81.8) 108 | 23 (65.7) 73 |
| Max Severity of TEAE | | |
| Mild | 22 (66.7) N/A | 20 (57.1) N/A |
| Moderate | 5 (15.2) N/A | 3 (8.6) N/A |
| Severe | 0 (0.0) | 0 (0.0) |
| Any clinically significant TEAE | 5 (15.2) 5 | 3 (8.6) 6 |
| Any study drug-related TEAE | 23 (69.7) 92 | 18 (51.4) 57 |
| Max severity of study drug-related TEAE | | |
| Mild | 19 (57/6) N/A | 15 (42.9) N/A |
| Moderate | 4 (12.1) N/A | 3 (8.6) N/A |
| Severe | 0 (0.0) N/A | 0 (0.0) N/A |
| Any SAE | 0 (0.0) | 0 (0.0) |
| AE leading to discontinuation (D/C) | 2 (6.1) 2 | 1 (2.9) 1 |
| Study drug related AE leading to D/C | 1 (3.0) 1 | 0 (0.0) |

The tolerability profile found in this study allowed future studies of the combination of xanomeline and trospium chloride to proceed.

Example 5—KAR-003 Phase I Study of KarXT, a Xanomeline+Trospium Combined Formulation This study was a Phase 1, randomized, multiple-dose, adaptive design, inpatient study to assess the safety and tolerability of KarXT in normal healthy volunteers aged 18 to 60 years. Subjects signed the informed consent and underwent Screening assessments on Days−21 to −1. Upon successfully completing all Screening assessments, subjects returned to the study clinic on Day 0 for baseline safety assessments and enrollment into the study and were randomized 3:1 in each cohort into one of two treatment arms: KarXT or placebo. Subjects were assigned to 1 of 4 cohorts (Cohort 1, 2, 3, or 4).

The study drug was administered BID on Days 1 through 7. A combination dosage formulation of both xanomeline and trospium was used in all cohorts. All cohorts began with a 2-day lead-in of KarXT 50/20 BID (for subjects randomized to active treatment); after the 2-day lead-in period, the unblinded pharmacist dispensed the study drug to each subject per the subject's randomization assignment for 5 days of specified cohort dosing, for a total of 7 days of treatment. Matching placebo was administered throughout the study to maintain the blind. A sentinel group was introduced to the study for Cohorts 2 to 4 and was monitored for safety and tolerability by the Data Safety Evaluation Group (DSEG), such that about 30% of the proposed cohort was treated and assessed for safety before the rest of the cohort was dosed. Subjects and study clinic staff were blinded to treatment. The Dose Selection Committee (DSC) was unblinded to decide dosing for subsequent treatment groups.

Serial blood samples for the PK assessment of xanomeline and trospium were drawn on Days 1, 3, and 7. More blood was sampled at routine intervals for monitoring trough concentrations of xanomeline and trospium and clinical laboratory assessments. On Day 1, saliva volume was collected twice. A saliva volume was measured predose on Day 1 and then daily (afternoon) on Days 1 through 7 at about the same time of day to avoid diurnal variations. Other assessments included pupil size measurements and Bristol stool scale assessments. Subjects remained in the study clinic for the full duration of treatment (7 days). Following a safety assessment on Day 8, subjects were discharged from the study clinic and asked to return about 14 days after administration of the study drug for a final safety assessment.

During the study, following the 2-day lead-in of KarXT 50/20 BID (for subjects randomized to active treatment) in each cohort, subjects were dosed as follows:

In Cohort 1, subjects completed Days 3 through 7 of dosing of KarXT 100/20 BID (total daily dose (TDD) of 200 mg xanomeline plus 40 mg trospium) or placebo.

In Cohort 2, the sentinel group (Group 2a) discontinued dosing after the Day 4 morning dose. The dosage for subjects in Cohort 2 was KarXT 150/20 BID (TDD of 300 mg xanomeline plus 40 mg trospium) or placebo. Dosing of Cohort 2 was discontinued (DSEG decision based on observed tolerability concerns). The study proceeded to dosing of the Cohort 3 sentinel group (Group 3a) as the DSC determined that further dosing of Cohort 2 with KarXT 150/20 BID was unlikely to be tolerated well enough to warrant further developing this dose combination for a clinical population.

In Cohort 3, the sentinel group (Group 3a) completed Days 3 through 7 of dosing of KarXT 150/40 BID (TDD of 300 mg xanomeline plus 80 mg trospium) or placebo. The second group in Cohort 3 (Group 3b) discontinued dosing after the Day 5 morning dose.

In Cohort 4, the sentinel group (Group 4a), the second group (Group 4b), and the remaining group (Group 4c) completed Days 3 through 7 of dosing of KarXT 125/40 BID (TDD of 250 mg xanomeline plus 80 mg trospium) or placebo.

Ninety-six subjects were planned, 248 subjects were screened, 69 subjects were randomized, 51 subjects completed the study, and 18 subjects discontinued the study. The population included male and female healthy subjects aged 18 to 60 years at screening with a body mass index of 18 to 40 kg/m'. Subjects were excluded from the study if they had a history of irritable bowel syndrome or serious constipation requiring treatment within 6 months before Screening. Subjects were also excluded from the study if they had a history or presence of any disease or condition, including psychiatric or neurological diseases that, in the Investigator's opinion, would have jeopardized the subject's safety or the study's validity. Table 21 summarizes the demographics and baseline characteristics by treatment group. The demographic and baseline characteristics were consistent between the Safety Population and the PK Population.

TABLE 21

Summary of Demographics and Baseline Characteristics by Treatment Group - Safety Population

| Characteristic Category/Statistic | Cohort 1 KarXT 100/20 BID | Cohort 2 KarXT 150/20 BID [1] | Cohort 3 KarXT 150/40 BID [2] | Cohort 4 KarXT 125/40 BID | Placebo | Total |
|---|---|---|---|---|---|---|
| n | 18 | 5 | 12 | 18 | 16 | 69 |
| Mean (SD) | 42.0 (12.9) | 39.0 (8.80) | 38.2 (9.4) | 39.8 (9.56) | 37.9 (10.61) | 39.6 (10.51) |
| Gender - n (%) | | | | | | |
| Male | 11 (61.1) | 3 (60.0) | 5 (41.7) | 9 (50.0) | 13 (81.3) | 41 (59.4) |
| Female | 7 (38.9) | 2 (40.0) | 7 (58.3) | 9 (50.0) | 3 (18.8) | 28 (40.6) |
| Race - n (%) | | | | | | |
| White | 8 (44.4) | 1 (20.0) | 7 (58.3) | 6 (33.3) | 4 (25.0) | 26 (37.7) |
| Black or African American | 9 (50.0) | 4 (80.0) | 5 (41.7) | 12 (66.7) | 12 (75.0) | 42 (60.9) |
| Asian | 0 (0.0) | 0 (0.0) | 0 (0.0) | 0 (0.0) | 0 (0.0) | 0 (0.0) |
| American Indian or Alaska Native | 0 (0.0) | 0 (0.0) | 0 (0.0) | 0 (0.0) | 0 (0.0) | 0 (0.0) |
| Native Hawaiian or Other Pacific Islander | 0 (0.0) | 0 (0.0) | 0 (0.0) | 0 (0.0) | 0 (0.0) | 0 (0.0) |
| Other | 1 (5.6) | 0 (0.0) | 0 (0.0) | 0 (0.0) | 0 (0.0) | 1 (1.4) |
| Ethnicity - n (%) | | | | | | |
| Hispanic or Latino | 2 (11.1) | 1 (20.0) | 2 (16.7) | 2 (11.1) | 1 (6.3) | 8 (11.6) |
| Not Hispanic or Latino | 16 (88.9) | 4 (80.0) | 10 (83.3) | 16 (88.9) | 15 (93.8) | 61 (88.4) |

TABLE 21-continued

Summary of Demographics and Baseline Characteristics by Treatment Group - Safety Population

| Characteristic Category/Statistic | Cohort 1 KarXT 100/20 BID | Cohort 2 KarXT 150/20 BID [1] | Cohort 3 KarXT 150/40 BID [2] | Cohort 4 KarXT 125/40 BID | Placebo | Total |
|---|---|---|---|---|---|---|
| Baseline weight (kg) | | | | | | |
| Mean (SD) | 81.8 (15.0) | 81.0 (12.1) | 81.3 (13.6) | 73.5 (8.9) | 77.6 (10.3) | 78.5 (12.2) |
| Baseline height (cm) | | | | | | |
| Mean (SD) | 172.5 (9.5) | 168.8 (5.8) | 170.7 (10.1) | 166.1 (6.8) | 172.1 (8.8) | 170.1 (8.8) |
| Baseline body mass index (kg/m$^2$) | | | | | | |
| Mean (SD) | 27.4 (3.8) | 28.4 (3.8) | 27.8 (3.7) | 26.7 (3.2) | 26.3 (3.7) | 27.1 (3.6) |

1. Cohort 2 sentinel group (5 subjects randomized to KarXT 150/20 BID and 1 subject randomized to placebo) was discontinued after the Day 4 morning dose.
2. During the study, Cohort 3 Group 3b (8 subjects randomized to KarXT 150/40 BID and 1 subject randomized to placebo) was discontinued after the Day 5 morning dose.

Serial blood samples for assessing the PK of xanomeline and trospium were collected from all subjects in each cohort on Days 1, 3, and 7 before the morning dose and at 1, 2, 3, 4, 6, 8, 10, and 12 hours after the morning dose. The PK parameters listed below were calculated from the individual xanomeline and trospium concentration-time profiles by standard non-compartmental methods. Dose-normalized parameters were calculated for $C_{max}$ and area under the concentration-time curve (AUC) values. During the study, additional blood samples for monitoring trough concentrations of xanomeline and trospium were collected on Days 2, 4, 5, and 6 before the morning dose and before discharge on Day 8.

Safety evaluations included spontaneously reported adverse events, ECGs, laboratory assessments, vital signs, assessments of saliva volumes, Bristol stool scale, pupil size, and physical examinations. Descriptive statistics (n, mean, standard deviation, median, minimum, and maximum) summarized the continuous data by treatment group. Geometric mean (GM), geometric percent coefficient of variation (CV %), quartiles, or box plots were generated. The count and frequency tabulated categorical measurements, although formal statistics were not conducted.

Treatment groups were summarized as follows unless otherwise specified: KarXT 50/20 BID (for adverse events and Day 1 PK summaries only), KarXT 100/20 BID, KarXT 125/40 BID, KarXT 150/20 BID, KarXT 150/40 BID, and placebo (Empty Vcaps® Plus Capsules and Capsugel®; all cohort placebo groups combined). The safety evaluation was based on spontaneously reported adverse events, ECGs, laboratory assessments, and vital signs. Exploratory analyses of saliva volumes, Bristol stool scale, and pupil size were also conducted.

Xanomeline was well absorbed into the systemic circulation following oral administration of the KAR-003 formulation at all dosages. Peak concentrations of xanomeline were observed at a median time of 2 hours across all treatment groups and study days.

Median $t_{1/2}$ values for xanomeline were similar between treatment groups and across study days, indicating that $t_{1/2}$ was not dose-dependent. Median $t_{1/2}$ ranged from 3.4 to 5.8 hours.

GM xanomeline exposures did not increase dose-proportionally on Day 3 from 100 to 150 mg when xanomeline was administered with 20 mg trospium or from 125 to 150 mg when xanomeline was administered with 40 mg trospium. Lower xanomeline exposures were observed following treatment with KarXT 150/40 compared to KarXT 125/40. Day 3 GM xanomeline exposures ($C_{max}$, $AUC_{0-last}$, and $AUC_{0-12\ hr}$) were similar when the 150 mg xanomeline dose was administered with 20 and 40 mg trospium. On Day 7, GM xanomeline exposures increased slightly more than dose-proportionally from 125 to 150 mg when xanomeline was administered with 40 mg trospium.

Minimal to no xanomeline accumulated in plasma from Day 3 to Day 7 following treatment with KarXT 100/20 BID and KarXT 125/40 BID; however, there was accumulation following administration of KarXT 150/40 BID in 3 of the 4 subjects who completed the study. The mean accumulation ratios for the KarXT 150/40 BID group were 366.2% for RAUC and 445.4% for $RC_{max}$.

Example 6—Xanomeline Pharmacokinetics of KAR-003 Compared to KAR-001

Comparing xanomeline GM exposures between KAR-001 (75 mg xanomeline TID±20 mg trospium BID) and the KarXT 100/20 BID group from KAR-003 showed that $C_{max}$ values and $AUC_{0-6\ hr}$ (KAR-003) or $AUC_{0-tau}$ (KAR-001) values were greater in KAR-003 (Days 3 and 7) than the corresponding exposures from KAR-001 (Days 3 and 9). The median $T_{max}$ was observed at 2 hours in both studies and both days (Days 3 and 9 for KAR-001, and Days 3 and 7 for KAR-003). These data indicate that the KarXT formulation enhanced xanomeline exposures.

Trospium was absorbed into the systemic circulation following oral administration of the KarXT formulation at all dosages. Peak concentrations of trospium were observed at a median time of 1.0 hour across all treatment groups and study days.

Median $t_{1/2}$ values for trospium were similar between treatment groups on Day 3, with values ranging between 4.1 and 4.8 hours. On Day 7, median $t_{1/2}$ values were similar for the KarXT 100/20 BID (4.9 hours) and KarXT 125/40 BID (4.5 hours) treatments but were slightly longer for the KarXT 150/40 BID group (7.1 hours).

GM trospium exposures increased slightly less than dose-proportionally on Day 3 from 20 to 40 mg when administered with 150 mg xanomeline. Day 3 GM trospium exposures ($C_{max}$, $AUC_{0-last}$, and $AUC_{0-12\ hr}$) were greater when the 20 mg BID dose of trospium was administered with 100 mg BID xanomeline compared to 150 mg BID xanomeline.

Day 3 GM trospium exposures were similar when the 40 mg trospium BID dose was given with 125 mg xanomeline BID and 150 mg xanomeline BID.

Trospium did not accumulate in plasma from Day 3 to Day 7 following administration of KarXT 100/20 BID, KarXT 125/40 BID, and KarXT 150/40 BID. Trospium accumulated in plasma from Day 1 to Day 7 for the KarXT 100/20 BID group. Mean Day 7/Day 1 accumulation ratios were 348.7% (RAUC) and 379.9% ($RC_{max}$).

Comparing trospium GM exposures between KAR-001 and the KarXT 100/20 BID group from KAR-003 showed that $C_{max}$ and $AUC_{0-12\ hr}$ values from KAR-003 were greater than the corresponding exposures from KAR-001 on both days (Days 3 and 9 for KAR-001 and Days 3 and 7 for KAR-003). The median $T_{max}$ for trospium was observed at 1.0 hour in both studies on both days. These data indicate that the KarXT formulation enhanced trospium exposures.

Figure 42:
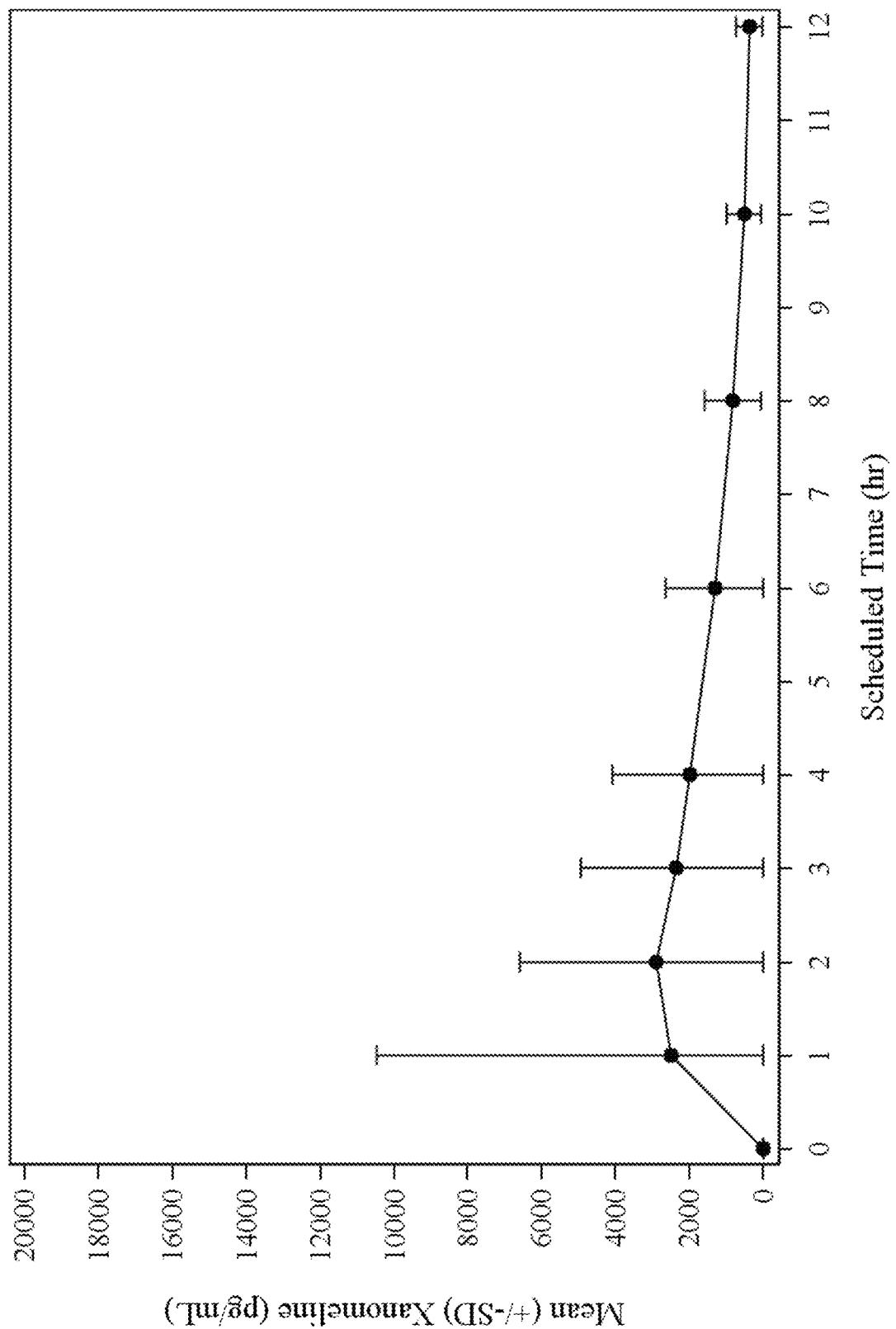
FIG. 42 depicts the mean (±standard deviation) xanomeline pharmacokinetic concentrations on Day 1 for KarXT 50/20 twice-daily treatment for all cohorts of the KAR-003 pharmacokinetic population.

All cohorts of KAR-003 started with a 2-day lead-in period of KarXT 50/20 BID for subjects randomized to KarXT. FIG. 42 presents the mean (±SD) xanomeline PK concentrations, and Table 22 summarizes xanomeline PK parameters on Day 1 for KarXT 50/20 BID treatment of all cohorts for the PK Population. No sample collected before administering the first dose of xanomeline on Day 1 displayed measurable concentrations of xanomeline. Concentrations of xanomeline were quantifiable (>50 pg/mL) at all time points after administering the Day 1 morning dose through 12 hours.

TABLE 22

Xanomeline PK Parameters on Day 1 for KarXT 50/20 BID (All Cohorts)

| Characteristic | n | Statistic |
|---|---|---|
| $C_{max}$ (pg/mL) | 53 | 1972.3 (131.8) |
| $T_{max}$ (h) | 53 | 2.0 (1.0, 8.0) |

TABLE 22-continued

Xanomeline PK Parameters on Day 1 for KarXT 50/20 BID (All Cohorts)

| Characteristic | n | Statistic |
|---|---|---|
| $t_{1/2}$ (h) | 48 | 3.4 (2.0, 4.6) |
| $AUC_{0-last}$ (h*pg/mL) | 53 | 10775.5 (102.2) |
| $AUC_{0-12hr}$ (h*pg/mL) | 52 | 10810.3 (103.5) |
| $AUC_{0-inf}$ (h*pg/mL) | 48 | 12836.1 (97.7) |

Figure 43:
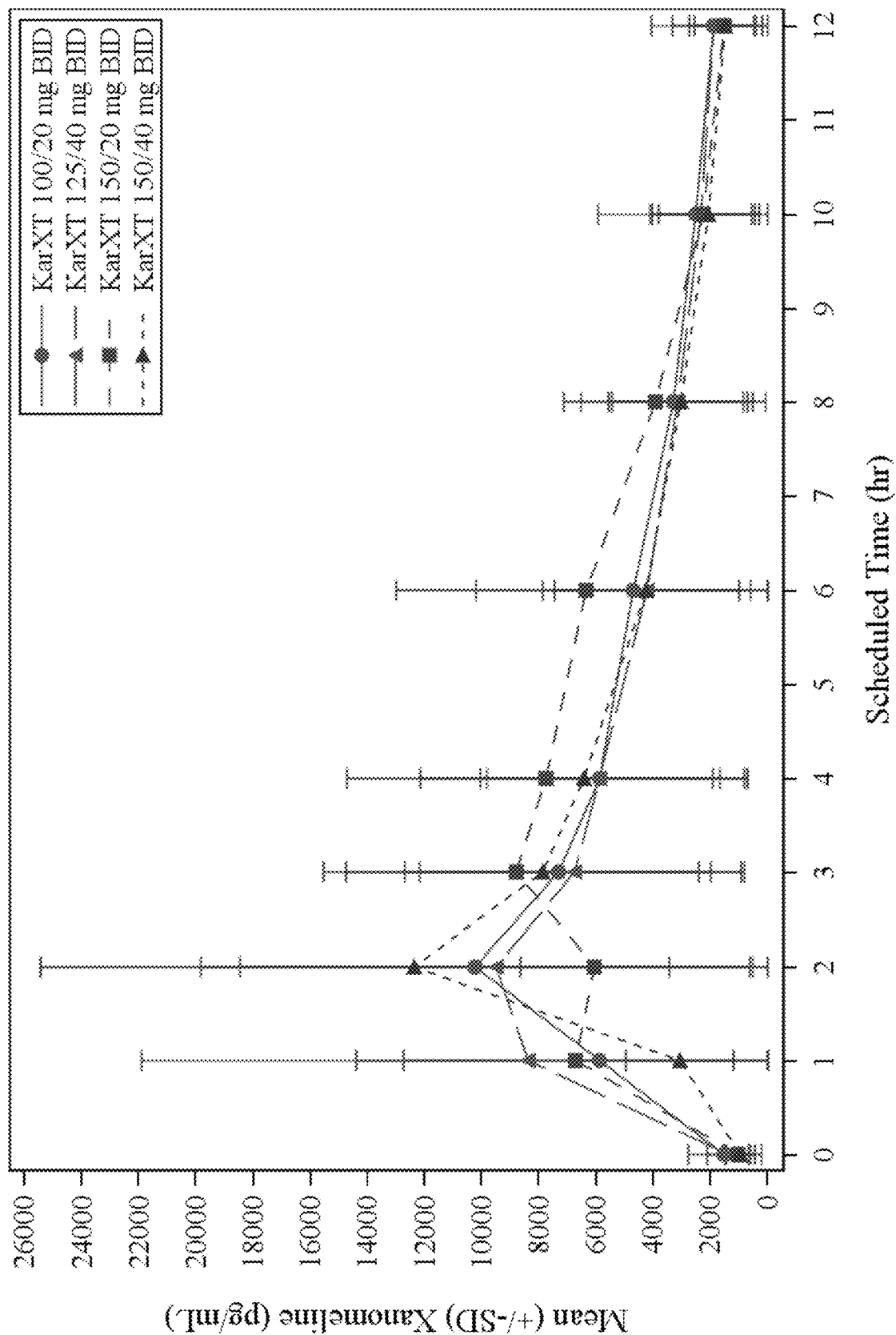
FIG. 43 depicts the mean (±standard deviation) xanomeline pharmacokinetic concentrations by treatment on Day 3 for KarXT 50/20 twice-daily treatment for all cohorts of the KAR-003 pharmacokinetic population.

FIG. 43 presents the mean (±SD) xanomeline PK concentrations by treatment on Day 3 for the PK population, and Table 23 summarizes these parameters. Concentrations of xanomeline were quantifiable in samples before administering the morning dose of study drug on Day 3 and at all time points after administering the Day 3 morning dose through 12 hours for all cohorts, except for one subject who had a xanomeline plasma concentration<50.0 pg/mL at 12 hours post-dose. Inter-subject variability ranged from 23.7% to 58.2% (CV %) for $T_{max}$, 79.8% to 136.3% (geometric CV %) for $C_{max}$, 21.6% to 26.3% (CV %) for $t_{112}$, and 77.1% to 96.1% (geometric CV %) for $AUC_{0-12\ hr}$ across the four treatment groups. The median $T_{max}$ for xanomeline on Day 3 was 2 hours for the KarXT 100/20 BID, KarXT 125/40 BID, KarXT 150/20 BID, and KarXT 150/40 BID groups. Individual $T_{max}$ values range from 1.0 to 6.0 hours across the four treatment groups. The $t_{1/2}$ was estimated in 51 of 53 subjects, in contrast to the previous study, KAR-001, where the elimination phase was not well characterized. The median $t_{1/2}$ on Day 3 for xanomeline was numerically similar across the four treatment groups. Median $t_{1/2}$ ranged from 3.4 to 4.3 hours. Individual $t_{1/2}$ values ranged from 2.4 to 8.6 hours across the four treatment groups.

TABLE 23

Xanomeline PK Parameters by Treatment on Day 3

| Statistic | Cohort 1 KarXT 100/20 BID | | Cohort 2 KarXT 150/20 BID | | Cohort 3 KarXT 150/40 BID | | Cohort 4 KarXT 125/40 BID | |
|---|---|---|---|---|---|---|---|---|
| | n | Statistic [2] | n | Statistic [2] | n | Statistic [2] | n | Statistic [2] |
| $C_{max}$ (pg/mL) | 18 | 7368.4 (106.2) | 5 | 7270.0 (79.8) | 12 | 7866.7 (136.3) | 18 | 8098.8 (99.1) |
| $T_{max}$ (h) | 18 | 2.0 (1.0, 3.0) | 5 | 2.0 (2.0, 4.0) | 12 | 2.0 (2.0, 6.0) | 18 | 2.0 (1.0, 6.0) |
| $t_{1/2}$ (h) | 17 | 3.9 (3.0, 5.8) | 5 | 3.4 (2.4, 4.3) | 12 | 3.6 (2.6, 6.1) | 17 | 4.3 (3.1, 8.6) |
| $AUC_{0-last}$ (h*pg/mL) | 18 | 42003.4 (86.9) | 5 | 48031.1 (92.0) | 12 | 39092.3 (96.1) | 18 | 43450.2 (74.4) |
| $AUC_{0-12hr}$ (h*pg/mL) | 17 | 40912.1 (88.8) | 5 | 48132.2 (92.0) | 12 | 39403.3 (96.1) | 17 | 43164.7 (77.1) |
| Dose-normalized $C_{max}$ (pg/mL/mg) | 18 | 73.7 (106.2) | 5 | 48.5 (79.8) | 12 | 52.4 (136.3) | 18 | 64.8 (99.1) |
| Dose-normalized $AUC_{0-last}$ (h*pg/mL/mg) | 18 | 420.0 (86.9) | 5 | 320.2 (92.0) | 12 | 260.6 (96.1) | 18 | 347.6 (74.4) |
| Dose-normalized $AUC_{0-12hr}$ (h*pg/mL/mg) | 17 | 409.1 (88.8) | 5 | 320.9 (92.0) | 12 | 262.7 (96.1) | 17 | 345.3 (77.1) |

Geometric CV % = 100*(exp($SD^2$) − 1)$^{0.5}$, where SD was the SD of the log-transformed data.

1. Cohort 2 sentinel group (5 subjects randomized to KarXT 150/20 BID and 1 subject randomized to placebo) was discontinued after the Day 4 morning dose.
2. During the study, Cohort 3 Group 3b (8 subjects randomized to KarXT 150/40 BID and 1 subject randomized to placebo) was discontinued after the Day 5 morning dose.

When KarXT was administered BID, as the xanomeline dose increased from 100 mg (Cohort 1) to 150 mg (Cohort 2) without changing the trospium dose (20 mg), the Day 3 dose-normalized GM exposures (dose-normalized GM $C_{max}$ and dose-normalized GM $AUC_{0\text{-}last}$ and $AUC_{0\text{-}12\ hr}$) for xanomeline decreased. Similarly, as the xanomeline dose increased from 125 mg (Cohort 4) to 150 mg (Cohort 3) without changing the trospium dosage (40 mg), the Day 3 dose-normalized GM exposures for xanomeline decreased slightly (i.e., xanomeline exposures were lower following treatment with KarXT 150/40 BID compared to treatment with KarXT 125/40 BID). Comparing xanomeline exposures following administration of 150 mg xanomeline BID with either 20 or 40 mg trospium BID showed that the Day 3 GM, $C_{max}$, $AUC_{0\text{-}last}$, and $AUC_{0\text{-}12\ hr}$ for xanomeline were similar.

Figure 44:
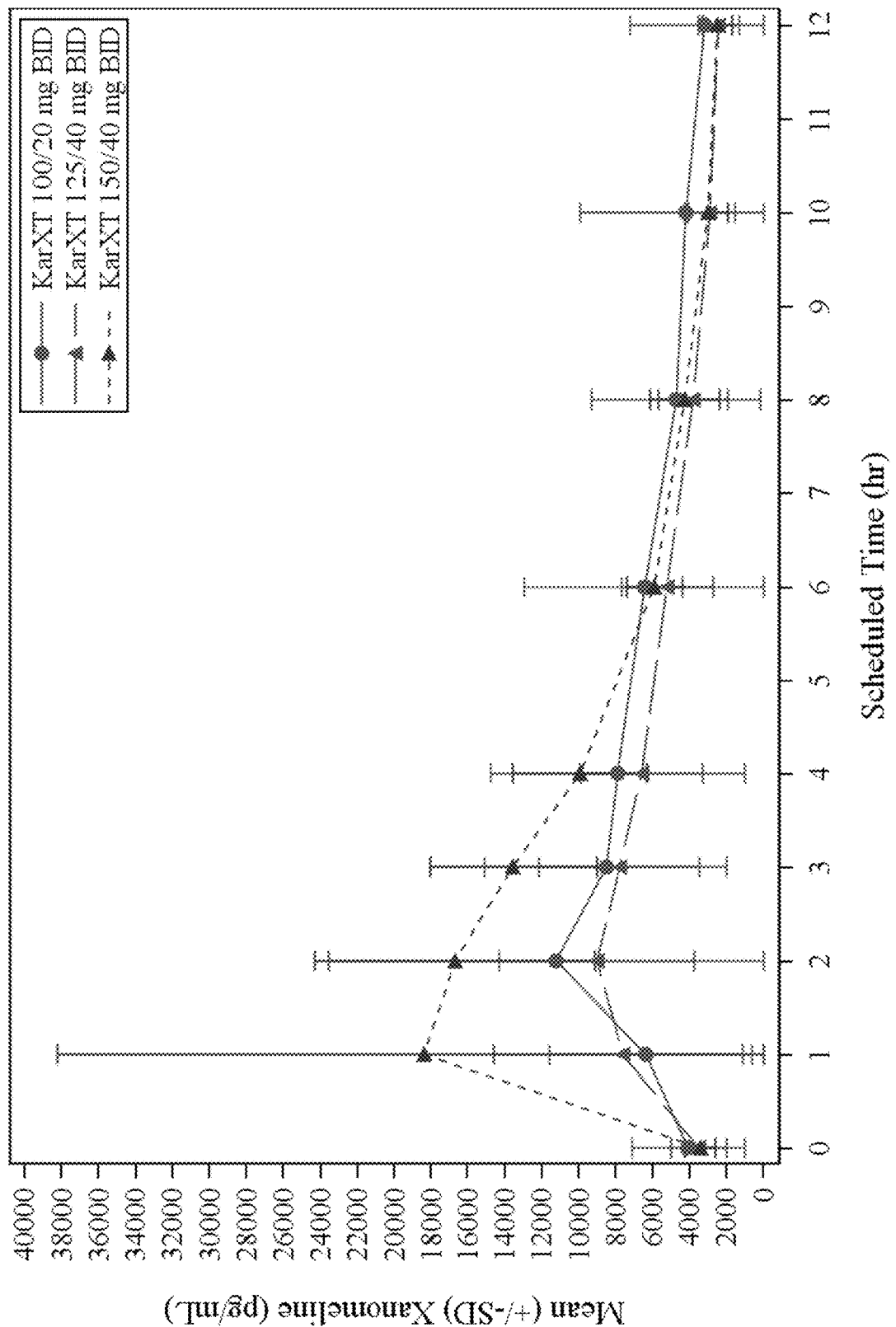
FIG. 44 depicts the mean (±standard deviation) xanomeline pharmacokinetic concentrations by treatment on Day 7 for KarXT 50/20 twice-daily treatment for all cohorts of the KAR-003 pharmacokinetic population.

FIG. 44 presents the mean (±SD) xanomeline PK concentrations by treatment on Day 7 for the PK population, and Table 24 summarizes these parameters. Concentrations of xanomeline were quantifiable in samples collected before administering the morning dose of the study drug on Day 7 and at all time points after the Day 7 morning dose through 12 hours for the KarXT 100/20 BID, KarXT 125/40 BID, and KarXT 150/40 BID groups. Inter-subject variability ranged from 38.3% to 47.9% (CV %) for $T_{max}$, 81.4% to 106.8% (geometric CV %) for $C_{max}$, 15.4% to 42.1% (CV %) for $t_{1/2}$, and 45.2% to 71.2% (geometric CV %) for $AUC_{0\text{-}12\ hr}$ across the KarXT 100/20 BID, KarXT 150/40 BID, and KarXT 125/40 BID groups. The median $T_{max}$ for xanomeline on Day 7 was 2.0 hours for the KarXT 100/20 BID, KarXT 125/40 BID, and KarXT 150/40 BID groups. Individual $T_{max}$ values ranged from 0.0 to 6.0 hours across the KarXT 100/20 BID, KarXT 150/40 BID, and KarXT 125/40 BID groups. The median $t_{1/2}$ for xanomeline on Day 7 was numerically similar for the KarXT 100/20 BID, KarXT 125/40 BID, and KarXT 150/40 BID groups. Median $t_{1/2}$ for xanomeline ranged from 4.6 to 5.8 hours. Individual $t_{1/2}$ values ranged from 3.6 to 14.0 hours across the KarXT 100/20 BID, KarXT 150/40 BID, and KarXT 125/40 BID groups.

TABLE 24

Xanomeline PK Parameters by Treatment on Day 7

| Statistic | Cohort 1 KarXT 100/20 BID | | Cohort 2 KarXT 150/20 BID | | Cohort 3 KarXT 150/40 BID | | Cohort 4 KarXT 125/40 BID | |
| --- | --- | --- | --- | --- | --- | --- | --- | --- |
| | n | Statistic [1] | n | Statistic [1] | n | Statistic [1] | n | Statistic [1] |
| $C_{max}$ (pg/mL) | 16 | 8373.6 (94.3) | N/A | N/A | 4 | 18191.3 (81.4) | 18 | 8112.7 (106.8) |
| $T_{max}$ (h) | 16 | 2.0 (0.0, 3.0) | N/A | N/A | 4 | 2.0 (1.0, 3.0) | 18 | 2.0 (1.0, 6.0) |
| $t_{1/2}$ (h) | 15 | 5.4 (3.6, 9.9) | N/A | N/A | 4 | 4.6 (3.9, 5.6) | 17 | 5.7 (4.0, 14.0) |
| $AUC_{0\text{-}last}$ (h*pg/mL) | 16 | 53810.8 (89.8) | N/A | N/A | 4 | 86347.8 (45.3) | 18 | 52727.0 (76.7) |
| $AUC_{0\text{-}12hr}$ (h*pg/mL) | 15 | 48138.3 (71.2) | N/A | N/A | 4 | 86540.9 (45.2) | 17 | 59945.1 (45.9) |
| Dose-normalized $C_{max}$ (pg/mL/mg) | 16 | 83.7 (94.3) | N/A | N/A | 4 | 121.3 (81.4) | 18 | 64.9 (106.8) |
| Dose-normalized $AUC_{0\text{-}last}$ (h*pg/mL/mg) | 16 | 538.1 (89.8) | N/A | N/A | 4 | 575.7 (45.3) | 18 | 421.8 (76.7) |
| Dose-normalized $AUC_{0\text{-}12hr}$ (h*pg/mL/mg) | 15 | 481.4 (71.2) | N/A | N/A | 4 | 576.9 (45.2) | 17 | 479.6 (45.9) |

Geometric CV % = 100*(exp(SD$^2$) − 1)$^{0.5}$, where SD was the SD of the log-transformed data.
1. Cohort 2 sentinel group (5 subjects randomized to KarXT 150/20 BID and 1 subject randomized to placebo) was discontinued after the Day 4 morning dose.
2. During the study, Cohort 3 Group 3b (8 subjects randomized to KarXT 150/40 BID and 1 subject randomized to placebo) was discontinued after the Day 5 morning dose.

When KarXT was administered BID, as the xanomeline dose increased from 125 mg (Cohort 4) to 150 mg (Cohort 3) without changing the trospium dosage (40 mg), the Day 7 dose-normalized GM exposures (dose-normalized GM $C_{max}$, $AUC_{0\text{-}last}$, and $AUC_{0\text{-}12\ hr}$) for xanomeline increased.

Table 25 summarizes xanomeline PK accumulation ratios (Day 7/Day 3) by treatment for the PK population. Based upon mean accumulation ratios of xanomeline following treatment with KarXT 100/20 BID (Cohort 1) and KarXT 125/40 BID (Cohort 4), minimal to no xanomeline accumulated in plasma from Day 3 to Day 7. Mean accumulation ratios for the KarXT 100/20 BID group were 133.4% for RAUC and 130.5% for $RC_{max}$, and for the KarXT 125/40 BID group were 143.9% for RAUC and 151.0% for $RC_{max}$. Only one subject in the KarXT 100/20 BID group showed lower exposures on Day 7 compared to Day 3. In contrast, xanomeline accumulated moderately in three of the four subjects in the KarXT 150/40 BID group who completed the study. The other subject in the KarXT 150/40 BID group showed similar exposures on Days 3 and 7. The mean accumulation ratios for the KarXT 150/40 BID group were 366.2% (RAUC) and 445.4% ($RC_{max}$).

TABLE 25

Xanomeline PK Accumulation Ratios (Day 7/Day 3) by Treatment

| Statistic | Cohort 1 KarXT 100/20 BID | | Cohort 2 KarXT 150/20 BID [1] | | Cohort 3 KarXT 150/40 BID [2] | | Cohort 4 KarXT 125/40 BID | |
|---|---|---|---|---|---|---|---|---|
| | n | Mean (SD) | n | Mean (SD) | n | Mean (SD) | n | Mean (SD) |
| RAUC (%) | 14 | 133.4 (45.1) | N/A | N/A (N/A) | 4 | 366.2 (321.3) | 16 | 143.9 (80.9) |
| $RC_{max}$ (%) | 16 | 130.5 (55.1) | N/A | N/A (N/A) | 4 | 445.4 (537.0) | 18 | 151.0 (122.7) |

RAUC = 100*Day 7 $AUC_{0-12hr}$/Day 3 $AUC_{0-12hr}$. $RC_{max}$ = 100*Day 7 $C_{max}$/Day 3 $C_{max}$.
1. Cohort 2 sentinel group (5 subjects randomized to KarXT 150/20 BID and 1 subject randomized to placebo) was discontinued after the Day 4 morning dose.
2. During the study, Cohort 3 Group 3b (8 subjects randomized to KarXT 150/40 BID and 1 subject randomized to placebo) was discontinued after the Day 5 morning dose.

Figure 45:
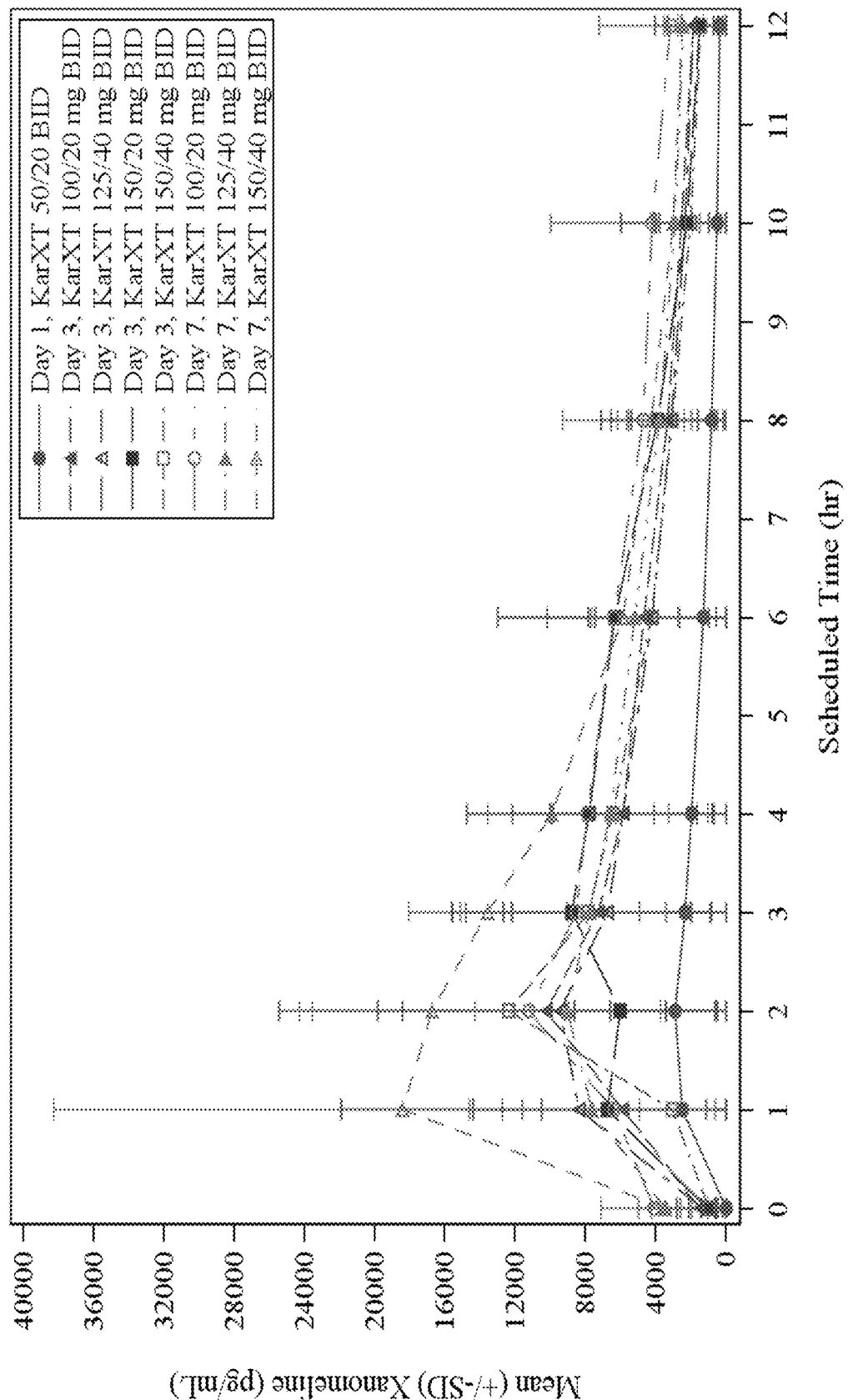
FIG. 45 depicts the mean (±standard deviation) xanomeline pharmacokinetic concentrations by treatment and visit for the KAR-003 pharmacokinetic population.
Figure 46:
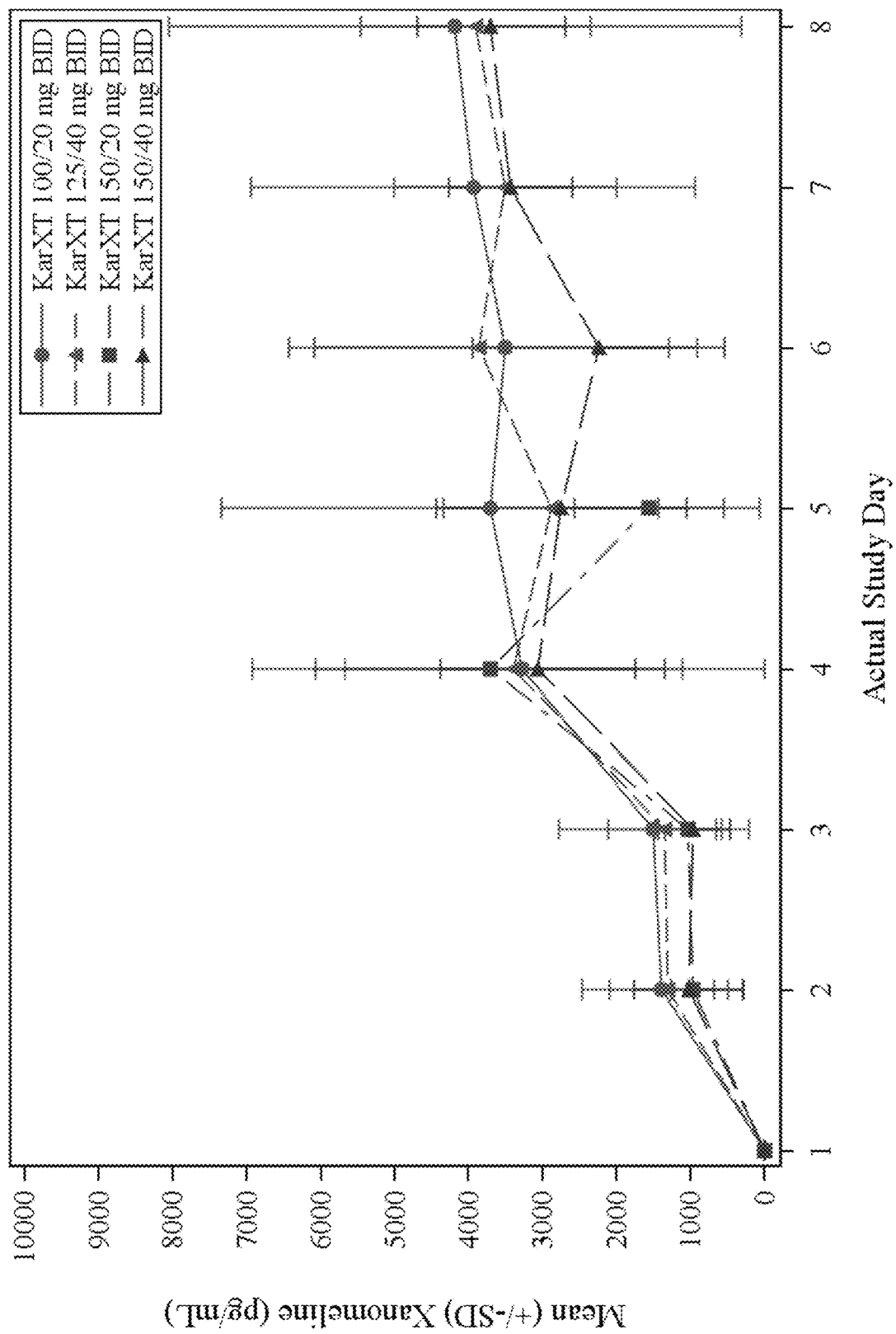
FIG. 46 depicts the mean (±standard deviation) xanomeline pharmacokinetic trough concentrations by treatment for the KAR-003 pharmacokinetic population.

FIG. 45 compares the mean (±SD) xanomeline PK concentration-time profiles by treatment and visit (Day) for the PK population. FIG. 46 presents mean (±SD) xanomeline PK trough concentrations by treatment for the PK population. Attaining a steady state was not assessed.

Comparing xanomeline GM exposures between KAR-001 (75 mg xanomeline TID±20 mg trospium BID) (Table 23) and the KarXT 100/20 BID group from KAR-003 (Table 21) showed that $C_{max}$ values and $AUC_{0-6\ hr}$ (KAR-003) or $AUC_{0-tau}$ (AUC from time 0 to 6 hours) values (KAR-001) values on Day 3 for the KarXT 100/20 BID group (KAR-003) were about 2.3 to 2.6-fold greater than corresponding exposures from KAR-001 on Day 3.

Comparing Day 7 GM exposures for xanomeline for the KarXT 100/20 BID group from KAR-003 (Table 22) with Day 9 exposures from the xanomeline alone and xanomeline+trospium arms from KAR-001 (Table 23) showed that values on Day 7 for the KarXT 100/20 BID group (KAR-003) were about 1.4 to 1.8-fold greater than corresponding exposures from KAR-001 on Day 9. The median $T_{max}$ was 2.0 hours on Day 3 and Day 7 for KAR-003 (Table 22) and Day 3 and Day 9 for KAR-001 (Table 23). These data indicate that the KAR-003 formulation provided sufficient exposure and PK properties.

Table 26 summarizes a subset of KAR-003 xanomeline PK parameters for the KarXT 100/20 BID group on Day 3 and Day 7 for the PK Population. Table 27 presents a summary of a subset of KAR-001 xanomeline PK parameters for the treatments of KAR-001 on Day 3 and Day 9 for the PK Population.

TABLE 26

Subset of Xanomeline PK Parameters KarXT 100/20 BID on Days 3 and 7

| KAR-003 PK Parameter | Cohort 1 - KarXT 100/20 BID Day 3 | | Cohort 1 - KarXT 100/20 BID Day 7 | |
|---|---|---|---|---|
| Statistic | n | Statistic [1] | n | Statistic [1] |
| $C_{max}$ (pg/mL) | 18 | 7368.4 (106.2) | 16 | 8373.6 (94.3) |
| $T_{max}$ (h) | 18 | 2.0 (1.0, 3.0) | 16 | 2.0 (0.0, 3.0) |
| $AUC_{0-6hr}$ (h*pg/mL) | 18 | 28564.2 (88.2) | 16 | 35129.1 (85.2) |

TABLE 27

Subset Xanomeline PK Parameters for KAR-001 on Days 3 and 9

| KAR-001 PK Parameter | Xanomeline Alone [1] | | | | Xanomeline + Trospium [2] | | | |
|---|---|---|---|---|---|---|---|---|
| | Day 3 | | Day 9 | | Day 3 | | Day 9 | |
| Statistic | n | Statistic [3] | n | Statistic [3] | n | Statistic [3] | n | Statistic [3] |
| $C_{max}$ (pg/mL) | 32 | 2951.1 (107.7) | 31 | 4572.6 (123.5) | 34 | 3043.0 (84.5) | 32 | 4698.5 (99.5) |
| $T_{max}$ (h) | 32 | 2.0 (2.0, 5.9) | 31 | 2.0 (0.0, 5.9) | 34 | 2.0 (1.0, 5.9) | 32 | 2.0 (1.0, 4.0) |
| $AUC_{0-tau}$ (h*pg/mL) | 11 | 12585.1 (132.4) | 21 | 24808.6 (85.4) | 17 | 11638.8 (71.3) | 22 | 20347.9 (107.3) |

Geometric CV % = $100*(exp(SD^2) - 1)^{0.5}$, where SD was the SD of the log-transformed data.

In KAR-001, xanomeline dosing started on Day 3. Hence Day 3 is the first day of xanomeline dosing and Day 9 is the seventh day of xanomeline dosing.

1. In KAR-001, the xanomeline-alone treatment arm received 2 placebo capsules TID during the 2-day lead-in phase, then xanomeline 75 mg TID (TDD 225 mg) and placebo on Days 3 through 9.

2. In KAR-001, the xanomeline plus trospium arm received trospium 20 mg BID (TDD 40 mg) and placebo BID; and 2 placebo capsules QD during the 2-day lead-in phase; then xanomeline 75 mg TID and trospium 20 mg BID (TDD 40 mg) and placebo QD on Days 3 through 9.

3. Statistics for parameters presented as geometric mean (geometric CV %), except for $T_{max}$, which is presented as the median with minimum and maximum values.

Figure 47:
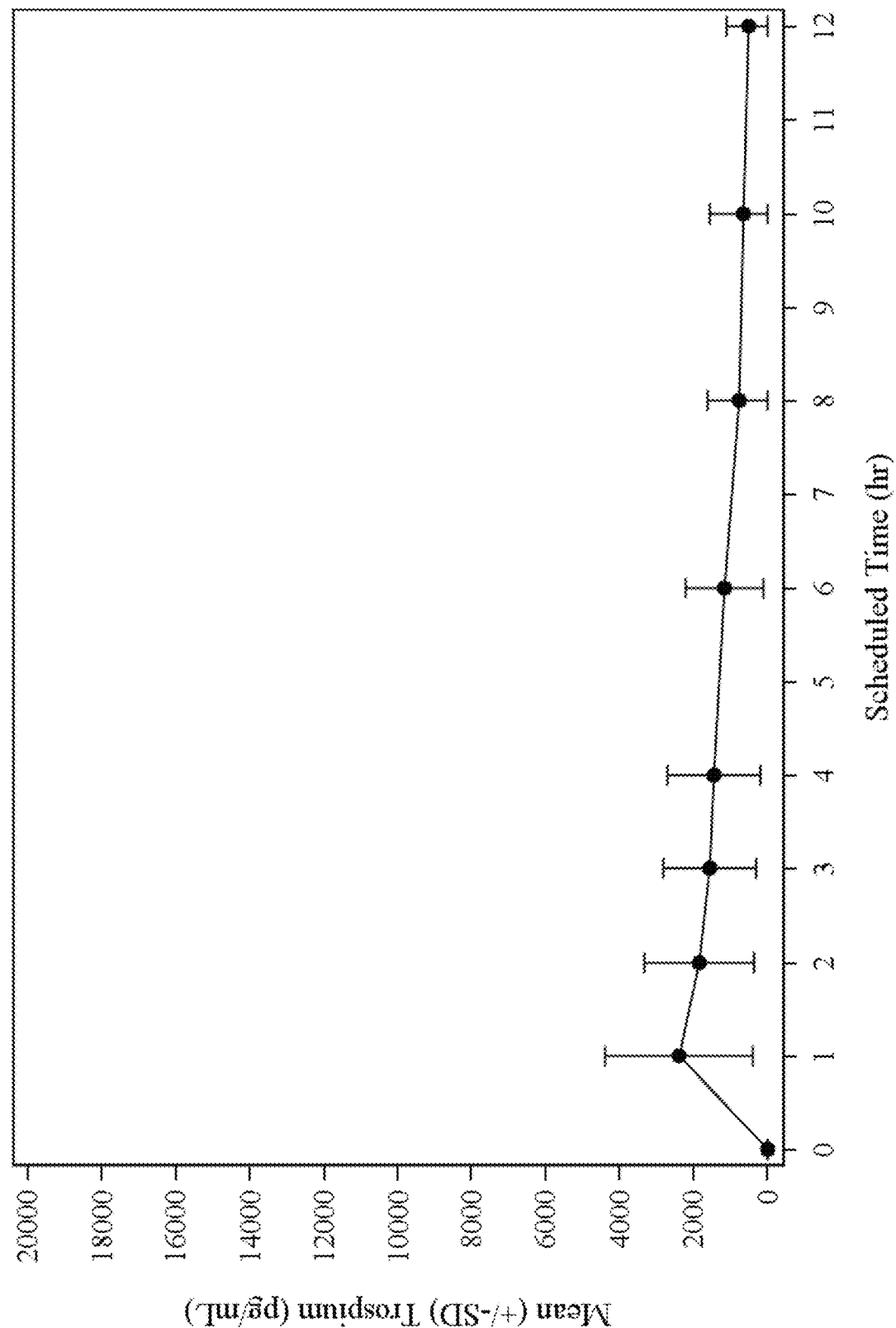
FIG. 47 depict the mean (±standard deviation) trospium pharmacokinetic concentrations on Day 1 for the KarXT 50/20 twice-daily treatment for all cohorts of the KAR-003 pharmacokinetic population.

FIG. 47 presents mean (±SD) trospium PK concentrations on Day 1 for the KarXT 50/20 BID treatment (all cohorts) for the PK population, and Table 28 summarizes these parameters. No samples collected before administering the first dose of trospium on Day 1 displayed measurable concentrations of trospium. Concentrations of trospium were quantifiable (>20 pg/mL) at all time points after administration of the Day 1 morning dose through 12 hours.

TABLE 28

Trospium PK Parameters on Day 1 for KarXT 50/20 BID (All Cohorts)

| Statistic | n | Statistic [1] |
|---|---|---|
| $C_{max}$ (pg/mL) | 53 | 1824.7 (98.7) |
| $T_{max}$ (h) | 53 | 1.0 (1.0, 10.0) |
| $t_{1/2}$ (h) | 26 | 4.5 (3.2, 5.1) |
| $AUC_{0-last}$ (h*pg/mL) | 53 | 10286.5 (86.3) |
| $AUC_{0-12hr}$ (h*pg/mL) | 49 | 10623.7 (78.5) |
| $AUC_{0-inf}$ (h*pg/mL) | 26 | 16526.6 (70.6) |

Geometric CV % = $100*(exp(SD^2) - 1)^{0.5}$, where SD was the SD of the log-transformed data.
1. Statistics for parameters are presented as geometric mean (geometric CV %), except for $t_{1/2}$ and $T_{max}$, which are presented as medians with minimum and maximum values.

Figure 48:
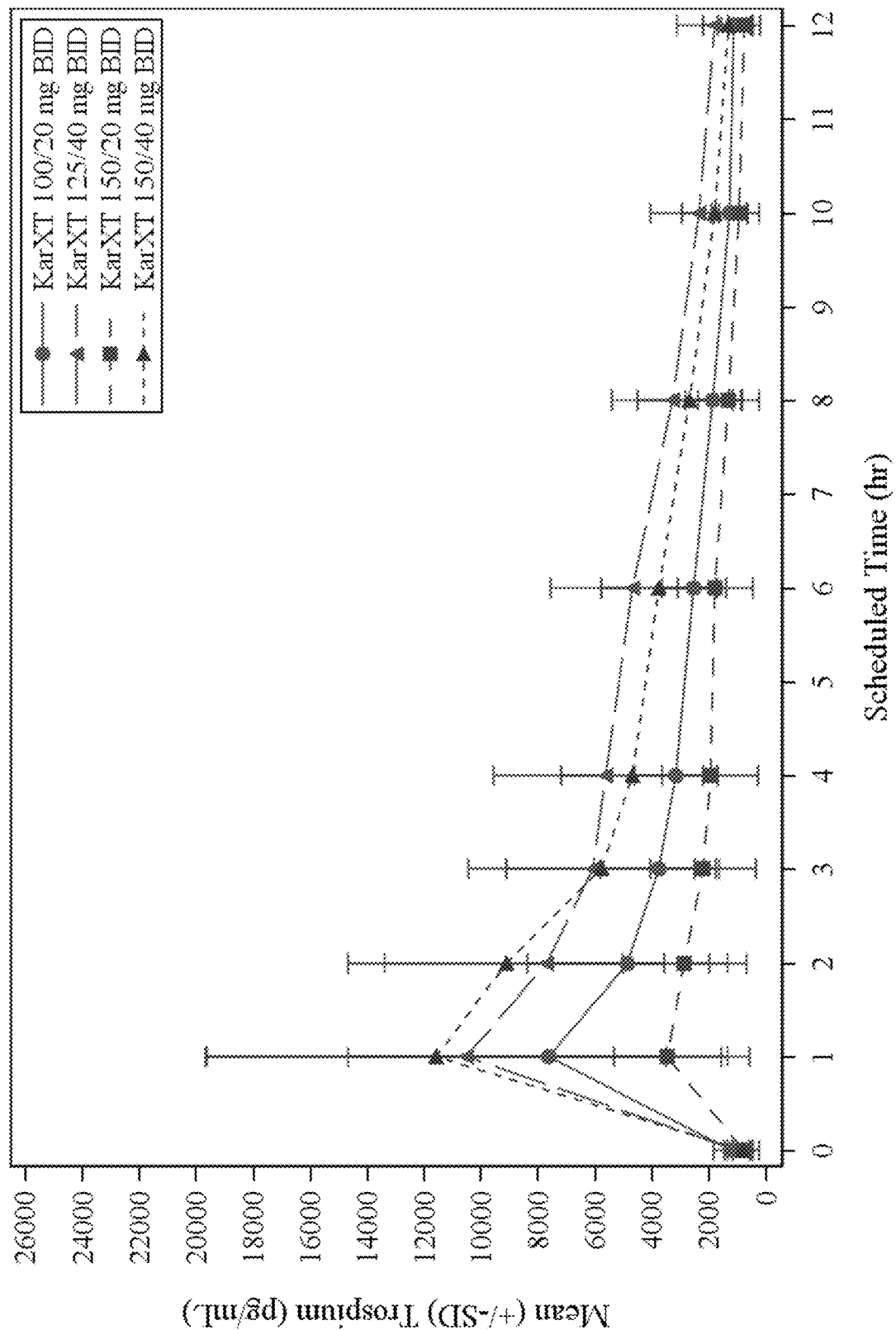
FIG. 48 depicts the mean (±standard deviation) trospium pharmacokinetic concentrations by treatment on Day 3 for the KAR-003 pharmacokinetic population.

FIG. 48 presents mean (±SD) trospium PK concentrations by treatment on Day 3 for the PK population, and Table 29 summarizes these parameters. Concentrations of trospium were quantifiable in samples collected before administering the morning dose of the study drug on Day 3 and at all time points after administering the Day 3 morning dose through 12 hours for all treatment groups (except for one subject who had a trospium plasma concentration<20.0 pg/mL at 12 hours post-dose. Inter-subject variability ranged from 0.0% to 83.0% (CV %) for $T_{max}$, 54.8% to 80.7% (geometric CV %) for $C_{max}$, 9.1% to 34.0% (CV %) for $t_{1/2}$, and 59.0% to 67.6% (geometric CV %) for $AUC_{0-12\ hr}$ across the four treatment groups.

The median $T_{max}$ for trospium on Day 3 was 1.0 hour for the KarXT 100/20 BID, KarXT 125/40 BID, KarXT 150/20 BID, and KarXT 150/40 BID groups. Individual $T_{max}$ values ranged from 1.0 to 6.0 hours across the 4 treatment groups. The median $t_{1/2}$ for trospium on Day 3 was numerically similar across the 4 treatment groups; median $t_{1/2}$ ranged from 4.1 to 4.8 hours. Individual $t_{1/2}$ values ranged from 2.8 to 9.0 hours across the 4 treatment groups.

When KarXT was administered BID, as the trospium dose increased from 20 mg (Cohort 2) to 40 mg (Cohort 3) without changing xanomeline dose (150 mg), the Day 3 dose-normalized GM exposures for trospium increased. Comparing Day 3 trospium exposures following administration of 20 mg trospium BID with either 100 mg (Cohort 1) or 150 mg (Cohort 2) xanomeline BID showed that GM $C_{max}$, $AUC_{0-last}$, and $AUC_{0-12\ hr}$ for trospium were greater when the 20 mg BID dose of trospium was administered with 100 mg xanomeline BID compared to 150 mg xanomeline BID.

Similarly, comparing trospium exposures following administration of 40 mg trospium BID with either 125 mg (Cohort 4) or 150 mg (Cohort 3) xanomeline BID showed that the GM $C_{max}$, $AUC_{0-last}$, and $AUC_{0-12\ h}$ for trospium were generally similar when trospium was administered with 125 and 150 mg xanomeline BID on Day 3.

Figure 49:
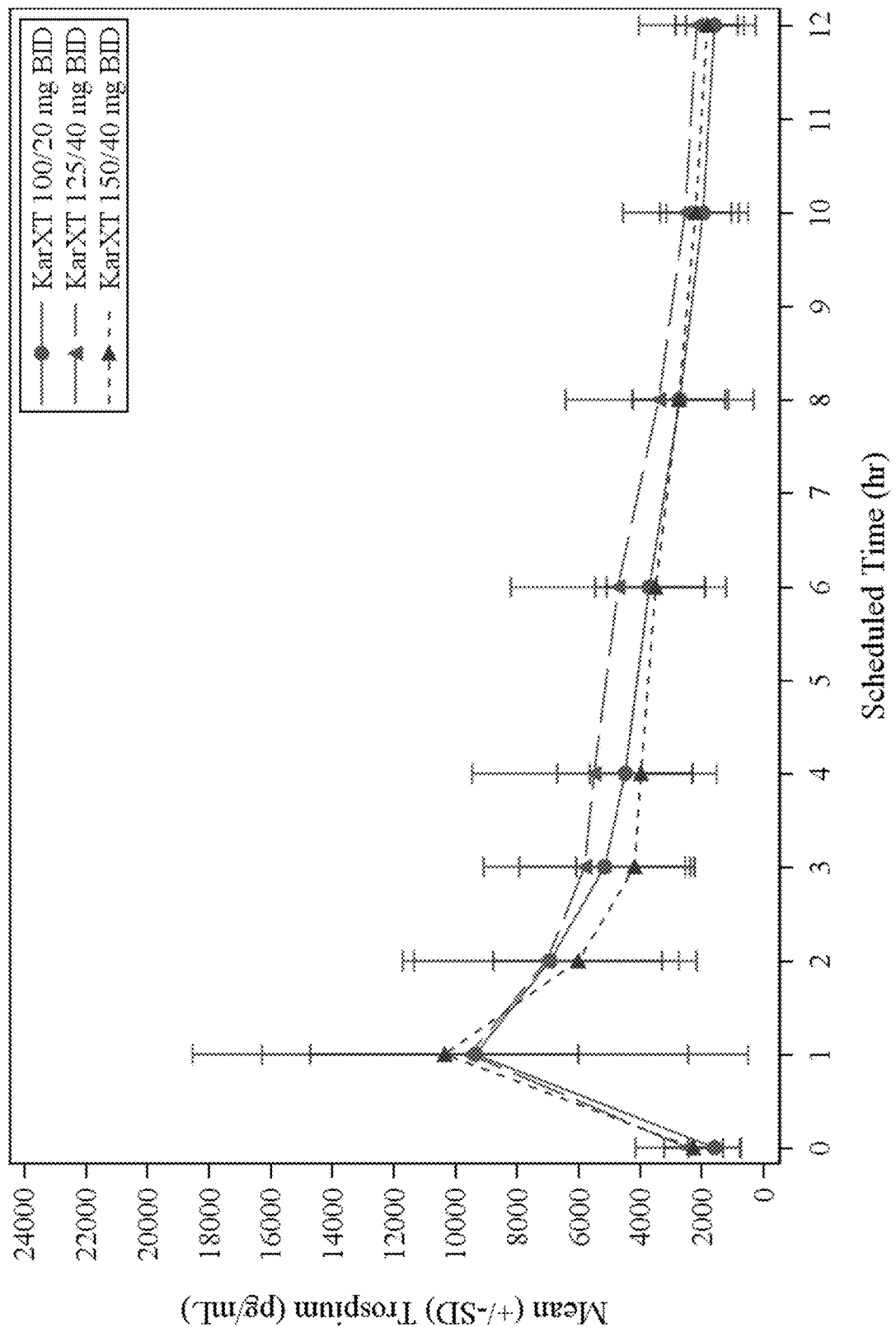
FIG. 49 depicts the mean (±standard deviation) trospium pharmacokinetic concentrations by treatment on Day 7 for the KAR-003 pharmacokinetic population.

FIG. 49 presents mean (±SD) trospium PK concentrations by treatment on Day 7 for the PK population, and Table 30 summarizes the parameters. Concentrations of trospium were quantifiable in samples collected before administering the morning dose of the study drug on Day 7 and at all time points after the Day 7 morning dose through 12 hours for the KarXT 100/20 BID, KarXT 125/40 BID, and KarXT 150/40 BID groups. Inter-subject variability ranged from 0.0% to 86.3% (CV %) for $T_{max}$, 51.2% to 93.8% (geometric CV %) for $C_{max}$, 23.0% to 44.5% (CV %) for $t_{1/2}$, and 59.4% to 76.7% (geometric CV %) for $AUC_{0-12\ hr}$ across the KarXT 100/20 BID, KarXT 150/40 BID, and KarXT 125/40 BID groups.

TABLE 29

Trospium PK Parameters by Treatment on Day 3

| Statistic [3] | Cohort 1 KarXT 100/20 BID | | Cohort 2 KarXT 150/20 BID [1] | | Cohort 3 KarXT 150/40 BID [2] | | Cohort 4 KarXT 125/40 BID | |
|---|---|---|---|---|---|---|---|---|
| | n | Statistic | n | Statistic | n | Statistic | n | Statistic |
| $C_{max}$ (pg/mL) | 18 | 5705.6 (80.7) | 5 | 3109.0 (54.8) | 12 | 9838.7 (67.3) | 18 | 8496.4 (74.9) |
| $T_{max}$ (h) | 18 | 1.0 (1.0, 3.0) | 5 | 1.0 (1.0, 1.0) | 12 | 1.0 (1.0, 2.0) | 18 | 1.0 (1.0, 6.0) |
| $t_{1/2}$ (h) | 18 | 4.8 (3.3, 7.6) | 5 | 4.6 (4.3, 5.3) | 12 | 4.1 (3.0, 8.0) | 18 | 4.2 (2.8, 9.0) |
| $AUC^{0-last}$ (h*pg/mL) | 18 | 29175.4 (59.0) | 5 | 17560.8 (64.8) | 12 | 43581.1 (64.4) | 18 | 46214.2 (67.5) |
| $AUC_{0-12hr}$ (h*pg/mL) | 18 | 29253.9 (59.0) | 5 | 17612.9 (64.8) | 12 | 44072.6 (64.3) | 18 | 46333.3 (67.6) |
| Dose-normalized $C_{max}$ (pg/mL/mg) | 18 | 285.3 (80.7) | 5 | 155.5 (54.8) | 12 | 246.0 (67.3) | 18 | 212.4 (74.9) |
| Dose-normalized $AUC_{0-last}$ (h*pg/mL/mg) | 18 | 1458.8 (59.0) | 5 | 878.0 (64.8) | 12 | 1089.5 (64.4) | 18 | 1155.4 (67.5) |
| Dose-normalized $AUC_{0-12hr}$ (h*pg/mL/mg) | 18 | 1462.7 (59.0) | 5 | 880.6 (64.8) | 12 | 1101.8 (64.3) | 18 | 1158.3 (67.6) |

Geometric CV % = $100*(exp(SD^2) - 1)^{0.5}$, where SD was the SD of the log-transformed data.
1. Cohort 2 sentinel group (5 subjects randomized to KarXT 150/20 BID and 1 subject randomized to placebo) was discontinued after the Day 4 morning dose.
2. During the study, Cohort 3 Group 3b (8 subjects randomized to KarXT 150/40 BID and 1 subject randomized to placebo) was discontinued after the Day 5 morning dose.
3. Statistics for parameters presented as geometric mean (geometric CV %), except for $t_{1/2}$ and $T_{max}$ which are presented as medians with minimum and maximum values.

TABLE 30

Trospium PK Parameters by Treatment on Day 7

| Statistic [3] | Cohort 1 KarXT 100/20 BID | | Cohort 2 KarXT 150/20 BID [1] | | Cohort 3 KarXT 150/40 BID [2] | | Cohort 4 KarXT 125/40 BID | |
|---|---|---|---|---|---|---|---|---|
| | n | Statistic | n | Statistic | n | Statistic | n | Statistic |
| $C_{max}$ (pg/mL) | 16 | 7494.9 (88.3) | N/A | N/A (N/A) | 4 | 9588.0 (51.2) | 18 | 7213.8 (93.8) |
| $T_{max}$ (h) | 16 | 1.0 (0.0, 1.0) | N/A | N/A | 4 | 1.0 (1.0, 1.0) | 18 | 1.0 (0.0, 6.0) |
| $t_{1/2}$ (h) | 16 | 4.9 (3.1, 7.1) | N/A | N/A | 4 | 7.1 (4.4, 8.2) | 18 | 4.5 (3.7, 11.9) |
| $AUC_{0\text{-}last}$ (h*pg/mL) | 16 | 40377.8 (69.3) | N/A | N/A (N/A) | 4 | 41865.2 (59.4) | 18 | 44998.6 (76.7) |
| $AUC_{0\text{-}12hr}$ (h*pg/mL) | 16 | 40488.0 (69.3) | N/A | N/A (N/A) | 4 | 41997.6 (59.4) | 18 | 45137.6 (76.7) |
| Dose-normalized $C_{max}$ (pg/mL/mg) | 16 | 374.7 (88.3) | N/A | N/A (N/A) | 4 | 239.7 (51.2) | 18 | 180.3 (93.8) |
| Dose-normalized $AUC_{0\text{-}last}$ (h*pg/mL/mg) | 16 | 2018.9 (69.3) | N/A | N/A (N/A) | 4 | 1046.6 (59.4) | 18 | 1125.0 (76.7) |
| Dose-normalized $AUC_{0\text{-}12hr}$ (h*pg/mL/mg) | 16 | 2024.4 (69.3) | N/A | N/A (N/A) | 4 | 1049.9 (59.4) | 18 | 1128.4 (76.7) |

Geometric CV % = $100*(\exp(SD^2) - 1)^{0.5}$, where SD was the SD of the log-transformed data.
1. Cohort 2 sentinel group (5 subjects randomized to KarXT 150/20 BID and 1 subject randomized to placebo) was discontinued after the Day 4 morning dose.
2. During the study, Cohort 3 Group 3b (8 subjects randomized to KarXT 150/40 BID and 1 subject randomized to placebo) was discontinued after the Day 5 morning dose.
3. Statistics for parameters presented as geometric mean (geometric CV %), except for $t_{1/2}$ and $T_{max}$ which are presented as medians with minimum and maximum values.

The median $T_{max}$ for trospium on Day 7 was 1.0 hour for the KarXT 100/20 BID, KarXT 125/40 BID, and KarXT 150/40 BID treatments. Individual $T_{max}$ values ranged from 0.0 to 6.0 hours across the KarXT 100/20 BID, KarXT 150/40 BID, and KarXT 125/40 BID groups.

The median $t_{1/2}$ for trospium on Day 7 was similar for the KarXT 100/20 BID (4.9 hours) and KarXT 125/40 BID (4.5 hours) groups. The median $t_{1/2}$ was 7.1 hours for the KarXT 150/40 BID group. Individual $t_{1/2}$ values ranged from 3.1 to 11.9 hours across the KarXT 100/20 BID, KarXT 150/40 BID, and KarXT 125/40 BID groups.

As observed on Day 3, comparing Day 7 trospium exposures following administration of 40 mg trospium BID with either 125 mg (Cohort 4) or 150 mg (Cohort 3) xanomeline BID showed that the GM $C_{max}$, $AUC_{0\text{-}last}$, and $AUC_{0\text{-}12\,hr}$ for trospium were similar when trospium was administered with 125 and 150 mg xanomeline BID.

Table 31 summarizes trospium PK accumulation ratios (Day 7/Day 3; Day 7/Day 1) by treatment for the PK Population. Based upon mean trospium PK accumulation ratios, trospium accumulated minimally in the plasma from Day 3 to Day 7 following administration of KarXT 100/20 BID (Cohort 1) and had little to no accumulation following administration of KarXT 125/40 BID (Cohort 4) and KarXT 150/40 BID (Cohort 3). Two subjects showed lower exposures on Day 7 compared to Day 3 in the KarXT 100/20 BID group.

Accumulation ratios from Day 3 to Day 7 varied widely between subjects in the KarXT 125/40 BID and KarXT 150/20 BID groups. Mean accumulation ratios ranged from 108.6% to 141.4% for RAUC and from 111.0% to 135.8% for $RC_{max}$. Trospium accumulated moderately in the plasma from Day 1 to Day 7 for the KarXT 100/20 BID group. All but one subject showed higher trospium exposures on Day 7 compared to Day 1. Mean accumulation ratios were 348.7% for RAUC and 379.9% for $RC_{max}$. The possible effect of the increase in xanomeline dose (from 50 mg BID to 100 mg BID beginning on Day 3) on the PK and bioavailability of trospium cannot be ruled out as contributing to the increased exposures from Day 1 to Day 7.

TABLE 31

Trospium PK Accumulation Ratios (Day 7/Day 3; Day7/Day 1) by Treatment

| Statistic | Cohort 1 KarXT 100/20 BID | | Cohort 2 KarXT 150/20 BID [1] | | Cohort 3 KarXT 150/40 BID [2] | | Cohort 4 KarXT 125/40 BID | |
|---|---|---|---|---|---|---|---|---|
| | n | Mean (SD) | n | Mean (SD) | n | Mean (SD) | n | Mean (SD) |
| Day 7/Day 3 | | | | | | | | |
| RAUC (%) | 16 | 141.4 (56.6) | N/A | N/A (N/A) | 4 | 108.6 (39.0) | 18 | 125.0 (84.4) |
| $RC_{max}$ (%) | 16 | 135.8 (70.5) | N/A | N/A (N/A) | 4 | 111.0 (67.8) | 18 | 119.9 (91.0) |

TABLE 31-continued

Trospium PK Accumulation Ratios (Day 7/Day 3; Day7/Day 1) by Treatment

|  | Cohort 1 KarXT 100/20 BID | | Cohort 2 KarXT 150/20 BID [1] | | Cohort 3 KarXT 150/40 BID [2] | | Cohort 4 KarXT 125/40 BID | |
|---|---|---|---|---|---|---|---|---|
| Statistic | n | Mean (SD) | n | Mean (SD) | n | Mean (SD) | n | Mean (SD) |
| Day 7/Day 1 | | | | | | | | |
| RAUC (%) | 15 | 348.7 (242.9) | N/A | N/A (N/A) | N/A | N/A (N/A) | N/A | N/A (N/A) |
| $RC_{max}$ (%) | 16 | 379.89 (266.0) | N/A | N/A (N/A) | N/A | N/A (N/A) | N/A | N/A (N/A) |

1. Pharmacokinetic accumulation ratios of Day7/Day3: RAUC = 100*Day 7 $AUC_{0-12hr}$/Day 3 $AUC_{0-12hr}$ · $RC_{max}$ = 100*Day 7 $C_{max}$/Day 3 $C_{max}$.
2. Pharmacokinetic accumulation ratios of Day 7/Day 1: RAUC = 100*Day 7 $AUC_{0-12hr}$/Day 1 $AUC_{0-12hr}$ · $RC_{max}$ = 100*Day 7 $C_{max}$/Day 1 $C_{max}$.
3. Cohort 2 sentinel group (5 subjects randomized to KarXT 150/20 BID and 1 subject randomized to placebo) was discontinued after the Day 4 morning dose.
4. During the study, Cohort 3 Group 3b (8 subjects randomized to KarXT 150/40 BID and 1 subject randomized to placebo) was discontinued after the Day 5 morning dose.

Figure 50:
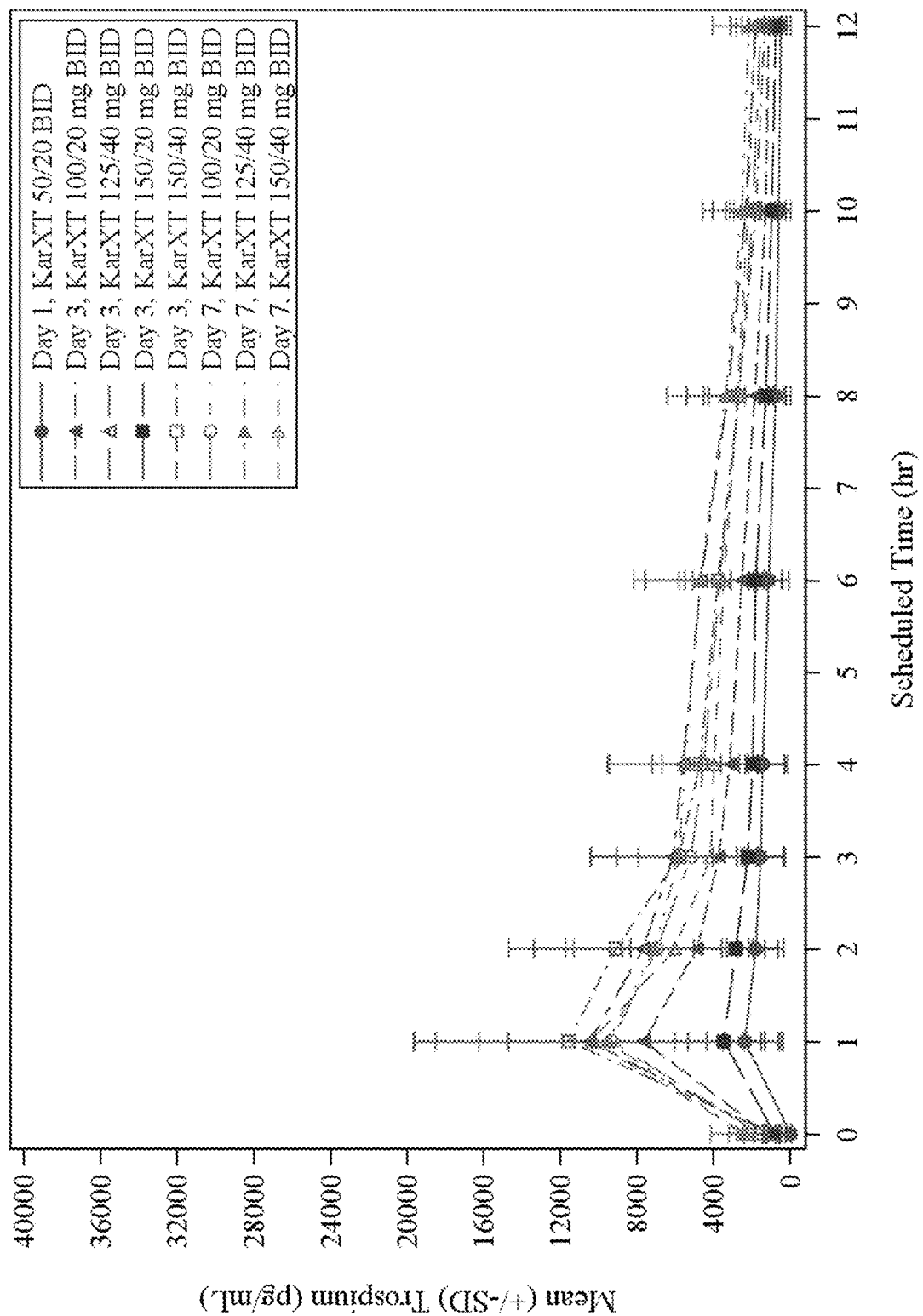
FIG. 50 depicts the mean (±standard deviation) trospium pharmacokinetic concentrations by treatment and visit for the KAR-003 pharmacokinetic population.
Figure 51:
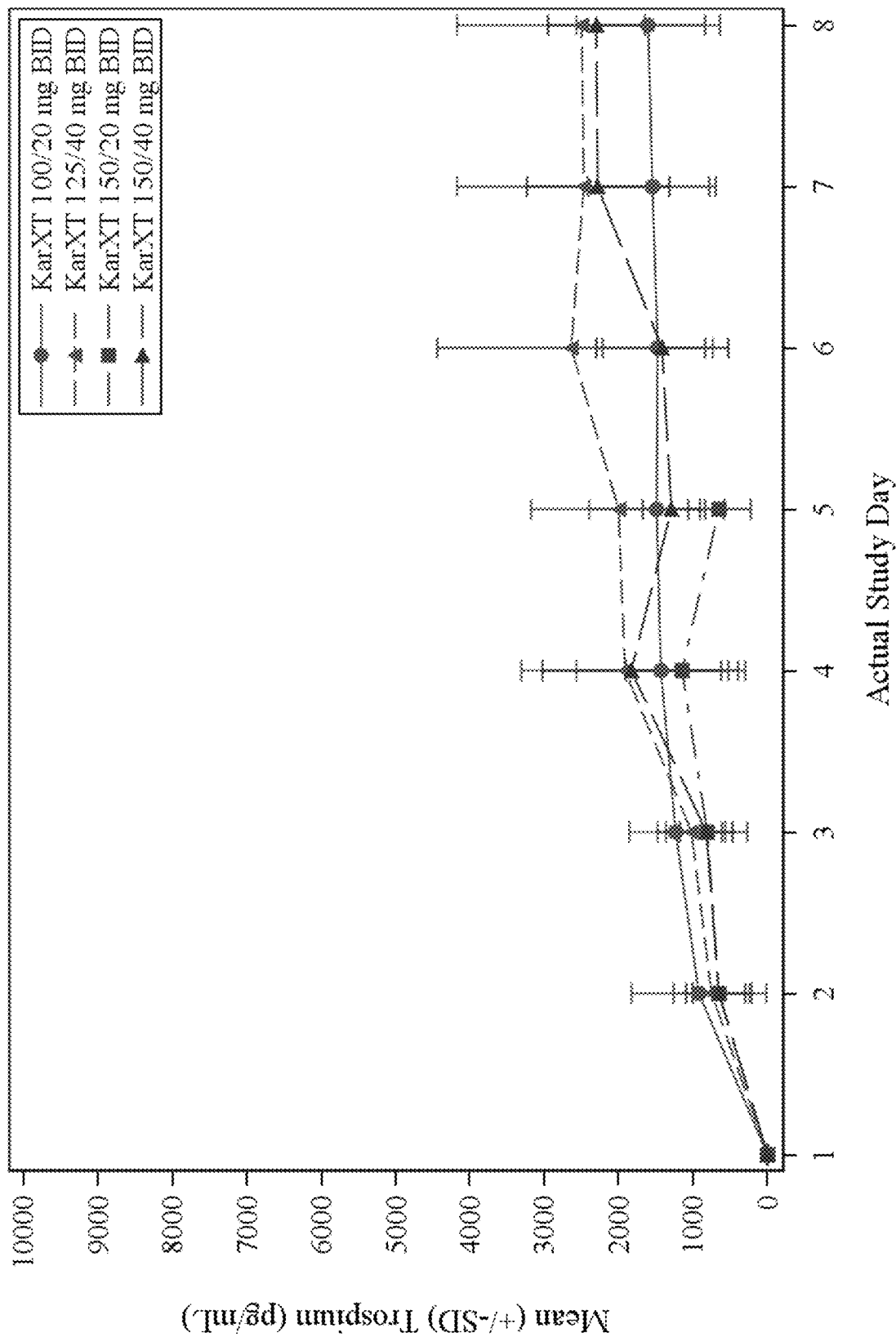
FIG. 51 depicts the mean (±standard deviation) trospium pharmacokinetic trough concentrations by treatment and visit for the KAR-003 pharmacokinetic population.

FIG. 50 compares mean (±SD) trospium PK concentration-time profiles by treatment and visit (Day) for the PK Population. FIG. 51 presents mean (±SD) trospium PK trough concentrations by treatment and visit (Day) for the PK Population. Attaining steady state was not assessed.

Example 7—Trospium Pharmacokinetics of KAR-003 Compared to KAR-001

Comparing GM exposures for trospium from Day 1 of KAR-001 (first dose of trospium alone with no prior treatment) (Table 33) and Day 1 of KAR-003 (first dose of xanomeline+trospium with no prior treatment) (Table 32) shows that the trospium exposures from KAR-003 are about 2.1- to 2.5-fold higher than those obtained from KAR-001. Although the comparison of Day 3 GM exposures between studies is not really a head-to-head comparison (xanomeline dosing did not start until Day 3 in the KAR-003 study), the number of doses and the daily dose of trospium administered to subjects is the same. The Day 3 GM trospium exposures from KAR-003 (Table 32) are also~2.4- to 3.3-fold higher than those obtained from KAR-001 (Table 33). Comparing Day 7 GM exposures for trospium for the KarXT 100/20 BID cohort (Cohort 1) from KAR-003 (Table 32) with Day 9 exposures from the xanomeline+trospium arm from KAR-001 (Table 33) indicates that exposures were once again higher (by approximately 3.5- to 4.3-fold) than those obtained from KAR-001.

The median $T_{max}$ for trospium was 1.0 hour on Day 3 and Day 7 for the KarXT 100/20 BID group for KAR-003 and on Day 3 and Day 9 for the xanomeline+trospium arm for KAR-001. Median $T_{max}$ for trospium was lower (1.0 hour) on Day 1 for the KarXT 50/20 BID group (KAR-003) compared to the median $T_{max}$ for trospium (3.0 hours on Day 1 for the trospium alone arm (KAR-001).

Table 32 summarizes a subset of KAR-003 trospium PK parameters for the KarXT 50/20 BID treatment (all cohorts) on Day 1 and for the KarXT 100/20 BID treatment on Day 3 and Day 7 for the PK Population. Table 33 summarizes a subset of KAR-001 trospium PK parameters for the trospium-alone treatment on Day 1 and the xanomeline+trospium treatment on Day 3 and Day 9 for the PK Population.

TABLE 32

Subset of KAR-003 Trospium PK Parameters for KarXT 50/20 BID
(All Cohorts) on Day 1 and KarXT 100/20 BID on Days 3 and 7

| KAR-003 PK Parameter | KAR 50/20 BID | | Cohort 1-KAR 100/20 BID | | | |
|---|---|---|---|---|---|---|
| | Day 1 | | Day 3 | | Day 7 | |
| | n | Statistic [1] | n | Statistic [1] | n | Statistic [1] |
| $C_{max}$ (pg/mL) | 53 | 1824.7 (98.7) | 18 | 5705.6 (80.7) | 16 | 7494.9 (88.3) |
| $T_{max}$ (h) | 53 | 1.0 (1.0, 10.0) | 18 | 1.0 (1.0, 3.0) | 16 | 1.0 (0.0, 1.0) |
| $AUC_{0-12hr}$ (h*pg/mL) | 49 | 10623.7 (78.5) | 18 | 29253.9 (59.0) | 16 | 40488.0 (69.3) |
| $AUC_{0-inf}$ (h*pg/mL) | 26 | 16526.6 (70.6) | N/A | N/A | N/A | N/A |

1. Statistics for parameters are presented as geometric mean (geometric CV %), except for $T_{max}$ which is presented as the median with minimum and maximum values.

TABLE 33

Subset of Trospium PK Parameters for KAR-001 on Days 1, 3, and 9

| KAR-001 PK Parameter | Trospium Alone [1] | | Xanomeline + Trospium [1] | | | |
|---|---|---|---|---|---|---|
| | Day 1 | | Day 3 | | Day 9 | |
| | n | Statistic [2] | n | Statistic [2] | n | Statistic [2] |
| $C_{max}$ (pg/mL) | 33 | 721.9 (78.2) | 34 | 1711.6 (89.8) | 33 | 1733.6 (124.1) |
| $T_{max}$ (h) | 33 | 3.0 (1.0, 5.9) | 34 | 1.0 (1.0, 5.9) | 33 | 1.0 (0.0, 4.0) |
| $AUC_{0-tau}$ (h*pg/mL) | 26 | 5028.6 (65.9) | 23 | 12176.3 (61.6) | 30 | 11395.2 (105.9) |
| $AUC_{0-inf}$ (h*pg/mL) | 26 | 7787.3 (55.4) | 23 | 18149.4 (62.0) | 30 | 17519.4 (93.2) |

Geometric CV % = $100*(exp(SD^2) - 1)^{0.5}$, where SD is the standard deviation of the log-transformed data. In KAR-001, xanomeline dosing started on Day 3. Hence Day 3 is the first day of xanomeline dosing and Day 9 is the seventh day of xanomeline dosing.
1. In KAR-001, the xanomeline + trospium arm received 20 mg trospium BID (TDD 40 mg) and placebo BID; and 2 placebo capsules QD during the 2-day lead-in phase; then 75 mg xanomeline TID and 20 mg trospium BID (TDD 40 mg) and placebo QD on Days 3 through 9.
2. Statistics for parameters are presented as geometric mean (geometric CV %), except for $T_{max}$ which is presented as the median with minimum and maximum values.

Table 34 lists the incidence of cholinergic TEAEs by system organ class (SOC) and preferred term for the Safety Population in the KAR-001 study. The overall subject incidence of cholinergic TEAEs was similar between the xanomeline+trospium arm (12 [34.3%] subjects) in KAR-001, the KarXT 100/20 BID group (7 [38.9%] subjects), and the KarXT 125/40 BID group (6 [33.3%] subjects).

TABLE 34

KAR-001 Incidence of Cholinergic Treatment-Emergent Adverse Events by System Organ Class and Preferred Term - Safety Population

| System Organ Class Preferred Term | Xanomeline Alone [1] (n = 34) n (%) # | Xanomeline + Trospium [2] (n = 35) n (%) # | Total (n = 69) n (%) # |
|---|---|---|---|
| Subjects with any TEAEs | 21 (61.8) 64 | 12 (34.3) 33 | 33 (47.8) 97 |
| Gastrointestinal disorders | 18 (52.9) 40 | 12 (34.3) 25 | 30 (43.5) 65 |
| Salivary hypersecretion | 12 (35.3) 16 | 9 (25.7) 11 | 21 (30.4) 27 |
| Nausea | 8 (23.5) 11 | 6 (17.1) 8 | 14 (20.3) 19 |
| Diarrhea | 7 (20.6) 8 | 2 (5.7) 4 | 9 (13.0) 12 |
| Vomiting | 5 (14.7) 5 | 2 (5.7) 2 | 7 (10.1) 7 |
| Skin and subcutaneous tissue disorders | 16 (47.1) 24 | 7 (20.0) 8 | 23 (33.3) 32 |
| Hyperhidrosis | 16 (47.1) 24 | 7 (20.0) 8 | 23 (33.3) 32 |

The percentage was calculated from the number of subjects in the column header as the denominator.
was the number of individual occurrences of the TEAE. The TEAEs were defined as adverse events that happened for the first time after dosing of study drug or existed before but worsened in severity or relationship to study drug after dosing. For noncholinergic adverse events, the first dose of any study drug (Day 1) was used, and for cholinergic adverse events, the first dose of xanomeline (Day 3) was used. Cholinergic adverse events had the additional specification that the start of the adverse event must have been within 24 hours (inclusive) of the last dose to be treatment-emergent. At each level of summation (total, system organ class term, preferred term), subjects who reported more than one adverse event were counted only once. During the study, a subject could have contributed to more than one preferred term.
In KAR-001, xanomeline dosing started on Day 3. Hence Day 3 was the first day of xanomeline dosing and Day 9 was the seventh day of xanomeline dosing.
1. In KAR-001, the xanomeline-alone treatment arm received two placebo capsules TID during the 2-day lead-in phase, then xanomeline 75 mg TID (TDD 225 mg) and placebo on Days 3 through 9.
2. In KAR-001, the xanomeline + trospium arm received trospium 20 mg BID (TDD 40 mg) and placebo BID; and two placebo capsules QD during the 2-day lead-in phase; then xanomeline 75 mg TID and trospium 20 mg BID (TDD 40 mg) and placebo QD on Days 3 through 9.

Subject incidence of salivary hypersecretion, hyperhidrosis, and diarrhea was higher in the xanomeline+trospium arm in KAR-001 compared to the KarXT 100/20 BID and KarXT 125/40 BID groups. Salivary hypersecretion occurred in 25.7% of subjects in the xanomeline+trospium arm in KAR-001, 5.6% of subjects in the KarXT 100/20 BID group, and no subjects in the KarXT 125/40 BID group. Hyperhidrosis occurred in 20.0% of subjects in the xanomeline+trospium arm in KAR-001, 5.6% of subjects in the KarXT 100/20 BID group, and 11.1% of subjects in the KarXT 125/40 BID group. Diarrhea occurred in 5.7% of subjects in the xanomeline+trospium arm in KAR-001, and no subjects in the KarXT 100/20 BID group or the KarXT 125/40 BID group.

The xanomeline+trospium arm in KAR-001 showed no other apparent trends compared to the KarXT 100/20 BID and KarXT 125/40 BID groups for nausea and vomiting. Nausea occurred in 17.1% of subjects in the xanomeline+trospium arm in KAR-001 and 22.2% of subjects in each KarXT 100/20 BID and KarXT 125/40 BID groups. Vomiting occurred in 5.7% of subjects in the xanomeline+trospium arm in KAR-001, 27.8% of subjects in the KarXT 100/20 BID group, and 5.6% of subjects in the KarXT 125/40 BID group.

Xanomeline and trospium were absorbed into the systemic circulation following oral administration of the KAR-003 formulation at all dosages. The PK results suggest that neither xanomeline nor trospium meaningfully impacted the PK behavior of the other drug. The KAR-003 formulation provided enhanced xanomeline and trospium blood levels compared to KAR-001, where both compounds were dosed apart.

No new safety signals were reported with the KarXT formulation. All TEAEs were mild or moderate in severity with no SAEs or deaths. Subject incidence of salivary hypersecretion, hyperhidrosis, and diarrhea was higher in the xanomeline+trospium arm in KAR-001 compared to the KarXT 100/20 BID and KarXT 125/40 BID groups in KAR-003.

The foregoing description is given for clearness of understanding only, and no unnecessary limitations should be understood therefrom, as modifications within the scope of the disclosure may be apparent to those having ordinary skill in the art. Throughout the specification, where compositions are described as including components or materials, it is contemplated that the compositions can also consist essentially of, or consist of, any combination of the recited components or materials, unless described otherwise. Likewise, where methods are described as including steps, it is contemplated that the methods can also consist essentially of, or consist of, any combination of the recited steps, unless described otherwise. The disclosure illustratively disclosed herein suitably may be practiced in the absence of any element or step which is not specifically disclosed herein.

The practice of a method disclosed herein, and individual steps thereof, can be performed manually and/or with the aid of or automation provided by electronic equipment. Although processes have been described with reference to embodiments, a person of ordinary skill in the art will readily appreciate that other ways of performing the acts associated with the methods may be used. For example, the order of various of the steps may be changed without departing from the scope or spirit of the method unless described otherwise. In addition, some of the individual steps can be combined, omitted, or further subdivided into additional steps.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables contained within the generic chemical formulae described herein are specifically embraced by the present invention just as if each and every combination was individually explicitly recited, to the extent that such combinations embrace stable compounds (i.e., compounds that can be isolated, characterized and tested for biological activity). In addition, all subcombinations of the chemical groups listed in the embodiments describing such variables, as well as all subcombinations of uses and medical indications described herein, are also specifically embraced by the present invention just as if each and every subcombination of chemical groups and subcombination of uses and medical indications was individually and explicitly recited herein.

All patents, publications, and references cited herein are hereby fully incorporated by reference. In case of conflict between the present disclosure and incorporated patents, publications, and references, the present disclosure should control.

What is claimed is:

1. A method of treating a disorder ameliorated by activating muscarinic receptors in a patient in need thereof, the method comprising administering between 100 mg and 125 mg xanomeline and/or a salt thereof and between 20 mg and 30 mg trospium salt to the patient twice daily;
   wherein the xanomeline and/or a salt thereof and trospium salt are administered as a pharmaceutical composition comprising a plurality of xanomeline beads having a core comprising the xanomeline or a salt thereof and optionally a coating, and a plurality of trospium beads having a core comprising the trospium salt and optionally a coating; and
   wherein the pharmaceutical composition is a capsule containing the plurality of xanomeline beads and the plurality of trospium beads.

2. The method of claim 1, wherein the disorder is chosen from schizophrenia, Alzheimer's disease, Parkinson's disease, depression, movement disorders, pain, drug addiction, tauopathy, and synucleinopathy.

3. The method of claim 1, wherein the disorder is schizophrenia.

4. The method of claim 1, wherein the administration is oral.

5. The method of claim 1, wherein the patient is treated for at least 7 days.

6. The method of claim 1, wherein the xanomeline and/or a salt thereof is xanomeline tartrate.

7. The method of claim 1, wherein the trospium salt is trospium chloride.

8. The method of claim 1, wherein the xanomeline and/or a salt thereof is xanomeline tartrate and the trospium salt is trospium chloride.

9. A method of treating schizophrenia in a patient in need thereof, the method comprising orally administering between 100 mg and 125 mg xanomeline tartrate and between 20 mg and 30 mg trospium chloride to the patient twice daily;
   wherein the xanomeline and/or a salt thereof and trospium salt are administered as a pharmaceutical composition comprising a plurality of xanomeline beads having a core comprising the xanomeline or a salt thereof and optionally a coating, and a plurality of trospium beads having a core comprising the trospium salt and optionally a coating.

10. The method of claim 9, wherein the patient is treated for at least 7 days.

11. The method of claim 1, wherein the size of the xanomeline beads is between 0.425 mm and 1.18 mm.

12. The method of claim 11, wherein the size of the xanomeline beads is between 0.6 mm and 0.85 mm.

13. The method of claim 1, wherein the size of the trospium beads is between 0.425 mm and 1.18 mm.

14. The method of claim 13, wherein the size of the trospium beads is between 0.6 mm and 0.85 mm.

15. The method of claim 9, wherein the size of the xanomeline beads is between 0.425 mm and 1.18 mm.

16. The method of claim 15, wherein the size of the xanomeline beads is between 0.6 mm and 0.85 mm.

17. The method of claim 9, wherein the size of the trospium beads is between 0.425 mm and 1.18 mm.

18. The method of claim 17, wherein the size of the trospium beads is between 0.6 mm and 0.85 mm.

* * * * *